(12) United States Patent
Nazare et al.

(10) Patent No.: US 9,346,762 B2
(45) Date of Patent: May 24, 2016

(54) PYRAZOLE DERIVATIVES AND THEIR USE AS LPAR5 ANTAGONISTS

(71) Applicant: SANOFI, Paris (FR)

(72) Inventors: Marc Nazare, Frankfurt am Main (DE); Detlef Kozian, Frankfurt am Main (DE); Andreas Evers, Frankfurt am Main (DE); Werngard Czechtizky, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/401,050

(22) PCT Filed: May 16, 2013

(86) PCT No.: PCT/EP2013/060171
§ 371 (c)(1),
(2) Date: Nov. 13, 2014

(87) PCT Pub. No.: WO2013/171317
PCT Pub. Date: Nov. 21, 2013

(65) Prior Publication Data
US 2015/0141477 A1    May 21, 2015

(30) Foreign Application Priority Data

May 18, 2012    (EP) .................................... 12305552

(51) Int. Cl.
| | | |
|---|---|---|
| C07D 231/12 | (2006.01) | |
| C07D 409/04 | (2006.01) | |
| C07D 231/56 | (2006.01) | |
| A61K 31/415 | (2006.01) | |

(52) U.S. Cl.
CPC ............ *C07D 231/12* (2013.01); *A61K 31/415* (2013.01); *C07D 231/56* (2013.01); *C07D 409/04* (2013.01)

(58) Field of Classification Search
CPC .. C07D 231/12; C07D 231/56; C07D 409/04; A61K 31/415
See application file for complete search history.

(56) References Cited

U.S. PATENT DOCUMENTS

2008/0194617 A1    8/2008    Tawaraishi

FOREIGN PATENT DOCUMENTS

| EP | 0382276 A2 | 8/1990 |
| WO | 2004022526 A1 | 3/2004 |
| WO | 2009080227 A2 | 7/2009 |
| WO | 2009109613 A2 | 9/2009 |
| WO | 2009109616 A2 | 9/2009 |
| WO | 2009109618 A2 | 9/2009 |
| WO | 2011015501 A2 | 2/2011 |
| WO | 2012028243 A1 | 3/2012 |
| WO | 2013171316 A1 | 11/2013 |

OTHER PUBLICATIONS

Database Registry Chemical Abstracts Service, Columbus, Ohio, Accession No. RN 1280538-92-2, RN 1279877-48-3, RN 1279845-01-0, RN 1279842-08-8, RN 1279831-82-1, RN 1279830-96-4, and RN 1279828-94-2, Entered STN: Apr. 14, 2011.*
Ito, Nobuyuki. Cancer Science 94(1), (2003) 3-8.*
International Search Report for International Patent Application No. PCT/EP2013/060171 dated Jun. 11, 2013 (mailed Jun. 27, 2013) p. 1-11.
A. F. Littke et al., "Palladium-Catalyzed Coupling Reactions of Aryl Chlorides" Angew. Chem. Int. Ed. 2002, 41, 4176-4211.
A. Padwa et al., "Reaction of Hydrazonyl Chlorides and Carboalkoxymethylene Triphenylphosphoranes to Give 5-Alkoxy Substituted Pyrazoles" J. Heterocycl. Chem., 1987, 24, 1225-1227.
A. R. Muci et al, "Practical Palladium Catalysts for C—N and C—O Bond Formation" Topics in current Chemistry 2002, 219, 131-209.
A. Tunoori et al., "Polymer-Bound Triphenylphosphine as Traceless Reagent for Mitsunobu Reactions in Combinatorial Chemistry: Synthesis of Aryl Ethers from Phenols and Alcohols" Tetrahedron Lett. 39 (1998) 8751-8754.
Amisten et al., "Gene expression profiling for the identification of G-protein coupled receptors in human platelets" Thromb Res (2008), 122, 47-57 (Oct. 24, 2007).
B. Yang et al. "Palladium-catalyzed amination of aryl halides and sulfonates" J. Organomet. Chem. 1999, 576, 125-146.

(Continued)

*Primary Examiner* — Samantha Shterengarts
(74) *Attorney, Agent, or Firm* — McDonnell Boehnen Hulbert & Berghoff LLP

(57) ABSTRACT

The present invention relates to compounds of the formula (I), wherein the residues $R^1$ to $R^5$, V, G and M have the meanings indicated in the claims. The compounds of the formula (I) are valuable pharmacologically active compounds for use in the treatment of diverse disorders, for example cardiovascular disorders like thromboembolic diseases or restenoses. The compounds of the invention are effective antagonists of the platelet LPA receptor LPAR5 (GPR92) and can in general be applied in conditions in which an undesired activation of the platelet LPA receptor LPAR5, the mast cell LPA receptor LPAR5 or the microglia cell LPA receptor LPAR5 is present or for the cure or prevention of which an inhibition of the platelet, mast cell or microglia cell LPA receptor LPAR5 is intended. The invention furthermore relates to processes for the preparation of compounds of the formula (I), their use, in particular as active ingredients in medicaments, and pharmaceutical compositions comprising them.

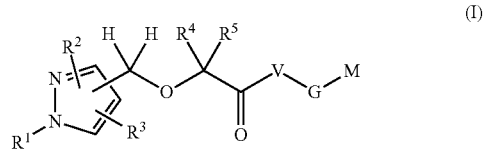

19 Claims, No Drawings

(56) References Cited

OTHER PUBLICATIONS

C. Baldoli et al., A Novel Synthesis of 5-Chloro-3-methoxycarbonyl-1-arylpyrazoles from Arylazomethylenetriphenylphosphoranes J. Heterocycl. Chem., 1989, 26, 241-244.
Choi et al., "LPA Receptors: Subtypes and Biological Actions" Ann Rev Pharmacol Toxicol (2010), 50, 157-186 (Oct. 21, 2009).
D. Butler et al., "New General Methods for the Substitution of 5-Chloropyrazoles. The Synthesis of 1,3-Dialkyl-5-chloropyrazol-4-yl Aryl Ketones and New 1,3-Dialkyl-2-pyrazolin-5-ones" J. Org. Chem., 1971, 36, 2542-2547.
D. Chan et al., "New N- and O-Arylations with Phenylboronic Acids and Cupric Acetate" Tetrahedron Lett. 1998, 39, 2933-2936.
D. Crich et al., "Some Observations on the Mechanism of the Mitsunobu Reaction" J. Org. Chem. 54 (1989) 257-259.
D. J. Camp et al., "Mechanism of the Mitsunobu Esterification Reaction. 1. The Involvement of Phosphoranes and Oxyphosphonium Salts" J. Org. Chem. 54 (1989) 3045-3049.
D. Jeon et al. "Synthesis of New 4-Benzoyl-5-hydroxy-3-Trifluoromethylpyrazole Derivatives via [1,3] Rearrangements of Benzoyl Group Using tert—Butyllithium" Synth. Commun., 1998, vol. 28, No. 12, S. 2159-2166.
D. L. Hughes et al. "A Mechanistic Study of the Mitsunobu Esterification Reaction" J. Am. Chem. Soc. 110, 1988, 6487-6491.
D. Nichols, "1-(2,5-Dimethoxy-4(-t rifluoromethyl)phenyl-)2-aminopropane: A Potent Serotonin 5-HT2A/2C Agonist" J. Med. Chem, 1994, 37, 4346-4351.
D. Sauer et al., "The Synthesis of 3(5)-[(2-Hydroxyethoxy)methyl]pyrazole-5(3)-carboxamide, an Acyclic Analogue of 4-Deoxypyrazofurin" J. Org. Chem., 1990, 40, 5535-5538.
F. Farina et al. "1,3-Dipolar Cycloadditions With Methyl 4-Oxo- and 4-Hydroxy-2-Butynoates. Synthesis of Functionalized Pyrazoles and Triazoles" Heterocycles, 1989, vol. 29., No. 5, S. 967-974.
F. Foti et al. "First Synthesis of a Bromonitrilimine. Direct Formation of 3-Bromopyrazole Derivatives." Tetrahedron Lett., 1999, 40, 2605-2606.
F. Qing et al. "First synthesis of ortho-trifluoromethylated aryl triflates" J. Chem. Soc. Perkin Trans. I 1997, 3053-3057.
Fleisher et al., "Improved oral drug delivery: solubility limitations of prodrugs" Advanced Drug Delivery Reviews 19 (1996) 115-130.
Frigola, J. et al. "Synthesis, structure and inhibitory effects on cyclooxygenase, lipoxygenase, thromboxane synthetase and platelet aggregation of 3-amino-4,5-dihydro-1H-pyrazole derivatives" Eur. J. Med. Chem. 1989: vol. 24, No. 4, pp. 435-445.
G.M. Pilling et al. "The Synthesis of 1H-Pyrazol-4-OLS From 2-(2-Alkylidenehydrazino)Acetic Acids" Tetrahedron Lett., 1988, 29, 1341-1342.
Guogang, T.U. et al. "Design, synthesis and biological evaluation of CB1 cannabinoid receptor ligands derived from the 1,5-diarylpyrazole scaffold" J Enzyme Inhibition and Med. Chem. 2011, vol. 26, No. 2, pp. 222-230.
H. Bundgaard, "Novel Chemical Approaches in Prodrug Design" Drugs of the Future vol. 16, No. 5, (1991) 443-458.
H. Ochi et al, "Synthesis of 2-Substituted 2,6-Dihydro-3-hydroxy-7H-pyrazolo[4,3-d]pyrimidin-7-ones" Chem. Pham. Bull., 1983, 31, 1228-1234.
H.V. Patel et al., "Concise and Efficient Synthesis of 1H-Pyrazoles: Reaction of [Hydroxy(tosyloxy)iodo]benzene with Ethyl 2,3-Dioxobutanoate-2-arylhydrazones" Synth. Commun., 1991, 21, 1583-1588.
J. Pawlas et al., "Synthesis of 1-Hydroxy-Substituted Pyrazolo[3,4-c]- and Pyrazolo[4,3-c]quinolines and -soquinolines from 4- and 5-Aryl-Substituted 1-Benzyloxypyrazoles" J. Org. Chem. 2000, 65, 9001-9006.
J. Pelletier et al., "Mitsunobu reaction modifications allowing product isolation without chromatography: application to a small parallel library" Tetrahedron Lett. 41 (2000) 797-800.

J. Wolfe et al. "Simple, Efficient Catalyst System for the Palladium-Catalyzed Amination of Aryl Chlorides, Bromides, and Triflates" J. Org. Chem. 2000, 65, 1158-1174.
K. I. Booker-Milburn "A Convenient Method for the Synthesis of C-5 Substituted 1-Tosylpyrazoles" Synlett 1992, 327-328.
K. Makino et al., "Selective Fluorination of Ethyl 1-Methylpyrazole-4-carboxylates with Poly(Hydrogen Fluoride)-Amine Compiex under Electrolytic Anodic Oxidation" J. Fluorine Chem. 1988, 39, 435-440.
K. Makino et al., "Synthesis of Pyrazoles" J. Heterocycl. Chem., 1998, 35, 489-497.
K. Makino et al., "Synthesis of Pyrazoles and Condensed Pyrazoles" J. Heterocycl. Chem., 1999, 36, 321-332.
K. Morimoto et al., "Synthesis of Halosulfuron-methyl via Selective Chlorination at 3- and/or 5-Position of Pyrazole-4-carboxylates" J. Heterocycl. Chem., 1997, 34, 537-540.
K. Washizuka et al., "Novel generation of azomethine imines from alpha-silylnitrosamines by 1,4-silatropic shift and their cycloaddition" Tetrahedron Lett., 1999, 40, 8849-8853.
Khandoga et al, "The Plaque Lipid Lysophosphatidic Acid Stimulates Platelets Not Through the LPA1, LPA2 and LPA3 Receptor" J Thromb Haemost (2007), 5 Supplement 2, P-M-246, pp. 1-2.
Khandoga et al., "Lysophosphatidic acid-induced platelet shape change revealed through LPA1-5 receptor-selective probes and albumin" Platelets (2008), 19, 415-427.
Kinloch et al., "New targets for neuropathic pain therapeutics" Expert Opin Ther Targets (2005), 9, 685-698.
Kovanen et al, "Infiltrates of Activated Mast Cells at the Site of Coronary Atheromatous Erosion or Rupture in Myocardial Infarction" Circulation (1995), 92, 1084-1088.
Leighton, "The Formation of Hydrazides by the Action of Phenylhydrazine Upon Organic Acids in the Cold" American chemical Journal (1898) 20, 676-679.
Lundequist, "Synergistic Induction of IL-23 Expression in Fibroblast-like Synoviocytes by IL-17 and TNF-Alpha: A Positive Feedback Loop in Rheumatoid Arthritis" J Allergy Clin Immunol (2008), 121, Suppl 1, Abstr 518, p. 1.
M. A. Martins et al., "One-Pot Synthesis of 3(5)-Ethoxycarbonylpyrazoles" Synthesis 1995, 1491-1492.
M. Elnagdi et al, "Recent Developments in the Synthesis of Pyrazole Derivatives" Heterocycles, 1985, 23, 3121-3153.
M. Martins et al., "1,1,1-Trichloro-4,4-diethoxy-3-buten-2-one and its Trichloroacetylacetate Derivatives: Synthesis and Applications in Regiospecific Preparation of Azoles" Synthesis 2003, 15, 2353-2357.
M. R. Grimmett et al, "Synthesis and Reactions of Lithiated Monocyclic Azoles Containing Two or More Hetero-Atoms. Part III: Pyrazolesi" Heterocycles, 1994, 37, 2087-2147.
M. R. Netherton et al, "Palladium-Catalyzed Cross-Coupling Reactions of Unactivated Alkyl Electrophiles with Organometallic Compounds" Topics in Organometallic Chemistry 2005, 14 p. 85-108.
M. Rodriguez-Franco et al., "A mild and efficient method for the regioselective iodination of pyrazoles" Tetrahedron Lett. 2001, 42, 863-865.
N. Kudo et al., "Synthesis and Herbicidal Activity of 1,5-Diarylpyrazole Derivatives" Chem. Pharm Bull., 1999, 47, 857-868.
Noguchi et al., "Identification of p2y9/GPR23 as a Novel G Protein-coupled Receptor for Lysophosphatidic Acid, Structurally Distant from the Edg Family" J Biol Chem (2003), 278, 25600-25606.
Norby K., "Mast cells and angiogenesis" APMIS, 2002, 110, 355-371.
O. Mitsunobu, "The Use of Diethyl Azodicarboxylate and Triphenylphosphine in Synthesis and Transformation of Natural Products" Synthesis, 1981, 1-28.
Oh et al., "Identification of Farnesyl Pyrophosphate and N-Arachidonylglycine as Endogenous Ligands for GPR92" J Biol Chem (2008), 283, 21054-21064.
P. Bravo et al., "An Efficient Entry to Perfluoroalkyl Substituted Azoles Starting from p-Perfluoroalkyl-p-dicarbonyl Compounds" Tetrahedron 1994, 50, 8827-8836.
P. Lam et al., "New Aryl/Heteroaryl C—N Bond Cross-coupling Reactions via Arylboronic Acid/Cupric Acetate Arylation" Tetrahedron Lett., 1998, 39, 2941-2944.

(56) References Cited

OTHER PUBLICATIONS

Q. Chen et al. "Methyl Chlorodifluoroacetate a Convenient Trifluoromethylating Agent" Tetrahedron Lett. 1991, 32, 7689-7690.
R. G. Jones et al. "vic-Dicarboxylic Acid Derivatives of Pyrazole, Isoxazole, and Pyrimidine" J. Org. Chem., 1995, 20, 1342-1347.
R. Huisgen et al., "Diazocarbonyl Compounds and 1-Diethylaminopropyne" J. Am. Chem. Soc., 1979, 101, 3647-3648.
R. Storer et al, "The Synthesis and Antiviral Activity of 4-Fluor0-1-Beta-Dribofuranosyl-1H-Pyrazole-3-Carboxamide" Nucleosides & Nucleotides 1999, 18, 203-216.
Rother et al., "Subtype-Selective Antagonists of Lysophosphatidic Acid Receptors Inhibit Platelet Activation Triggered by the Lipid Core of Atherosclerotic Plaques" Circulation 2003, 108, 741-747.
S. Buchwald et al., "A General and Efficient Copper Catalyst for the Amidation of Aryl Halides and the N-Arylation of Nitrogen Heterocycles" J. Am. Chem. Soc. 2001, 123, 7727-7729.
S. Buchwald et al., "Copper-Catalyzed Coupling of Alkylamines and Aryl Iodides: An Efficient System Even in an Air Atmosphere" Organic Lett. 2002, 4, 581-584.
S. Kang et al. "Copper-catalyzed N-Arylation of Aryl Iodides with Benzamides or Nitrogen Heterocycles in the Presence of Ethylenediamine" Synlett 2002, 3, 427-430.
Self, C.R. et al., "Romazarit: A Potential Disease-Modifying Antirheumatic Drug" Journal of Medicinal Chemistry 1991, 34, 772-777.
Simon et al., "Human Platelet Aggregation Induced by 1-Alkyl-Lysophosphatidic Acid and Its Analogs : A New Group of Phospholipid Mediators ?" Biochem Biophys Res Commun (1982), 108, 1743-1750.
Smith et al, "Mast Cell Deficiency Attenuates Atherosclerosis in Apolipoprotein E-deficient mice" FASEB J (2008), 22, 1065.32.
Sun et al., "Mast cells promote atherosclerosis by releasing proinflammatory cytokines" Nat Med 2007, 13, 719-724.
T. Fuchikami et al. "A Novel and Convenient Method for Trifluoromethylation of Organic Halides Using CF3SiR'3/KF/Cu(I) System" Tetrahedron Lett. 1991, 32, 91-94.
T. Haque et al., "Parallel Synthesis of Potent, Pyrazole-Based Inhibitors of Helicobacter pylori Dihydroorotate Dehydrogenase" J. Med. Chem., 2002, 4669-4678.
T. Nagai et al., "Recent Progress in the Preparation and Synthetic Uses of the Reactions of 3H-Pyrazoles. A Review" Org. Prep. and Proced. Int.; vol. 25, No. 4; 1993, S. 403-435.
T. Sakamoto et al., "Palladium-catalyzed cyanation of aryl and heteroaryl iodides with copper(I) cyanide" J. Chem. Soc. Perkin Trans I, 1999, 2323-2326.
T. Umemoto et al., "Power and Structure-Variable Fluorinating Agents. The N-Fluoropyridinium Salt System" J. Am. Chem. Soc. 1990, 112, 8563.
European Search Report for European Patent Application No. EP 12 30 5552 dated Jul. 13, 2012 (mailed Jul. 26, 2012) p. 1-13.
Database Excerpts from European Search Report for European Patent Application No. EP 12 30 5552 dated Jul. 13, 2012 (mailed Jul. 26, 2012) p. 1-10.
The United States Department of Justice, "Former Research Chemist at Global Pharmaceutical Company Sentenced to 18 Months in Prison for Theft of Trade Secrets" The United States Attorney's Office, District of New Jersey, http://www.justice.gov/usao/nj/Press/files/Li,%20Yuan%20Sentencing%20News%20Release.html, pp. 1-2 (May 7, 2012).
Toews et al., "Lysophosphatidic acid in airway function and disease" Biochim Biophys Acta (2002), 1582, 240-250.
Tokumura et al., "Human platelets respond differentially to lysophosphatidic acids having a highly unsaturated fatty acyl group and alkyl ether-linked lysophosphatidic acids" Biochem J (2002), 365, 617-628.
V. D. Gardner et al., "A Versatile Approach to Analogues of the Cannabinoid-like Anti-emetic Nonabine (BRL 4664)" J. Heterocycl. Chem., 1984, 21, 121-127.

Van Meeteren et al., "Autotaxin, a Secreted Lysophospholipase D, Is Essential for Blood Vessel Formation during Development" Mol Cell Biol (2006), 26, 5015-5022.
W. Holzer et al., "N1-Substituted 3,5-Dimethoxy-4-halogeno-1H-pyrazoles: Synthesis and NMR Study" J. Heterocycl. Chem., 1995, 32, 1351-1354.
W. Sucrow et al., "Phthaloyl Peroxide as an Efficient Source of Singlet Oxygen" Angew. Chem., Int. Ed., 1975, 14, 560-561.
W.T. Ashton, "A Regioselective Route to 3-Alkyl-1-aryl-IH-pyrazole-5-carboxylates: Synthetic Studies and Structural Assignments" J. Heterocycl. Chem. 1993, 30, 307-311.
Williams et al., "Lysophosphatidic Acid 2 Receptor-mediated Supramolecular ComplexFormation Regulates Its Antiapoptotic Effect" J Biol Chem (2009), 284, 14558-14571.
Wong, P.C. et al., "Nonpeptide Factor Xa Inhibitors: DPC423, A Highly Potent and Orally Bioavailable Pyrazole Antithrombotic Agent" Cardiovas. Drug Rev. 2002, vol. 20, No. 2, pp. 137-152.
Y. Huang et al., "Regioselective Synthesis of 1,3,5-Triaryl-4-alkylpyrazoles: Novel Ligands for the Estrogen Receptor" Org Lett, 2000, 2, 2833-2836.
Zuo et al., "Inflammation and hyperalgesia induced by nerve injury in the rat: a key role of mast cells" Pain (2003), 105, 467-479.
Markova, N. K. et al, "Study of the reaction of 1-Dialkamino(alkoxy)-1-buten-3-ones with Some 1,3-Dipolar Systems". Zh. Org. Khim. 1983, 19, 2281-2285.
Nef, J. U. "Ethylic Acetoacetate" Liebigs Ann. Chem. 1893, 276, 200-245.
Hartwig, J., "Transition Metal Catalyzed Synthesis of Arylamines and Aryl Ethers from Aryl Halides and Inflates: Scope and Mechanism" Angew. Chem. Int. Ed. 1998, 37, 2046-2067.
International Search Report for International Patent Application No. PCT/EP2013/060169 dated Jun. 5, 2013 (mailed Jul. 31, 2013) pp. 1-10.
G. Auzzi et al. "Alogenazione Di Alcuni Derivati Pirazolo [1,5-a] Pirimidinici" Farmaco, Ed Sci, 1979, 34 743-750.
J. Barluenga et al., "A New Class of Fused 1,4-Diazepines: Synthesis of Substituted 8,8a-Dihydrofuro[2,3-b][1,4] diazepin-2-ones" J. Chem. Soc., Chem. Commun., 1991, 353-354.
E. M. Beccalli "Isothiazoles. Part 11: 3-Azahexatrienes from 2-Arylpropenamidines: Electrocyclization to 6-Aminonicotinic Acid Derivatives" et al., Tetrahedron, 2000, 56, 4817-4821.
D. L. Boger "Deils-Alder Reactions of Azadienes" Tetrahedron, 1983, 39, 2869-2939.
B. Burg et al "Reaktionen Sechsgliedriger Heterocyclen MIT Ketenacetalen" Tetrahedron Lett. 1975, 16, 2897-2900.
J. Sauer et al., "Ethynyltributyltin—a Synthetic Equivalent for Acetylene, Aryi, Acyl and Halogeno Alkynes in [4+2] Cycloadditions" Tetrahedron Lett., 1998, 39, 2549-2552.
J. Satyanarayana et al., "Cyclocondensation of a-Oxoketene N,S-Acetals with B-Lithioamino-B-Substituted Acrylonitriles: A Facile Route to 2,6-Substituted 4-Amino-3-cyanopyridines" Synthesis, 1991, 889-890.
E. Profft et al., "N-Oxyde substituierter Picolinsauren" J. Prakt. Chem., 1961, 13, 58-75.
J. Epsztajn et al., "Application of Organolithium and Related Reagents in Synthesis. Part 7. Synthesis and Metallation of 4-Methoxypicolin- and 2-Methoxyisonicotinanilioes. A Useful Method for Preparation of 2,3,4-Trisuestituted Pyridines" Tetrahedron, 1989, 45, 7469-7476.
A. K Gupta et al., "Cyclocondensation of a-Oxoketene Dithioacetals With B-Lithioamino-B-Substituted Acrylonitriles:Synthesis of 2,6-Substituted and 5,6-Annelated 3-Cyano-4-(t4BTRYLTHIO)Pyridines" Tetrahedron, 1990, 46, 3703-3714.
B. Haag-Zeino et al. "Funktionell substituierte Pyridine durch Hetero-Diels-Alder-Reaktion mit inversem Elektronenbedarf" Chem. Ber., 1987, 120, 1505-1509.
K. Heyns et al., "Uber y-Pyrone und y-Pyridone, 11. Mitteill: Darstellung und Eigenschatfen einiger substituierter y-Pyridone" Chem. Ber., 1954, 87, 1377-1384.
S.-T. Huang et al., "Total Synthesis of Endothelin-Converting Enzyme Antagonist WS75624 B" Tetrahedron Lett., 1998, 39, 9335-9338.

(56) References Cited

OTHER PUBLICATIONS

Ilic et al, "Thrombin inhibitors with lipid peroxidation and lipoxygenase inhibitory activities" Bioorganic & Medicinal Chemistry Letters, vol. 21, 16, 2011, pp. 4705-4709.

M. A. Massa et al., "Synthesis of Novel Substituted Pyridines As Inhibitors of Endothelin Converting Enzyme-1 (ECE-1)" Bioorg. Med. Chem. Lett., 1998, 8, 2117-2122.

F. Palacios et al., "Cycloaddition Reactions of Neutral 2-Azadienes with Enamines—Regiospecific Synthesis of Highly Substituted Dihydropyridines and Pyridines" Eur. J. Org. Chem., 2001, 2115-2122.

W.C. Patt et al., "The Total Synthesis of the Natural Product Endothelin Converting Enzyme (ECE) Inhibitor, WS75624 B" Tetrahedron Lett., 1997, 38, 1297-1300.

S. Piyamongkol et al., "Novel Synthetic Approach to 2-(1'-hydroxyalkyl)- and 2-amido-3-hydroxypyridin-4-ones" Tetrahedron, 2001, 57, 3479-3486.

Pohl et al, "Nucleophilic Substitution in a Series of 4-Nitronicotinic Acid 1-Oxide Derivatives" Collect.Czech.Chem.Commun, 1995,90, 1170-1177.

Markova et al, Zh. Org. Khim. 1983, 19, 2281-2285.

Nef, J.U. Liebigs Ann. Chem. 1893, 276, 200-245.

Hartwig, J., Angew. Chem. Int. Ed. 1998, 37, 2046-2067.

* cited by examiner

PYRAZOLE DERIVATIVES AND THEIR USE AS LPAR5 ANTAGONISTS

This application is a national stage application under 35 U.S.C. §371 of International Application No. PCT/EP2013/060171, filed May 16, 2013, which claims priority of European Application No. 12305552.7 filed on May 18, 2012, the disclosure of which is explicitly incorporated by reference herein.

The present invention relates to pyrazole derivatives of the formula I,

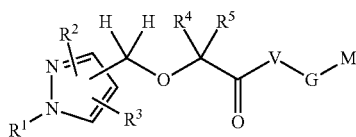

wherein the residues $R^1$ to $R^5$, V, G and M have the meanings indicated below. The compounds of the formula I are valuable pharmacologically active compounds for use in the treatment of diverse disorders. Compounds of the formula I exhibit a strong anti-aggregating effect on platelets and thus an anti-thrombotic effect and are suitable, for example, for the therapy and prophylaxis of cardiovascular disorders like thromboembolic diseases or restenoses. In addition, compounds of the formula I inhibit LPA-mediated activation of mast cells and microglia cells. The compounds of the invention are antagonists of the platelet LPA receptor LPAR5 (GPR92) and can in general be applied in conditions in which an undesired activation of the platelet LPA receptor LPAR5, the mast cell LPA receptor LPAR5 or the microglia cell LPA receptor LPAR5 is present or for the cure or prevention of which an inhibition of the platelet, mast cell or microglia cell LPA receptor LPAR5 is intended. The invention furthermore relates to processes for the preparation of compounds of the formula I, their use, in particular as active ingredients in medicaments, and pharmaceutical compositions comprising them.

In the industrialized world thrombotic complications are one of the major causes of death. Examples of conditions associated with pathological thrombus formation include deep vein thrombosis, venous and arterial thromboembolism, thrombophlebitis, coronary and cerebral arterial thrombosis, cerebral embolism, renal embolism, pulmonary embolism, disseminated intravascular coagulation, transient ischemic attacks, strokes, acute myocardial infarction, unstable angina, chronic stable angina, peripheral vascular disease, preeclampsia/eclampsia, and thrombotic cytopenic purpura. Also during or following invasive procedures, including insertion of endovascular devices and protheses, carotid endarterectomy, angioplasty, CABG (coronary artery bypass graft) surgery, vascular graft surgery, and stent placements, thrombotic and restenotic complications could occur.

Platelet aggregation plays a critical role in these intravascular thrombotic events. Platelets can be activated by mediators released from circulating cells and damaged endothelial cells lining the vessel or by exposed subendothelial matrix molecules such as collagen, lysophosphatidic acid or by thrombin, which is formed in the coagulation cascade. Following activation, platelets, which normally circulate freely in the vasculature, and other cells, accumulate at the site of a vessel injury to form a thrombus and recruit more platelets to the developing thrombus. During this process, thrombi can grow to a sufficient size to partly or completely block arterial blood vessels. In veins thrombi can also form in areas of stasis or slow blood flow. These venous thrombi can create emboli that travel through the circulatory system, as they easily detach portions of themselves. These traveling emboli can block other vessels, such as pulmonary or coronary arteries, which can result in the above-mentioned pathological outcomes such as pulmonary or coronary embolism. In summary, for venous thrombi, morbidity and mortality arise primarily after embolization or distant blockade of vessels, whereas arterial thrombi cause serious pathological conditions by local blockade.

Lysophosphatidic acid (LPA) is an important bioactive phospholipid with a wide range of cellular functions. Levels of LPA are tightly regulated via its synthesis, controlled by two different pathways. The first consisting of phospholipase D (PLD) and phospholipase A2 ($PLA_2$) activity, the second consisting of $PLA_2$ and lysophospholipase D (lysoPLD) activity. The most commonly used LPA in laboratory praxis is 18:1 LPA (1-acyl-2-hydroxy-sn-glycero-3-phosphate). However, many other forms of LPA exist in the organism, with varying length of the fatty acid chain, different saturation grades and coupling of the fatty acid chain to the glycerol backbone, i.e. coupling via an ester or ether bond (Choi et al., Ann Rev Pharmacol Toxicol (2010), 50, 157-186). A key enzyme for LPA synthesis is autotaxin (ATX), Enpp2 in mice. It has been shown that ATX has lysoPLD activity and that $Enpp2^{-/-}$ mice die in utero at day 9.5. $Enpp2^{+/-}$ mice show reduced LPA plasma levels (van Meeteren et al., Mol Cell Biol (2006), 26, 5015-5022). LPA exerts its extracellular biological effects through binding to G protein-coupled receptors. So far, five different LPA receptors have been identified, LPAR1 (EDG2), LPAR2 (EDG4), LPAR3 (EDG7), LPAR4 (GPR23 and LPAR5 (GPR92). All described LPA receptors belong to the class A (Rhodopsin-like class) of G protein-coupled receptors (GPCRs).

LPAR5 has been identified in mouse and human dorsal root ganglia and reduced perception of pain was seen in $LPAR5^{-/-}$ mice (Oh et al., J Biol Chem (2008), 283, 21054-21064; Kinloch et al., Expert Opin Ther Targets (2005), 9, 685-698). The coupling of LPARs to different G protein subunits in different cell types in concert with the differential expression of the various LPA receptors on the same cell is the primary reason for the great variety of biological effects of LPA. The influence of LPA on the activation of human platelets has been described in the early 1980s. 1-O-alkyl-sn-glycero-3-phosphate (an alkyl-LPA) has been identified to be a more potent activator in platelets compared to oleoyl-LPA (Simon et al., Biochem Biophys Res Commun (1982), 108, 1743-1750). Further studies pointed out that the so-called alkyl-LPA receptor is neither an EDG-type LPA receptor nor GPR23 (Tokumura et al., Biochem J (2002), 365, 617-628; Noguchi et al., J Biol Chem (2003), 278, 25600-25606; Khandoga et al., J Thromb Haemost (2007), 5 Supplement 2: P-M-246 (ISTH 2007)). When transiently expressed in the rat hepatoma cell line RH7777, LPAR5 can be activated more strongly with alkyl-LPA than acyl-LPA (Williams et al., J Biol Chem (2009), 284, 14558-14571). These data were in line with the LPA-mediated activation observed for human blood platelets, in which the functional effect of alkyl-LPA, in terms of inducing platelet aggregation is more pronounced than the effect of acyl-LPA. In addition, the LPA-receptors LPAR4 and LPAR5 are highly expressed by human platelets (Amisten et al., Thromb Res (2008), 122, 47-57). In contrast to LPAR5, which is coupled to $G_q$, LPAR4 couples to $G_s$ and can therefore be excluded to participate in LPA-mediated activation of human platelets. Consequently, LPAR5 was discussed to be the central LPA-receptor responsible for LPA-mediated activation in human platelets (Khandoga et al., Platelets (2008), 19, 415-427). High expression of LPAR5 in human mast cell lines has been demonstrated, for example by Lundequist (Lundequist, J Allergy Clin Immunol (2008), 121, Suppl 1, Abstr 518), and further analyses.

Mast cells are part of the immune system and generated as precursor cells in the bone marrow, differentiating to mature mast cells in the homing tissue. Mast cells participate in a variety of pathophysiological processes that range from antimicrobial defense to anaphylaxis and inflammatory arthritis and have thus been discussed to be related to allergic responses. When activated, mast cells degranulate and release a plethora of mediators (cytokines such as TNFa, MCP-1, Rantes) into the interstitium. This indicates a direct contribution of mast cells to neuropathic pain by releasing algogenic mediators after degranulation.

Atherosclerosis is promoted by mast cells not only through the release of proinflammatory cytokines, mast cell deficiency attenuates atherosclerosis in apolipoprotein E-deficient mice and infiltrates of activated mast cells can be observed at the site of coronary atheromatous erosion or rupture in myocardial infarction (Sun et al., Nat Med (2007), 13, 719-724; Smith et al., FASEB J (2008), 22, 1065.32; Kovanen et al., Circulation (1995), 92, 1084-1088). These data provide sound evidence for the central role of mast cells in the development and progression of atherosclerotic plaques. In the atherosclerotic plaque mast cells contribute to plaque growth and instability via release of stored and newly synthesized mediators such as (a) inflammatory cytokines that lead to an increased invasion of monocytes and their differentiation to macrophages, (b) angiogenic cytokines such as VEGF that might induce angiogenesis in the plaque, with intraplaque hemorrhage leading to an increased risk of plaque rupture and (c) histamine, a vasoactive component known to enhance vascular permeability with the potential risk of increased LDL influx available for foam cell formation. Although the absolute number of mast cells in atherosclerotic plaques is inferior to the number of other inflammatory cells in the same region, LPA as a direct activating ligand of mast cells is present at high concentrations in atherosclerotic plaques (Rother et al., Circulation (2003), 108, 741-747).

Apart from the above discussed role of mast cells in atherosclerosis, the broad spectrum of mast cell functions explains why mast cells are involved in a variety of pathologies apart from allergic responses related to pathologies with an inflammatory component. These diseases comprise hyperalgesia, asthma, multiple sclerosis and angiogenesis to name only a few (Zuo et al., Pain (2003), 105, 467-479; Toews et al., Biochim Biophys Acta (2002), 1582, 240-250; Norby, APMIS (2002), 110, 355-371). Treatment of the human mast cell line LAD2 with a short hairpin RNA targeting LPAR5 down-regulates LPAR5 expression and attenuates MIP-1β following LPA activation (Lundequist, J Allergy Clin Immunol (2008), 121, Suppl 1, Abstr 518).

Analyses of the LPA receptor profile in the murine microglia cell line BV-2, confirmed a high expression of LPAR5 in microglia cells, which are like mast cells a cell population of the inflammatory system. The finding that LPAR5 is highly expressed not only in mast cells but as well in microglia cells underlines the central role of LPAR5 in the development and progression of inflammatory disorders, such as hyperalgesia, asthma, multiple sclerosis, angiogenesis and others.

Further experiments confirmed that in human platelets and in human mast cells and microglia cells LPAR5 is the key LPA-receptor responsible for LPA-mediated activation. In view of the relevance of LPAR5 for various disease states there is a need for compounds which efficiently inhibit LPAR5 and, for example, consequently inhibit mast cell activation, for example in atherosclerotic plaques, or platelet activation in pathological settings, and allow novel therapeutic options for treating disorders. Thus, it is an object of the present invention to provide LPAR5 antagonists, which antagonize the effect of endogenous LPA on its LPAR5 receptor and which have further advantageous properties, for instance stability in plasma and liver and selectivity versus other receptors whose agonism or antagonism is not intended. This object is achieved in accordance with the invention by providing the pyrazole derivatives of the formula I, which exhibit excellent LPAR5 antagonistic activity and are favorable agents with high bioavailability, and can be used for inhibiting platelet aggregation and treating thromboembolic diseases, for example.

Further WO 2011/015501, WO 2009/109613, WO 2009/109616, WO 2009/109618 and EP 0382276 describe specific 1-benzyl-indazole derivatives for the treatment of diseases based on the expression of MCP-1, CX3CR1 and p40. GuoGang Tu et al, Journal of Enzyme Inhibition and Medicinal Chemistry, 2011, 26(2), 222-230 describe some compounds derived from the 1,5-diarylpyrazole scaffold with potency towards the inhibition of the CB1 receptor. Self C. R. et al, Journal of Medicinal Chemistry, 1991, 34, 772-777 disclose potential disease-modifying antirheumatic drugs including specific 1-phenyl-pyrazole derivatives.

A subject of the present invention are the compounds of the formula I, in any of their stereoisomeric forms or a mixture of stereoisomeric forms in any ratio, and the pharmaceutically acceptable salt thereof,

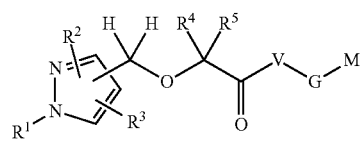

I wherein

R$^1$ is selected from the series consisting of hydrogen, (C$_1$-C$_6$)-alkyl, (C$_3$-C$_7$)-cycloalkyl, (C$_3$-C$_7$)-cycloalkyl-(C$_1$-C$_4$)-alkyl-, Ar and Ar—(C$_1$-C$_4$)-alkyl-;

R$^2$ and R$^3$ are independently of each other selected from the series consisting of hydrogen, halogen, (C$_1$-C$_4$)-alkyl, (C$_3$-C$_7$)-cycloalkyl, (C$_3$-C$_7$)-cycloalkyl-(C$_1$-C$_4$)-alkyl-, Ar, Ar—(C$_1$-C$_4$)-alkyl-, (C$_1$-C$_4$)-alkyl-O—, (C$_3$-C$_7$)-cycloalkyl-O—, (C$_3$-C$_7$)-cycloalkyl-(C$_1$-C$_4$)-alkyl-O—, Ar—O— and Ar—(C$_1$-C$_4$)-alkyl-O—, R$^4$ and R$^5$ are independently of each other selected from the series consisting of hydrogen, fluorine and (C$_1$-C$_6$)-alkyl, or the groups R$^4$ and R$^5$ together with the carbon atom carrying them form a (C$_3$-C$_7$)-cycloalkane ring which is unsubstituted or substituted by one or more identical or different substituents selected from the series consisting of fluorine and (C$_1$-C$_4$)-alkyl;

R$^{11}$, R$^{12}$, R$^{13}$ and R$^{14}$ are independently of each other selected from the series consisting of hydrogen and (C$_1$-C$_4$)-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1\text{-}C_4)$-alkyl, $(C_3\text{-}C_7)$-cycloalkyl, $(C_3\text{-}C_7)$-cycloalkyl-$(C_1\text{-}C_4)$-alkyl-, cyano and $(C_1\text{-}C_4)$-alkyl-O—;

V is selected from the series consisting of $R^{12}$—$N(R^{13})$—, and in this case G and M are not present, or V is selected from the series consisting of —$N(R^{14})$—, —$N(R^{14})$—$(C_1\text{-}C_4)$-alkyl-, —O— and —O—$(C_1\text{-}C_4)$-alkyl-, and in this case G is selected from the series consisting of a direct bond and phenylene which is unsubstituted or substituted by one or more identical or different substituents selected from the series consisting of halogen, $(C_1\text{-}C_4)$-alkyl, cyano and $(C_1\text{-}C_4)$-alkyl-O—, provided that G is not a direct bond if V is —$N(R^{14})$— or —O—, and M is selected from the series consisting of $R^{11}$—O—$C(O)$— and $R^{12}$—$N(R^{13})$—$C(O)$—;

wherein all alkyl groups are unsubstituted or substituted by one or more fluorine substituents, and all cycloalkyl groups are unsubstituted or substituted by one or more identical or different substituents selected from the series consisting of fluorine and $(C_1\text{-}C_4)$-alkyl.

In one embodiment the present invention relates to compounds of the formula I, wherein $R^1$ is selected from the series consisting of hydrogen, $(C_1\text{-}C_6)$-alkyl, $(C_3\text{-}C_7)$-cycloalkyl, Ar and Ar—$(C_1\text{-}C_4)$-alkyl-;

$R^2$ and $R^3$ are independently of each other selected from the series consisting of hydrogen, $(C_1\text{-}C_4)$-alkyl, $(C_3\text{-}C_7)$-cycloalkyl, $(C_3\text{-}C_7)$-cycloalkyl-$(C_1\text{-}C_4)$-alkyl-, Ar, Ar—$(C_1\text{-}C_4)$-alkyl-, $(C_1\text{-}C_4)$-alkyl-O—, $(C_3\text{-}C_7)$-cycloalkyl-O—, $(C_3\text{-}C_7)$-cycloalkyl-$(C_1\text{-}C_4)$-alkyl-O—, Ar—O— and Ar—$(C_1\text{-}C_4)$-alkyl-O—, $R^4$ and $R^5$ are independently of each other selected from the series consisting of hydrogen and $(C_1\text{-}C_6)$-alkyl, or the groups $R^4$ and $R^5$ together with the carbon atom carrying them form a $(C_3\text{-}C_7)$-cycloalkane ring which is unsubstituted or substituted by one or more identical or different substituents selected from the series consisting of fluorine and $(C_1\text{-}C_4)$-alkyl;

$R^{11}$, $R^{12}$, $R^{13}$ and $R^{14}$ are independently of each other selected from the series consisting of hydrogen and $(C_1\text{-}C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1\text{-}C_4)$-alkyl, $(C_3\text{-}C_7)$-cycloalkyl, $(C_3\text{-}C_7)$-cycloalkyl-$(C_1\text{-}C_4)$-alkyl-, cyano and $(C_1\text{-}C_4)$-alkyl-O—;

V is selected from the series consisting of —$N(R^{14})$—, —$N(R^{14})$—$(C_1\text{-}C_4)$-alkyl- and —O—$(C_1\text{-}C_4)$-alkyl-, and G is selected from the series consisting of a direct bond and phenylene which is unsubstituted or substituted by one or more identical or different substituents selected from the series consisting of halogen, $(C_1\text{-}C_4)$-alkyl, cyano and $(C_1\text{-}C_4)$-alkyl-O—, provided that G is not a direct bond if V is —$N(R^{14})$—, and M is selected from the series consisting of $R^{11}$—O—$C(O)$— and $R^{12}$—$N(R^{13})$—$C(O)$—;

wherein all alkyl groups are unsubstituted or substituted by one or more fluorine substituents, and all cycloalkyl groups are unsubstituted or substituted by one or more identical or different substituents selected from the series consisting of fluorine and $(C_1\text{-}C_4)$-alkyl;

and all stereoisomeric forms and mixtures of stereoisomeric forms in any ratio, and the pharmaceutically acceptable salts thereof.

In another embodiment the present invention relates to compounds of the formula I, wherein $R^1$ is selected from the series consisting of $(C_1\text{-}C_6)$-alkyl, $(C_3\text{-}C_7)$-cycloalkyl, Ar and Ar—$(C_1\text{-}C_4)$-alkyl-;

$R^2$ and $R^3$ are independently of each other selected from the series consisting of hydrogen, $(C_1\text{-}C_4)$-alkyl, Ar, Ar—$(C_1\text{-}C_4)$-alkyl-, $(C_1\text{-}C_4)$-alkyl-O—, $(C_3\text{-}C_7)$-cycloalkyl-O—, Ar—O— and Ar—$(C_1\text{-}C_4)$-alkyl-O—, $R^4$ and $R^5$ are independently of each other selected from the series consisting of hydrogen and $(C_1\text{-}C_6)$-alkyl, or the groups $R^4$ and $R^5$ together with the carbon atom carrying them form a $(C_3\text{-}C_7)$-cycloalkane ring which is unsubstituted or substituted by one or more identical or different substituents selected from the series consisting of fluorine and $(C_1\text{-}C_4)$-alkyl;

$R^{11}$, $R^{12}$, $R^{13}$ and $R^{14}$ are independently of each other selected from the series consisting of hydrogen and $(C_1\text{-}C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1\text{-}C_4)$-alkyl, $(C_3\text{-}C_7)$-cycloalkyl and $(C_1\text{-}C_4)$-alkyl-O—;

V is selected from the series consisting of —$N(R^{14})$— and —$N(R^{14})$—$(C_1\text{-}C_4)$-alkyl-, and G is selected from the series consisting of a direct bond and phenylene which is unsubstituted or substituted by one or more identical or different substituents selected from the series consisting of halogen, $(C_1\text{-}C_4)$-alkyl and $(C_1\text{-}C_4)$-alkyl-O—, provided that G is not a direct bond if V is —$N(R^{14})$—, and M is selected from the series consisting of $R^{11}$—O—$C(O)$— and $R^{12}$—$N(R^{13})$—$C(O)$—;

wherein all alkyl groups are unsubstituted or substituted by one or more fluorine substituents, and all cycloalkyl groups are unsubstituted or substituted by one or more identical or different substituents selected from the series consisting of fluorine and $(C_1\text{-}C_4)$-alkyl;

and all stereoisomeric forms and mixtures of stereoisomeric form in any ratio, and the pharmaceutically acceptable salts thereof.

In another embodiment the present invention relates to compounds of the formula I, wherein $R^1$ is selected from the series consisting of $(C_1\text{-}C_4)$-alkyl, Ar and Ar—$(C_1\text{-}C_4)$-alkyl-;

$R^2$ and $R^3$ are independently of each other selected from the series consisting of hydrogen, $(C_1\text{-}C_4)$-alkyl, Ar, Ar—$(C_1\text{-}C_4)$-alkyl-, and Ar—O—, $R^4$ and $R^5$ are independently of each other selected from the series consisting of hydrogen and $(C_1\text{-}C_6)$-alkyl, or the groups $R^4$ and $R^5$ together with the carbon atom carrying them form a $(C_3\text{-}C_7)$-cycloalkane ring which is unsubstituted or substituted by one or more identical or different substituents selected from the series consisting of fluorine and $(C_1\text{-}C_4)$-alkyl;

$R^{11}$ and $R^{14}$ are independently of each other selected from the series consisting of hydrogen and $(C_1\text{-}C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1-C_4)$-alkyl, $(C_3-C_7)$-cycloalkyl and $(C_1-C_4)$-alkyl-O—;

V is selected from the series consisting of —$N(R^{14})$— and —$N(R^{14})$—$(C_1-C_4)$-alkyl-, and G is selected from the series consisting of a direct bond and phenylene which is unsubstituted or substituted by one or more identical or different substituents selected from the series consisting of halogen, $(C_1-C_4)$-alkyl and $(C_1-C_4)$-alkyl-O—, provided that G is not a direct bond if V is —$N(R^{14})$, and M is $R^{11}$—O—C(O)—;

wherein all alkyl groups are unsubstituted or substituted by one or more fluorine substituents, and all cycloalkyl groups are unsubstituted or substituted by one or more identical or different substituents selected from the series consisting of fluorine and $(C_1-C_4)$-alkyl;

and all stereoisomeric forms and mixtures of stereoisomeric forms in any ratio, and the pharmaceutically acceptable salts thereof.

In another embodiment the present invention relates to compounds of the formula I, wherein $R^1$ is selected from the series consisting of $(C_1-C_4)$-alkyl, Ar and Ar—$(C_1-C_4)$-alkyl-;

$R^2$ and $R^3$ are independently of each other selected from the series consisting of hydrogen, $(C_1-C_4)$-alkyl, Ar— and Ar—O—, $R^4$ and $R^5$ are independently of each other selected from the series consisting of hydrogen and $(C_1-C_6)$-alkyl, or the groups $R^4$ and $R^5$ together with the carbon atom carrying them form a $(C_3-C_7)$-cycloalkane ring which is unsubstituted or substituted by one or more fluorine substituents;

$R^{11}$ and $R^{14}$ are independently of each other selected from the series consisting of hydrogen and $(C_1-C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1-C_4)$-alkyl, $(C_3-C_7)$-cycloalkyl and $(C_1-C_4)$-alkyl-O—;

V is selected from the series consisting of —$N(R^{14})$— and —$N(R^{14})$—$(C_1-C_4)$-alkyl-, and G is selected from the series consisting of a direct bond and phenylene which is unsubstituted or substituted by one or more identical or different substituents selected from the series consisting of halogen, $(C_1-C_4)$-alkyl and $(C_1-C_4)$-alkyl-O—, provided that G is not a direct bond if V is —$N(R^{14})$, and M is $R^{11}$—O—C(O)—;

wherein all alkyl groups are unsubstituted or substituted by one or more fluorine substituents;

and all stereoisomeric forms and mixtures of stereoisomeric forms in any ratio, and the pharmaceutically acceptable salts thereof.

In one embodiment compounds of the formula I are defined as above and $R^1$ is selected from the series consisting of $(C_1-C_6)$-alkyl, $(C_3-C_7)$-cycloalkyl, $(C_3-C_7)$-cycloalkyl-$(C_1-C_4)$-alkyl-, Ar and Ar—$(C_1-C_4)$-alkyl-, in another embodiment from the series consisting of $(C_1-C_6)$-alkyl, Ar and Ar—$(C_1-C_4)$-alkyl-, in another embodiment from the series consisting of $(C_1-C_4)$-alkyl, Ar and Ar—$(C_1-C_4)$-alkyl-, in another embodiment from the series consisting of $(C_1-C_6)$-alkyl and Ar, in another embodiment from the series consisting of $(C_1-C_4)$-alkyl and Ar, in another embodiment from the series consisting of Ar and Ar—$(C_1-C_4)$-alkyl-, in another embodiment $R^1$ is Ar, wherein all Ar groups are unsubstituted or substituted as specified. In one embodiment an Ar—$(C_1-C_4)$-alkyl- group representing $R^1$ is an Ar—$(C_1-C_2)$-alkyl- group, in another embodiment an Ar—$CH_2$— group. In one embodiment a group Ar representing $R^1$ is a phenyl group which is unsubstituted or substituted as specified. In one embodiment, a substituted Ar group or phenyl group representing $R^1$ is substituted by one, two or three, in another embodiment by one or two, in another embodiment by one, identical or different substituents, wherein in one embodiment the substituents are selected from the series consisting of halogen, $(C_1-C_4)$-alkyl, cyano and $(C_1-C_4)$-alkyl-O—, in another embodiment from the series consisting of halogen, $(C_1-C_4)$-alkyl and cyano, in another embodiment from the series consisting of halogen, $(C_1-C_4)$-alkyl and $(C_1-C_4)$-alkyl-O—, in another embodiment from the series consisting of halogen and $(C_1-C_4)$-alkyl, and in another embodiment they are identical or different halogen substituents, for example chlorine.

In one embodiment compounds of the formula I are defined as above and $R^2$ and $R^3$ are independently of each other selected from the series consisting of hydrogen, halogen, $(C_1-C_4)$-alkyl, Ar, Ar—$(C_1-C_4)$-alkyl-, $(C_1-C_4)$-alkyl-O—, Ar—O— and Ar—$(C_1-C_4)$-alkyl-O—, in another embodiment from the series consisting of hydrogen, $(C_1-C_4)$-alkyl, Ar, Ar—$(C_1-C_4)$-alkyl-, $(C_1-C_4)$-alkyl-O—, Ar—O— and Ar—$(C_1-C_4)$-alkyl-O—, in another embodiment from the series consisting of hydrogen, $(C_1-C_4)$-alkyl, Ar, Ar—$(C_1-C_4)$-alkyl- and Ar—O—, in another embodiment from the series consisting of $(C_1-C_4)$-alkyl, Ar, Ar—$(C_1-C_4)$-alkyl- and Ar—O—, in another embodiment from the series consisting of hydrogen, $(C_1-C_4)$-alkyl, Ar and Ar—O—, in another embodiment from the series consisting of $(C_1-C_4)$-alkyl, Ar and Ar—O—, in another embodiment from the series consisting of hydrogen, $(C_1-C_4)$-alkyl and Ar, in another embodiment from the series consisting of $(C_1-C_4)$-alkyl and Ar, wherein all groups Ar occurring in $R^2$ and $R^3$ are unsubstituted or substituted as specified.

In one embodiment, one of the groups $R^2$ and $R^3$ is group Ar or contains a group Ar, and the other of the groups $R^2$ and $R^3$ is selected from the series consisting of hydrogen, $(C_1-C_4)$-alkyl and Ar, in another embodiment from the series consisting of $(C_1-C_4)$-alkyl and Ar, in another embodiment from the series consisting of hydrogen and $(C_1-C_4)$-alkyl. In one embodiment, a group Ar occurring in $R^2$ or $R^3$ is selected from the series consisting of phenyl, naphthyl and an aromatic, 5-membered or 6-membered, monocyclic heterocycle which comprises one ring heteroatom selected from the series consisting of N, O and S, in another embodiment from the series consisting of phenyl and an aromatic, 5-membered or 6-membered, monocyclic heterocycle which comprises one ring heteroatom selected from the series consisting of N, O and S, in another embodiment from the series consisting of phenyl, naphthyl and thienyl, in another embodiment from the series consisting of phenyl and thienyl, in another embodiment from the series consisting of phenyl and naphthyl, and in another embodiment it is a phenyl group, which are all unsubstituted or substituted as specified. In one embodiment, the number of substituents in a substituted group Ar occurring in $R^2$ or $R^3$ is one, two or three, in another embodiment it is one or two, in another embodiment it is one. In one embodiment, the substituents on a substituted group Ar occurring in $R^2$ or $R^3$ are selected from the series consisting of halogen, $(C_1-C_4)$-alkyl, $(C_3-C_7)$-cycloalkyl, cyano and $(C_1-C_4)$-alkyl-O—, in another embodiment from the series consisting of halogen, $(C_1-C_4)$-alkyl, $(C_3-C_7)$-cycloalkyl and $(C_1-C_4)$-alkyl-O—, in another embodiment from the series consisting of halogen and $(C_1-C_4)$-alkyl, wherein $(C_1-C_4)$-alkyl substituents are unsubstituted or substituted by one or more fluorine substituents. In one embodiment, a $(C_1-C_4)$-alkyl substituent present on a group Ar occurring in $R^2$ or $R^3$ is a perfluoroalkyl group, for example a trifluoromethyl group $CF_3$. in one embodiment, halogen substituents present on a group Ar occurring in $R^2$ or $R^3$ are fluorine and/or chlorine substituents.

In one embodiment compounds of the formula I are defined as above and $R^4$ and $R^5$ are independently of each other selected from the series consisting of hydrogen, fluorine and $(C_1-C_4)$-alkyl, in another embodiment from the series consisting of hydrogen and $(C_1-C_4)$-alkyl, in another embodiment from the series consisting of hydrogen and $(C_1-C_3)$-alkyl, in another embodiment from the series consisting of hydrogen, methyl, ethyl, n-propyl and isopropyl, in another embodiment from the series consisting of hydrogen and methyl, and in another embodiment at least one of the groups $R^4$ and $R^5$ is different from hydrogen, or the groups $R^4$ and $R^5$ together with the carbon atom carrying them form a $(C_3-C_7)$-cycloalkane ring, in one embodiment a $(C_4-C_6)$-cycloalkane ring, in another embodiment a $(C_5-C_6)$-cycloalkane ring, which cycloalkane rings are all unsubstituted or substituted as specified.

In another embodiment compounds $R^4$ and $R^5$ are independently of each other selected from the series consisting of hydrogen, fluorine and $(C_1-C_4)$-alkyl, in another embodiment from the series consisting of hydrogen and $(C_1-C_4)$-alkyl, in another embodiment from the series consisting of hydrogen and $(C_1-C_3)$-alkyl, in another embodiment from the series consisting of hydrogen, methyl, ethyl, n-propyl and isopropyl, in another embodiment from the series consisting of hydrogen and methyl.

In one embodiment one of the groups $R^4$ and $R^5$ is hydrogen and the other is as defined, in another embodiment the groups $R^4$ and $R^5$ are both hydrogen, in another embodiment at least one of the groups $R^4$ and $R^5$ is different from hydrogen, in another embodiment the groups $R^4$ and $R^5$ are both $(C_1-C_4)$-alkyl, in another embodiment the groups $R^4$ and $R^5$ are both $(C_1-C_3)$-alkyl, and in another embodiment the groups $R^4$ and $R^5$ are both selected from the series consisting of methyl, ethyl, n-propyl and isopropyl. In one embodiment, the groups $R^4$ and $R^5$ are identical.

In another embodiment $R^4$ and $R^5$ form together with the carbon atom carrying them a $(C_3-C_7)$-cycloalkane ring, in another embodiment a $(C_4-C_6)$-cycloalkane ring, in another embodiment a $(C_5-C_6)$-cycloalkane ring, which cycloalkane rings are all unsubstituted or substituted as specified. In general is the number of substituents in a substituted cycloalkane ring formed by $R^4$ and $R^5$ together with the carbon atom carrying them in one embodiment of the invention one, two, three or four, in another embodiment one, two or three, in another embodiment one or two, and in another embodiment a cycloalkane ring formed by $R^4$ and $R^5$ together with the carbon atom carrying them is unsubstituted.

In one embodiment compounds of the formula I are defined as above and $R^{11}$, $R^{12}$, $R^{13}$ and $R^{14}$ are independently of each other selected from the series consisting of hydrogen, methyl and ethyl, in another embodiment from the series consisting of hydrogen and methyl, and in another embodiment they are hydrogen.

In one embodiment compounds of the formula I are defined as above and Ar is selected from the series consisting of phenyl and naphthyl, in another embodiment from the series consisting of phenyl and an aromatic, 5-membered or 6-membered, monocyclic heterocycle which comprises one or two identical or different ring heteroatoms selected from the series consisting of N, O and S, in another embodiment one ring heteroatom selected from the series consisting of N, O and S, and in another embodiment Ar is phenyl, which are all unsubstituted or substituted by one or more identical or different substituents selected from the series consisting of halogen, $(C_1-C_4)$-alkyl, $(C_3-C_7)$-cycloalkyl, $(C_3-C_7)$-cycloalkyl-$(C_1-C_4)$-alkyl-, cyano and $(C_1-C_4)$-alkyl-O—, in another embodiment from the series consisting of halogen, $(C_1-C_4)$-alkyl, $(C_3-C_7)$-cycloalkyl, cyano and $(C_1-C_4)$-alkyl-O—, in another embodiment from the series consisting of halogen, $(C_1-C_4)$-alkyl, $(C_3-C_7)$-cycloalkyl and $(C_1-C_4)$-alkyl-O—, in another embodiment from the series consisting of halogen, $(C_1-C_4)$-alkyl and $(C_1-C_4)$-alkyl-O—, in another embodiment from the series consisting of halogen, $(C_1-C_4)$-alkyl and $(C_3-C_7)$-cycloalkyl, in another embodiment from the series consisting of halogen and $(C_1-C_4)$-alkyl, wherein alkyl substituents can be unsubstituted or substituted by one or more fluorine substituents. In one embodiment, a substituted group Ar carries one, two or three identical or different substituents, in another embodiment one or two identical or different substituents, in another embodiment one substituent, wherein all groups Ar are independent of each other.

If the divalent group V is the group —$N(R^{14})$—$(C_1-C_4)$-alkyl- or the group —O—$(C_1-C_4)$-alkyl-, the group G is bonded to the $(C_1-C_4)$-alkyl moiety thereof. In one embodiment compounds of the formula I are defined as above and V is selected from the series consisting of —$N(R^{14})$— and —$N(R^{14})$—$(C_1-C_4)$-alkyl-, and in this case G is selected from the series consisting of a direct bond and phenylene, and in another embodiment is phenylene, wherein all phenylene groups are unsubstituted or substituted by one or more identical or different substituents selected from the series consisting of halogen, $(C_1-C_4)$-alkyl, cyano and $(C_1-C_4)$-alkyl-O—, provided that G is not a direct bond if V is —$N(R^{14})$—, and M is $R^{11}$—O—C(O)—, in another embodiment HO—C(O)—.

In another embodiment compounds of the formula I are defined as above and V is selected from the series consisting of $R^{12}$—$N(R^{13})$— and in this case G and M are not present.

In another embodiment, V is selected from the series consisting of —$N(R^{14})$—, —$N(R^{14})$—$(C_1-C_4)$-alkyl-, —O— and —O—$(C_1-C_4)$-alkyl-, in another embodiment from the series consisting of —$N(R^{14})$— and —$N(R^{14})$—$(C_1-C_4)$-alkyl-, in another embodiment from the series consisting of —$N(R^{14})$— and —$N(R^{14})$—$(C_1-C_3)$-alkyl-, and in this case G is selected from the series consisting of a direct bond and phenylene, and in one embodiment is phenylene, wherein all phenylene groups are unsubstituted or substituted as specified, provided that G is not a direct bond if V is —$N(R^{14})$— or —O—, and M is $R^{11}$—O—C(O)— or $R^{12}$—$N(R^{13})$—C(O)—, in another embodiment $R^{11}$—O—C(O)—, in another embodiment HO—C(O)—.

In one embodiment, G is a direct bond, in another embodiment G is phenylene which is unsubstituted or substituted as specified. In one embodiment, a substituted phenylene group representing G carries one or two identical or different substituents, in another embodiment it carries one substituent, which is selected from the series consisting of halogen and $(C_1-C_4)$-alkyl, and in another embodiment is halogen. In one embodiment a phenylene group representing G is unsubstituted. In one embodiment, a phenylene group representing G is selected from the series consisting of 1,3-phenylene and 1,4-phenylene, in another embodiment it is 1,4-phenylene.

The group M-G-V—C(O)—$C(R^4)(R^5)$—O—$CH_2$— in the compounds of the formula I can be bonded to any of the ring carbon atoms of the 1H-pyrazole ring depicted in formula I, i.e. in position 3, in position 4 or in position 5 of the 1H-pyrazole ring, as is symbolized by the free bond on the CH₂ moiety of the said group, which bond is not directed to a specific ring carbon atom. In one embodiment of the invention, the group M-G-V—C(O)—C(R⁴)(R⁵)—O—CH₂— is bonded in position 3 of the pyrazole ring and the compound of the formula I thus is a compound of the formula Ia, in another embodiment the said group is bonded in position 4 of the pyrazole ring and the compound of the formula I thus is a compound of the formula Ib, and in another embodiment the said group is bonded in position 5 of the pyrazole ring and the compound of the formula I thus is a compound of the formula Ic, in another embodiment the said group is bonded in position 3 or position 4, in another embodiment the said group is bonded in position 3 or position 5, and in another embodiment the said group is bonded in position 4 or position 5.

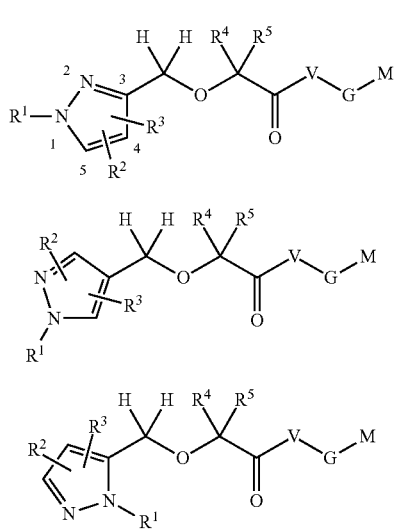

Likewise can the groups R² and R³ in the compounds of the formula I as well as in the compounds of the formulae Ia, Ib and Ic be bonded to any ring carbon atom of the pyrazole ring depicted in formula I which is not occupied by the group M-G-V—C(O)—C(R⁴)(R⁵)—O—CH₂—, i.e. in positions 3 and 4, in positions 3 and 5 or in positions 4 and 5 of the pyrazole ring. The groups R¹ to R⁵, V, G and M in the compounds of the formula Ia, Ib and Ic are defined as in the compounds of the formula I.

In one embodiment of the invention, the compound of the formula I is selected from the series consisting of
4-({2-[5-(4-Chloro-phenyl)-1-(2,4-dichloro-phenyl)-4-methyl-1H-pyrazol-3-ylmethoxy]-2-methyl-propionylamino}-methyl)-benzoic acid,
4-({2-[1-(2,4-Dichloro-phenyl)-4-methyl-5-(4-trifluoromethyl-phenyl)-1H-pyrazol-3-ylmethoxy]-2-methyl-propionylamino}-methyl)-benzoic acid,
4-({2-[5-(4-Chloro-phenyl)-1-(2,4-dichloro-phenyl)-4-methyl-1H-pyrazol-3-ylmethoxy]-acetylamino}-methyl)-benzoic acid,
4-({2-[5-(4-Chloro-phenyl)-1-(2,4-dichloro-phenyl)-4-methyl-1H-pyrazol-3-ylmethoxy]-butyrylamino}-methyl)-benzoic acid,
4-({2-[1-(2-Chloro-phenyl)-4-methyl-5-(4-trifluoromethyl-phenyl)-1H-pyrazol-3-ylmethoxy]-2-methyl-propionylamino}-methyl)-benzoic acid,
4-({2-[1-(4-Chloro-phenyl)-4-methyl-5-(4-trifluoromethyl-phenyl)-1H-pyrazol-3-ylmethoxy]-2-methyl-propionylamino}-methyl)-benzoic acid,
4-({2-[5-(4-Chloro-phenyl)-1-(2,4-dichloro-phenyl)-4-methyl-1H-pyrazol-3-ylmethoxy]-propionylamino}-methyl)-benzoic acid,
4-{2-[1-(2,4-Dichloro-phenyl)-4-methyl-5-(4-trifluoromethyl-phenyl)-1H-pyrazol-3-ylmethoxy]-propionylamino}-benzoic acid,
4-{2-[5-(4-Chloro-phenyl)-1-(2,4-dichloro-phenyl)-4-methyl-1H-pyrazol-3-ylmethoxy]-3-methyl-butyrylamino}-benzoic acid,
4-{2-[1-(4-Chloro-phenyl)-4-methyl-5-(4-trifluoromethyl-phenyl)-1H-pyrazol-3-ylmethoxy]-propionylamino}-benzoic acid,
4-[2-(3-Naphthalen-2-yl-1-phenyl-1H-pyrazol-4-ylmethoxy)-propionylamino]-benzoic acid,
4-{2-[1-(2-Chloro-phenyl)-4-methyl-5-(4-trifluoromethyl-phenyl)-1H-pyrazol-3-ylmethoxy]-propionylamino}-benzoic acid,
4-[2-(3,5-Dimethyl-1-phenyl-1H-pyrazol-4-ylmethoxy)-propionylamino]-benzoic acid,
4-[2-(1,3-Diphenyl-1H-pyrazol-4-ylmethoxy)-propionylamino]-benzoic acid,
4-{2-[1-Benzyl-3-(3-methoxy-phenyl)-1H-pyrazol-4-ylmethoxy]-propionylamino}-benzoic acid,
4-{2-[5-(4-Fluoro-phenoxy)-1-methyl-3-phenyl-1H-pyrazol-4-ylmethoxy]-propionylamino}-benzoic acid,
4-{2-[3-(4-Cyclohexyl-phenyl)-1-phenyl-1H-pyrazol-4-ylmethoxy]-propionylamino}-benzoic acid,
4-[2-(1-Phenyl-3-thiophen-2-yl-1H-pyrazol-4-ylmethoxy)-propionylamino]-benzoic acid, and
4-[2-(1,5-Diphenyl-1H-pyrazol-3-ylmethoxy)-propionylamino]-benzoic acid,
and all stereoisomeric forms and mixtures of stereoisomeric forms in any ratio, and the pharmaceutically acceptable salts thereof.

If structural elements such as groups or substituents, for example alkyl, cycloalkyl or Ar groups, can occur several times in the compounds of the formula I, they are all independent of each other and can in each case have any of the indicated meanings, and they can in each case be identical to or different from any other such element.

The term alkyl is to be understood as meaning a residue of a saturated acyclic hydrocarbon which can be linear, i.e. straight-chain, or branched. If not otherwise defined, alkyl has 1 to 6 carbon atoms or 1 to 4 carbon atoms. Examples of $(C_1-C_6)$-alkyl and $(C_1-C_4)$-alkyl are alkyl residues containing 1, 2, 3, 4, 5 or 6 carbon atoms or 1, 2, 3 or 4 carbon atoms, respectively, including methyl, ethyl, propyl, butyl, pentyl and hexyl, the n-isomers of these residues, isopropyl, isobutyl, 1-methylbutyl, isopentyl, neopentyl, 2,2-dimethylbutyl, 2-methylpentyl, 3-methylpentyl, isohexyl, sec-butyl, tert-butyl and tert-pentyl. All these statements also apply if an alkyl group is substituted or occurs as a substituent on another residue, for example in an alkyl-O-residue (alkyloxy residue, alkoxy residue), an alkyl-O—C(O)— residue (alkyloxycarbonyl residue) or an aryl-alkyl- residue.

Alkyl groups can in general, independently of any other substituents which an alkyl groups carries, be unsubstituted or substituted by one or more fluorine substituents, for example by one, two, three, four or five fluorine substituents, or by one, two or three fluorine substituents. Such fluorine-substituted alkyl group can also be perfluoroalkyl groups, i.e. alkyl groups in which all hydrogen atoms are replaced by fluorine atoms. Examples of fluorine-substituted alkyl groups are —CF₃, —CHF₂, —CH₂F and —CF₂—CF₃, of which —CF₃ and —CF₂—CF₃ are examples of perfluoroalkyl groups. In one embodiment, an alkyl group in any occurrence, independently of other occurrences, and independently of any other substituents which the alkyl groups carries, is not substituted by fluorine, in another embodiment it is substituted by fluorine.

The term $(C_3-C_7)$-cycloalkyl is to be understood as meaning a residue of a saturated cyclic hydrocarbon cycle containing from 3 to 7 ring carbon atoms in a monocyclic ring. Examples of $(C_3-C_7)$-cycloalkyl are cycloalkyl residues containing 3, 4, 5, 6 or 7 ring carbon atoms like cyclopropyl, cyclobutyl, cyclopentyl, cyclohexyl or cycloheptyl. All cycloalkyl groups can be unsubstituted or substituted by one or more, for example one, two, three or four, identical or different substituents selected from the series consisting of fluorine and $(C_1-C_4)$-alkyl. In one embodiment, a cycloalkyl group is not substituted by fluorine and/or alkyl.

The term $(C_3-C_7)$-cycloalkane, which refers to the group which can be formed by $R^4$ and $R^5$ together with the carbon atom carrying them, is to be understood as meaning a cyclopropane, cyclobutane, cyclopentane, cyclohexane or cycloheptane ring one ring carbon atom of which, which is the carbon atom depicted in formula I which carries the groups $R^4$ and $R^5$, is bonded to the adjacent oxygen atom and C(O) group depicted in formula I.

The term Ar is to be understood as meaning phenyl, naphthyl or a residue of an aromatic, 5-membered or 6-membered, monocyclic hydrocarbon ring, wherein in the said hydrocarbon ring one or two ring carbon atoms are replaced by identical or different ring heteroatoms selected from the series consisting of N, O and S, such as furanyl, pyridinyl, oxazolyl, isoxazolyl, thiazolyl, isothiazolyl, imidazolyl, pyrazinyl, pyridazinyl, pyrimidinyl, pyrrolyl, pyrazolyl and thienyl residues, which can all be unsubstituted or substituted by one or more identical or different substituents selected from the series consisting of halogen, $(C_1-C_4)$-alkyl, $(C_3-C_7)$-cycloalkyl, $(C_3-C_7)$-cycloalkyl-$(C_1-C_4)$-alkyl-, cyano and $(C_1-C_4)$-alkyl-O—. Naphthyl can be 1-naphthyl and 2-naphthyl.

Halogen is fluorine, chlorine, bromine or iodine. In one embodiment, halogen is in any of its occurrences, independently of other occurrences, selected from the series consisting of fluorine, chlorine an bromine, in another embodiment from the series consisting of fluorine and chlorine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers in any ratio, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

Pharmaceutically acceptable salts of the compounds of formula I are understood to be nontoxic salts that are physiologically acceptable and pharmaceutically utilizable salts. Such salts of compounds of the formula I containing acidic groups, for example a carboxyl group COOH, are for example alkali metal salts or alkaline earth metal salts such as sodium salts, potassium salts, magnesium salts and calcium salts, and also salts with pharmaceutically acceptable quaternary ammonium ions such as tetramethylammonium or tetraethylammonium, and acid addition salts with ammonia and pharmaceutically acceptable organic amines, such as methylamine, dimethylamine, trimethylamine, ethylamine, triethylamine, ethanolamine or tris-(2-hydroxyethyl)amine. Basic groups contained in the compounds of the formula I form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I which simultaneously contain a basic group and an acidic group, can also be present as zwitterions (betaines), which are likewise included in the present invention.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of pharmaceutically acceptable salts.

The invention also includes solvates, derivatives and modifications of the compounds of the formula I, for example prodrugs, protected forms and other pharmaceutically acceptable derivatives. The invention relates in particular to prodrugs and protected forms of the compounds of the formula I, which can be converted into compounds of the formula I under physiological conditions. Suitable prodrugs for the compounds of the formula I, i.e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; H. Bundgaard, Drugs of the Future 16 (1991) 443; Hydrolysis in Drug and Prodrug Metabolism, B. Testa, J. M. Mayer, Wiley-VCH, 2003.

Suitable prodrugs for the compounds of the formula I are especially acyl prodrugs and carbamate prodrugs of acylatable nitrogen-containing groups such as amino groups and ester prodrugs and amide prodrugs of carboxylic acid groups which may be present in compounds of the formula I. In the acyl prodrugs and carbamate prodrugs a hydrogen atoms on a nitrogen atom in such groups is replaced with an acyl group or an ester group, for example a $(C_1-C_6)$-alkyl-O—C(O)— group. Suitable acyl groups and ester groups for acyl prodrugs and carbamate prodrugs are, for example, the groups $R^{p1}$—CO— and $R^{p2}$O—CO—, wherein $R^{p1}$ can be hydrogen, $(C_1-C_6)$-alkyl, $(C_3-C_7)$-cycloalkyl, $(C_3-C_7)$-cycloalkyl-$(C_1-C_4)$-alkyl-, Ar, $(C_6-C_{14})$-aryl, $(C_6-C_{14})$-aryl-$(C_1-C_4)$-alkyl- or Ar—$(C_1-C_4)$-alkyl-, for example, and wherein $R^{p2}$ has the meanings indicated for $R^{p1}$ with the exception of hydrogen. The term $(C_6\text{-}C_{14})$-aryl is understood as meaning a residue of a monocyclic, bicyclic or tricyclic aromatic hydrocarbon containing from 6 to 14 ring carbon atoms, for example 6, 7, 8, 9, 10, 11, 12, 13 or 14 ring carbon atoms. Examples are phenyl, naphthyl, for example 1-naphthyl and 2-naphthyl, or biphenylyl.

Also with respect to all embodiments of the invention specified herein it applies that the comprised compounds of the formula I are a subject of the invention in all their stereoisomeric forms and mixtures of stereoisomeric forms in any ratio, and in the form of their pharmaceutically acceptable salts, as well as in the form of their prodrugs.

The present invention also relates to processes for the preparation of the compounds of the formula I, by which the compounds are obtainable and which are another subject of the invention.

The compounds of the formula I can be prepared by utilizing procedures and techniques, which per se are well known and appreciated by one of ordinary skill in the art. Starting materials or building blocks for use in the general synthetic procedures that can be applied in the preparation of the compounds of formula I are readily available to one of ordinary skill in the art. In many cases they are commercially available or have been described in the literature. Otherwise they can be prepared from readily available precursor compounds analogously to procedures described in the literature, or by procedures or analogously to procedures described herein.

In general, compounds of the formula I can be prepared, for example in the course of a convergent synthesis, by linking two or more fragments which can be derived retrosynthetically from the formula I. More specifically, suitably substituted starting pyrazole derivatives are employed as building blocks in the preparation of the compounds of formula I. If not commercially available, such pyrazole derivatives can be prepared according to the well-known standard procedures for the formation of the pyrazole ring system. By choosing suitable precursor molecules, these pyrazole syntheses allow the introduction of a variety of substituents into the various positions of the pyrazole system, which can be chemically modified in order to finally arrive at the molecule of the formula I having the desired substituent pattern. As one of the comprehensive reviews in which numerous details and literature references on the chemistry of pyrazole and on synthetic procedures for their preparation can be found J. Eiguero in Comprehensive Heterocyclic Chemistry II, Eds. A. Katritzky, Ch. Rees, E. Scriven, Elsevier 1996, Vol. 3; K. Kirschke in Houben-Weyl, Methoden der Organischen Chemie (Methods of Organic Chemistry), Georg Thieme Verlag, Stuttgart, Germany, 1994, Vol. E8b Hetarene; T. Nagai et al. Org. Prep. Proced. Int. (1993), 25, 403; M. Elnagdi et al. Heterocycles (1985) 23, 3121; K. Makino et al. J. Heterocycl. Chem. (1998) 35, 489; K. Makino et al. J. Heterocycl. Chem. (1999) 36, 321. If starting pyrazole derivatives are not commercially available and have to be synthesized this can be done, for example, according to the well-known pyrazole syntheses mentioned above. Depending on the substituents in the starting materials, in certain pyrazole syntheses mixtures of positional isomers may be obtained, which, however, can also be separated by modern separation techniques like, for example, preparative HPLC.

In the following, some procedures of interest for the synthesis of the compounds of the invention are listed and referenced briefly. They illustrate some of the possible ways to access suitable pyrazole derivatives, and are standard procedures comprehensively discussed in the literature and well known to one skilled in the art.

1) N. Kudo et al. Chem. Pharm. Bull. (1999) 47, 857.

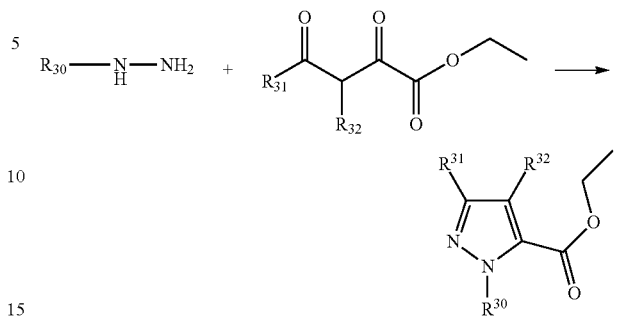

2) A. Padwa, J. Heterocycl. Chem. (1987) 24, 1225.

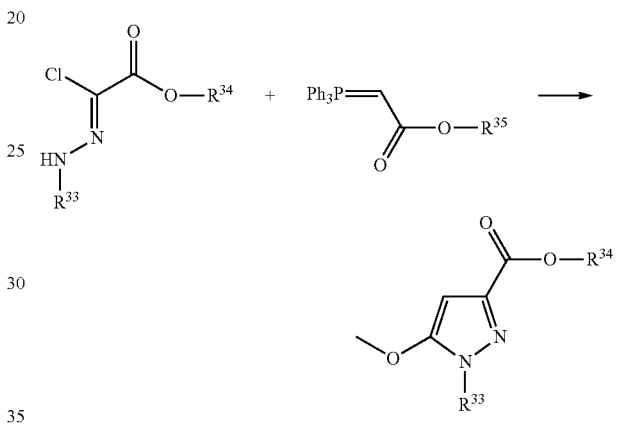

3) N. K. Markova et al., Zh. Org. Khim. (1983) 19, 2281.

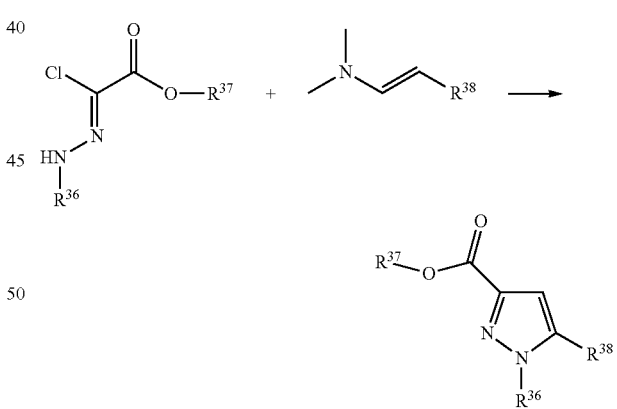

4) P. Bravo et al., Tetrahedron (1994) 50, 8827.

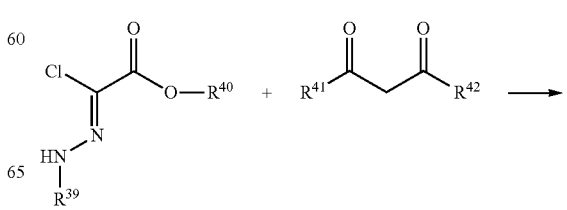

-continued
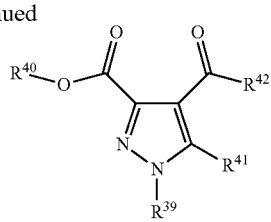
5) M. A. Martins et al., Synthesis (1995), 1491.
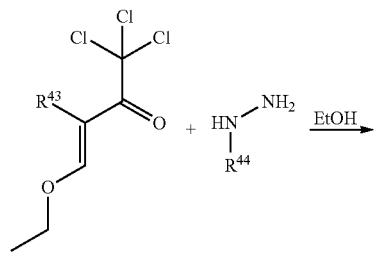
6) R. G. Jones et al., J. Org. Chem. (1955) 20, 1342.
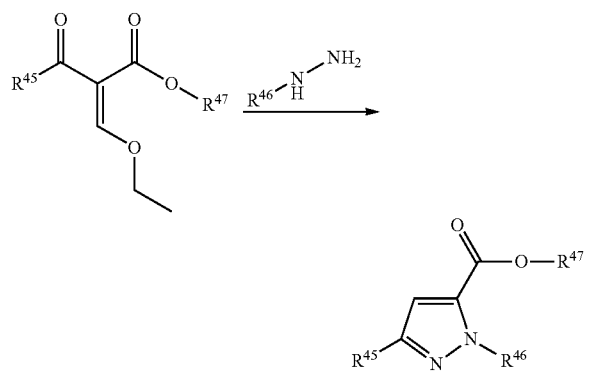
7) W. T. Ashton et al., J. Heterocycl. Chem. (1993) 30, 307.
8) K. I. Bookermilburn, Synlett (1992) 327.
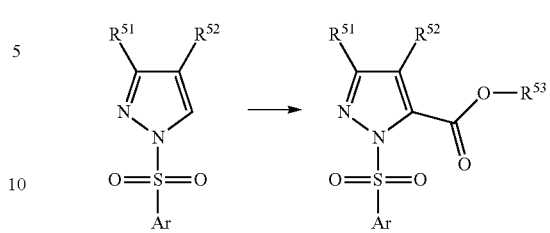
9) F. Farina et al., Heterocycles (1989) 29, 967.
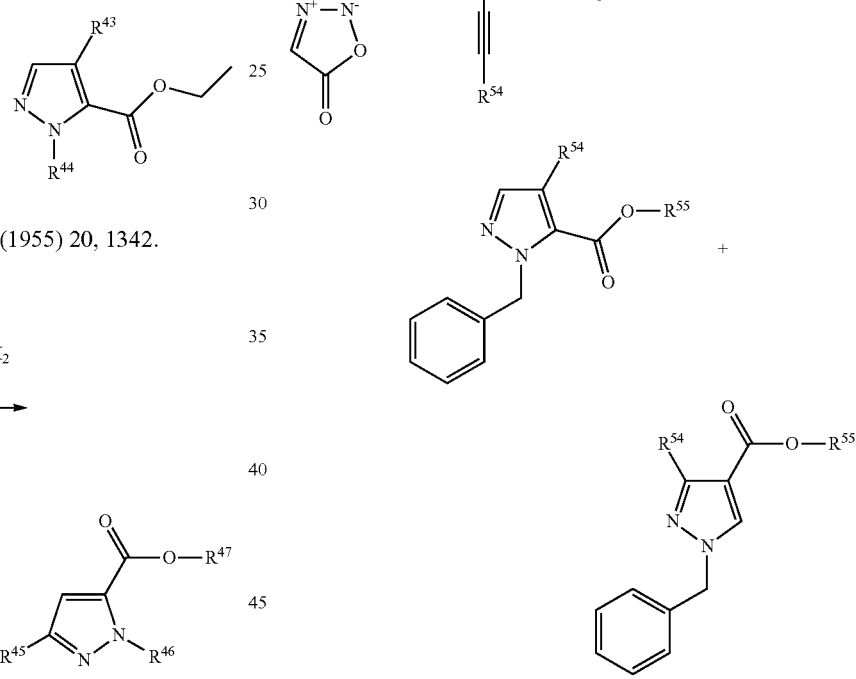
10) T. Hague et al., J. Med. Chem. (2002) 4669.
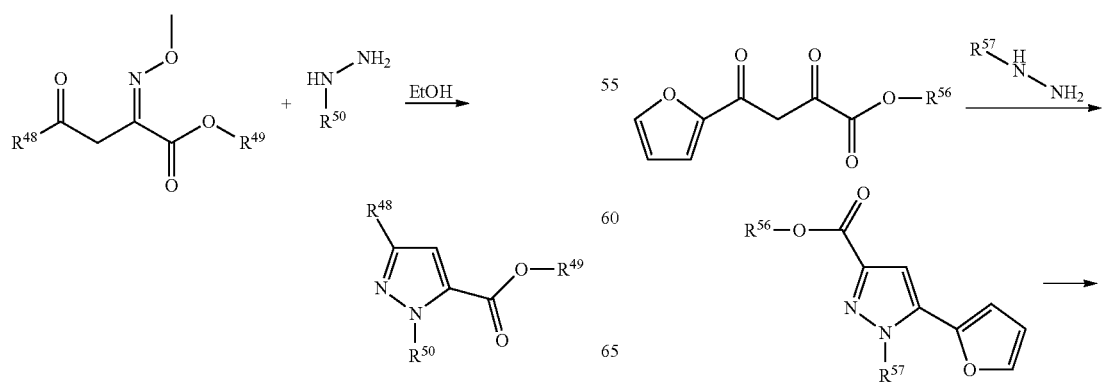

-continued
11) H. V. Patel, Synth. Commun. (1991) 21, 1583.
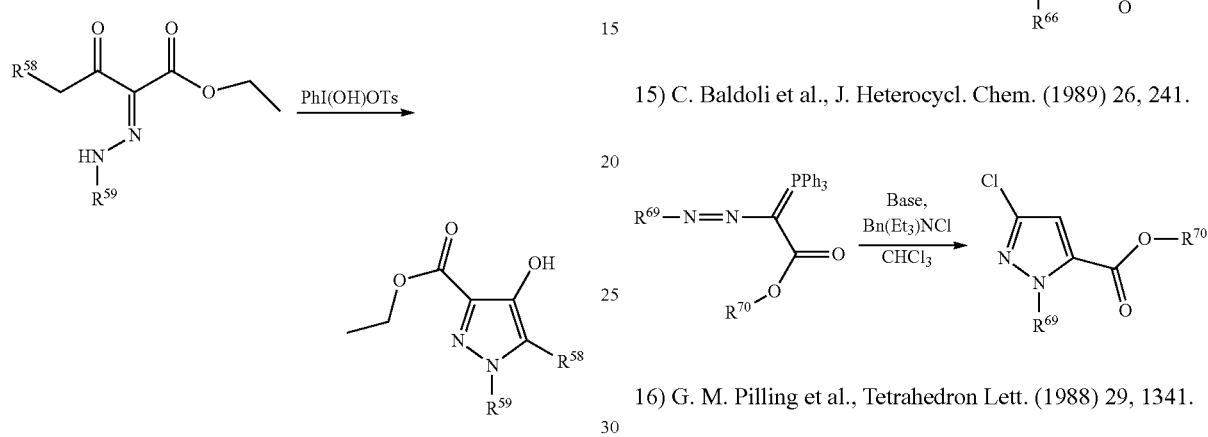
12) F. Farina et al., Heterocycles (1989) 29, 967.
13) R. Huisgen et al., J. Am. Chem. Soc. (1979) 101, 3647.
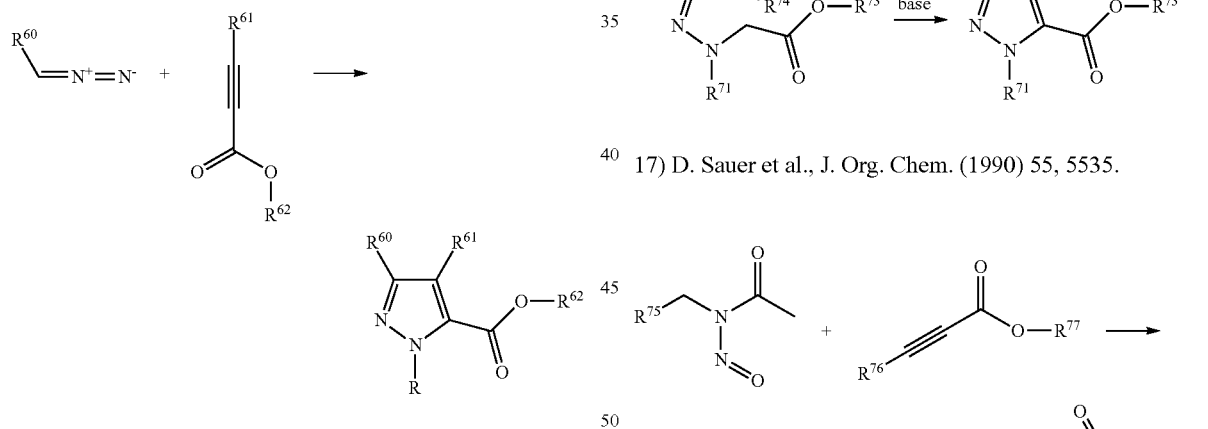
14) W. Sucrow et al., Angew. Chem., Int. Ed. (1975) 14, 560.
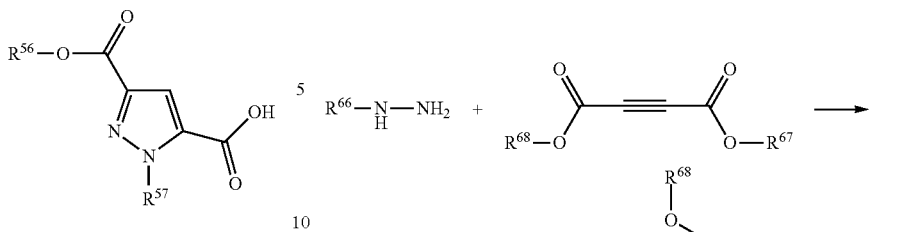
15) C. Baldoli et al., J. Heterocycl. Chem. (1989) 26, 241.
16) G. M. Pilling et al., Tetrahedron Lett. (1988) 29, 1341.
17) D. Sauer et al., J. Org. Chem. (1990) 55, 5535.
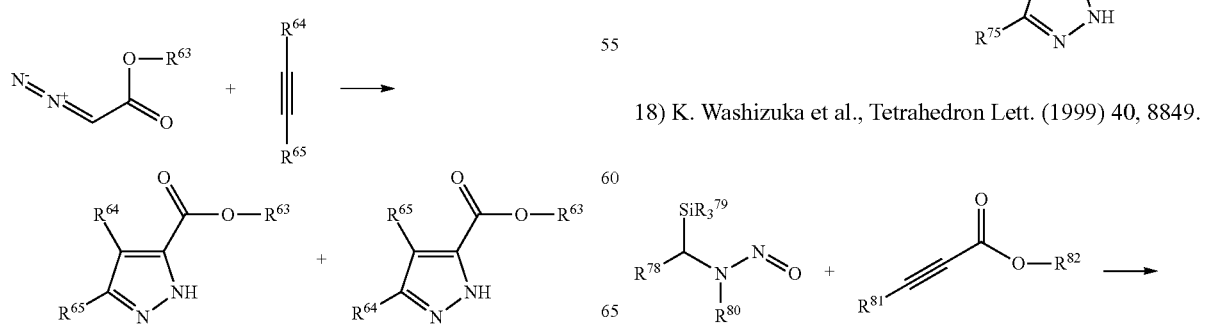
18) K. Washizuka et al., Tetrahedron Lett. (1999) 40, 8849.

19) F. Foti et al., Tetrahedron Lett. (1999) 40, 2605.

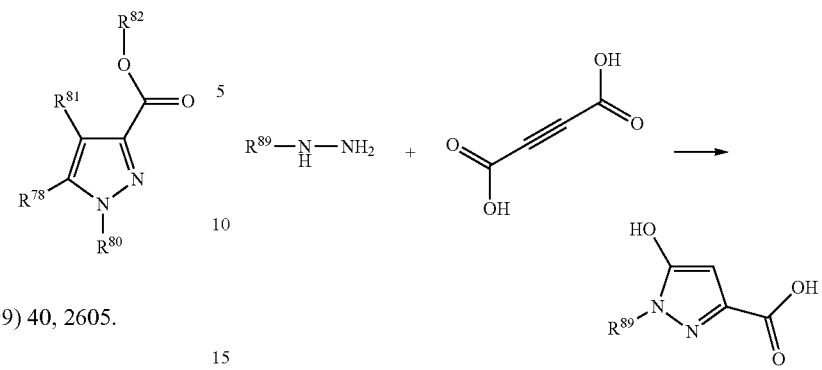

20) M. Martins et al., Synthesis (2003) 15, 2353.

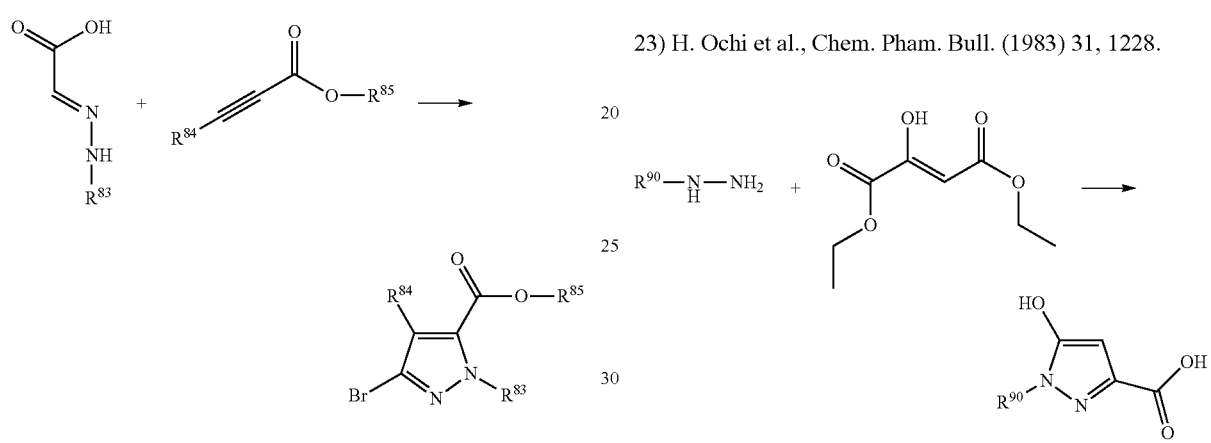

21) J. Nef, Liebigs Ann. Chem. (1893) 276, 231.

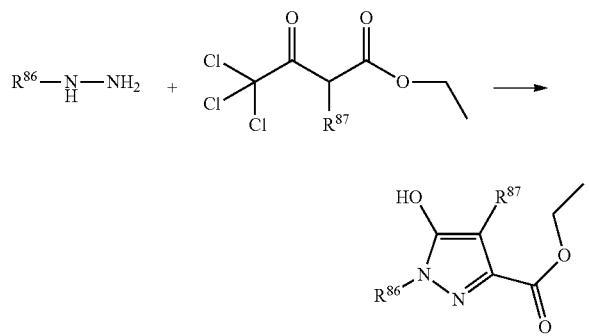

22) Leighton, J. Am. Chem. Soc. (1898) 20, 677.

23) H. Ochi et al., Chem. Pham. Bull. (1983) 31, 1228.

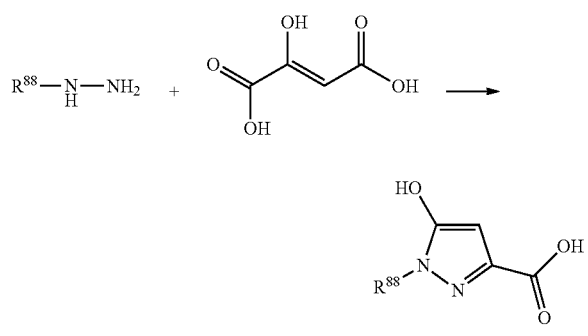

Although not always shown explicitly, in certain cases positional isomers will occur also during the synthesis by the mentioned reactions. Such mixtures of positional isomers can be separated by modern separation techniques like, for example, preparative HPLC.

Further, in order to obtain the desired substituents at the pyrazole ring system in the formula I, the functional groups introduced into the ring system during the pyrazole synthesis can be chemically modified. Especially the substituents present on the pyrazole ring system can be modified by a variety of reactions and thus the desired residues can be obtained. For example, a pyrazole carrying a hydrogen atom in a certain position such as the 4-position can also be obtained by saponification and subsequent decarboxylation of pyrazole carrying an ester group in the relevant position. Halogen atoms can be introduced, for example according to procedures like the following described in the literature. For the fluorination of pyrazoles N-fluoro-2,4,6-trimethylpyridinium triflate can be used (T. Umemoto, S. Fukami, G. Tomizawa, K. Harasawa, K. Kawada, K. Tomita, J. Am. Chem. Soc. (1990) 112, 8563; see also K. Manko et al., J. Fluorine Chem. (1988) 39, 435; R. Storer et al. Nucleosides Nucleotides (1999) 18; 203). Other suitable fluorinating reagents may also be employed where appropriate. The chlorination, bromination, or iodination of pyrazoles can be accomplished by the reaction with elemental halogens or by the use of N-halo-succinimides like NCS, NBS or NIS and many other reagents well known to those skilled in the art. In addition suitable procedures are for example described by M. Rodriguez-Franco et al., Tetrahedron Lett. (2001) 42, 863; J. Pawlas et al., J. Org. Chem. (2000) 65, 9001; Y. Huang et al., Org Lett (2000) 2, 2833; W. Holzer et al., J. Heterocycl. Chem. (1995) 32, 1351; N. Kudo et al., Chem. Pharm. Bull. (1999) 47, 857; G. Auzzi et al., Farmaco, Ed Sci. (1979) 34, 743; K. Morimoto et al., J. Heterocycl. Chem. (1997) 34, 537;

D. Jeon et al., Synth. Commun. (1998) 28, 2159. Depending on the reaction conditions, reagent, stoichiometry and substitution pattern the halogen is introduced in the 3-position and/or 4-position and/or 5-position. By selective halogen/metal exchange or metalation by selective hydrogen/metal exchange and subsequent reaction with a wide range of electrophiles various substituents can be introduced at the heterocyclic nucleus (M. R. Grimmett, Heterocycles (1994) 37, 2087; V. D. Gardner et al., J. Heterocycl. Chem. (1984), 21, 121; D. Butler et al., J. Org. Chem. (1971) 36, 2542). Among others, the corresponding pyrazolones can be useful precursors for the introduction of halogen atoms. For example, a 1H-pyrazol-3-ol can be converted to a 5-chloro-1H-pyrazole by using phosphorous oxychloride, for example. The 5-bromo-1H-pyrazole can be obtained from 1H-pyrazol-3-ol by similar standard procedures using phosphorous oxybromide, phosphorous tribromide or phosphorous pentabromide.

Halogens, hydroxy groups (via the triflate or nonaflate) or primary amines (via the diazonium salt), or after interconversion to the corresponding stannanes and boronic acids, present in the pyrazole structure can be converted into a variety of other functional groups like for example —CN, —$CF_3$, —$C_2F_5$, ethers, acids, amides, amines, alkyl or aryl groups mediated by means of transition metals, such as palladium or nickel catalysts or copper salts and reagents for example referred to below (F. Diederich, P. Stang, Metal-catalyzed Cross-coupling Reactions, Wiley-VCH, 1998; M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; T. Sakamoto, K. Ohsawa, J. Chem. Soc. Perkin Trans I, 1999, 2323; D. Nichols, S. Frescas, D. Marona-Lewicka, X. Huang, B. Roth, G. Gudelsky, J. Nash, J. Med. Chem, 1994, 37, 4347; P. Lam, C. Clark, S. Saubern, J. Adams, M. Winters, D. Chan, A. Combs, *Tetrahedron Lett.*, 1998, 39, 2941; D. Chan, K. Monaco, R. Wang, M. Winters, *Tetrahedron Lett.* 1998, 39, 2933; V. Farina, V. Krishnamurthy, W. Scott, The Stille Reaction, Wiley, 1994; F. Qing et al. J. Chem. Soc. Perkin Trans. 1 1997, 3053; S. Buchwald et al. J. Am. Chem. Soc. 2001, 123, 7727; S. Kang et al. Synlett 2002, 3, 427; S. Buchwald et al. Organic Lett. 2002, 4, 581; T. Fuchikami et al. Tetrahedron Lett. 1991, 32, 91; Q. Chen et al. Tetrahedron Lett. 1991, 32, 7689; M. R. Netherton, G. C. Fu, Topics in Organometallic Chemistry 2005, 14, 85-108; A. F. Littke, G. F. Fu, Angew. Chem. Int. Ed. 2002, 41, 4176-4211; A. R. Muci, S. L. Buchwald, Topics in Current Chemistry 2002, 219, 131-209).

Ester groups present in the pyrazole nucleus can be hydrolyzed to the corresponding carboxylic acids, which after activation can then be reacted with amines or alcohols under standard conditions. Furthermore these ester or acid groups can be reduced to the corresponding alcohols by many standard procedures. Ether groups present at the pyrazole, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups attached to the pyrazole ring system by application of parallel synthesis methodology, besides a variety of reactions, palladium, nickel or copper catalysis can be extremely useful. Such reactions are described for example in F. Diederich, P. Stang, Metal-catalyzed Cross-coupling Reactions, Wiley-VCH, 1998; M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; P. Lam, C. Clark, S. Saubern, J. Adams, M. Winters, D. Chan, A. Combs, Tetrahedron Lett. 1998, 39, 2941; D. Chan, K. Monaco, R. Wang, M. Winters, Tetrahedron Lett. 1998, 39, 2933; J. Wolfe, H. Tomori, J. Sadight, J. Yin, S. Buchwald, J. Org. Chem. 2000, 65, 1158; V. Farina, V. Krishnamurthy, W. Scott, The Stille Reaction, Wiley, 1994; S. Buchwald et al., J. Am. Chem. Soc. 2001, 123, 7727; S. Kang et al., Synlett 2002, 3, 427; S. Buchwald et al., Org. Lett. 2002, 4, 581.

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, Methoden der Organischen Chemie (Methods of Organic Chemistry), Georg Thieme Verlag, Stuttgart, Germany; or Organic Reactions, John Wiley & Sons, New York; R. C. Larock, Comprehensive Organic Transformations, Wiley-VCH, $2^{nd}$ ed., 1999; B. Trost, I. Fleming (eds.), Comprehensive Organic Synthesis, Pergamon, 1991; A. Katritzky, C. Rees, E. Scriven, Comprehensive Heterocyclic Chemistry II, Elsevier Science, 1996, in which details on the reactions and primary source literature can be found. Due to the fact that in the present case the functional groups are attached to a pyrazole ring it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding suitable reaction variants and reaction conditions in such cases does not cause any problems for one skilled in the art. The structural elements attached to the pyrazole ring in the compounds of the formula I can also be introduced into the starting pyrazole derivative using the methods outlined herein by consecutive reaction steps using parallel synthesis methodologies using procedures which per se are well known to one skilled in the art.

A subject of the present invention also is a process for preparing a compound of the formula I, which is outlined in the following scheme,

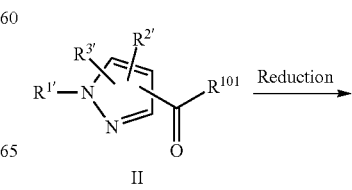

II

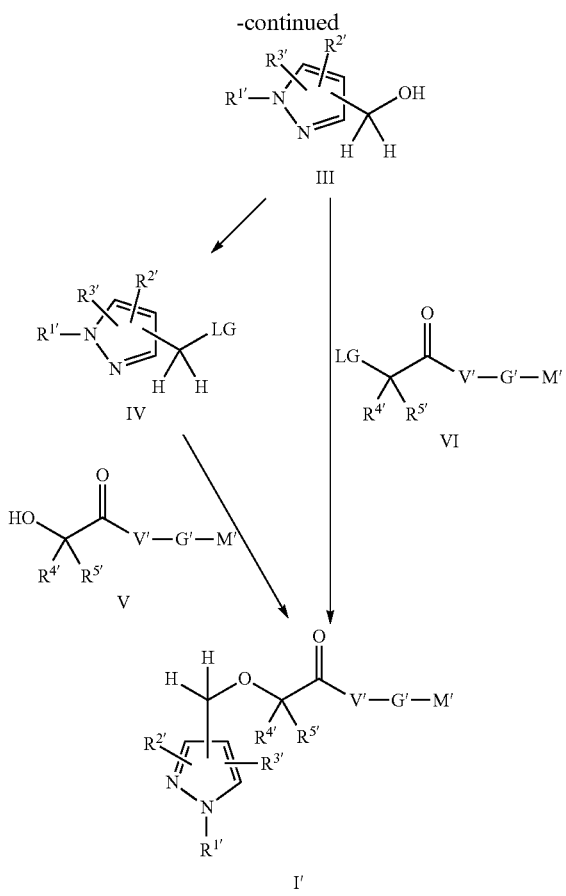

and which comprises

A) reducing a corresponding carboxylic acid or carboxylic acid ester of a pyrazole derivative of the formula II to a pyrazole derivative of the formula III carrying a hydroxymethylene group, B1) activating the hydroxymethylene group in the obtained pyrazole derivative of the formula III by transformation into a leaving group LG to give a pyrazole derivative of the formula IV, and subsequently etherifying the latter compound with a hydroxy compound of the formula V to obtain a pyrazole derivative of the formula I', which can already be the final compound of the formula I, or B2) reacting the obtained pyrazole derivative of the formula III with an alkylating compound of the formula VI, wherein LG is a leaving group, to obtain a pyrazole derivative of the formula I', which can already be the final compound of the formula I, C) optionally modifying the obtained compound of the formula I' by conversion and/or introduction any groups to give the final compound of the formula I, and/or converting the compound into a pharmaceutically acceptable salt thereof, D) isolating the final compound of the formula I or the pharmaceutically acceptable salt thereof;

wherein in the compounds of the formulae II, III, IV, V, VI and I' the residues $R^{1'}$, $R^{2'}$, $R^{3'}$, $R^{4'}$, $R^{5'}$, V', G' and M' are defined as in the compound of the formula I, and additionally functional groups can be present in protected form or in the form of precursor groups which are subsequently converted into the final groups present in the compound of the formula I;

LG is a leaving group such as halogen like chlorine or bromine, a sulfonyloxy group like methanesulfonyloxy or 4-methylbenzenesulfonyloxy, an azide group, or a diazonium group, for example; and $R^{101}$ is $(C_1-C_6)$-alkyl-O— or HO—, for example.

Compounds of the formula III can be obtained, for example, by reduction of a corresponding carboxylic acid or carboxylic ester of the formula II using well-known procedures and reagents like for example $BH_3$, $NaBH_4$ or $LiAlH_4$.

If structural features present in the pyrazole derivatives of the formula I, which are contained in the compounds of the formula V or the formula VI, have not already been introduced during a preceding step, for example during a synthesis of the pyrazole nucleus, the respective groups can, for example, be introduced into the pyrazole system by standard alkylation procedures well-known to one skilled in the art. The starting pyrazole derivative III that is to be employed in such a reaction carries a hydroxymethylen group. Alkylation of the aforementioned group can, for example, be performed under standard conditions, preferably in the presence of a base like $K_2CO_3$, $Cs_2CO_3$, NaH or KOtBu, using an alkylating compound of the formula VI wherein LG is a leaving group, such as for example halogen like chlorine, bromine or iodine, or a sulfonyloxy group like tosyloxy, mesyloxy or trifluormethylsulfonyloxy. Alternatively, the hydroxymethylene group of a pyrazole derivative of the formula III can be activated by transformation into a leaving group LG by conversion into a halomethylene group or sulfonyloxymethylene group like tosyloxymethylene, mesyloxymethylene or trifluormethylsulfonyloxymethylene to give a pyrazole derivatives of the formula IV. These pyrazole derivatives of the formula IV can then be etherified, for example, under standard conditions, preferably in the presence of a base like $K_2CO_3$, $Cs_2CO_3$, NaH or KOtBu, using a hydroxy derivative of the formula V. These standard procedures are for example described in treatises like M. Smith, J. March, March's Advanced Organic Chemistry, Wiley-VCH, 2001; Houben-Weyl, Methoden der Organischen Chemie (Methods of Organic Chemistry), Georg Thieme Verlag, Stuttgart, Germany; Organic Reactions, John Wiley & Sons, New York; R. C. Larock, Comprehensive Organic Transformations, Wiley-VCH, $2^{nd}$ ed., 1999; B. Trost, I. Fleming (eds.), Comprehensive Organic Synthesis, Pergamon, 1991.

The group LG may, for example, also be a hydroxy group which, in order to achieve the alkylation reaction, can be activated under the well-known conditions of the Mitsunobu procedure (O. Mitsunobu, Synthesis 1981, 1) or by further modified procedures (A. Tunoori, D. Dutta, G. Gunda, Tetrahedron Lett. 39 (1998) 8751; J. Pelletier, S. Kincaid, Tetrahedron Lett. 41 (2000) 797; D. L. Hughes, R. A. Reamer, J. J. Bergan, E. J. J. Grabowski, J. Am. Chem. Soc. 110 (1998) 6487; D. J. Camp, I. D. Jenkins, J. Org. Chem. 54 (1989) 3045; D. Crich, H. Dyker, R. J. Harris, J. Org. Chem. 54 (1989) 257).

The compounds of the formulae II, III, IV, V, VI and I' obtained according to the reactions described herein can already contain the desired final groups, i.e. $R^{1'}$, $R^{2'}$, $R^{3'}$, $R^{4'}$, $R^{5'}$, V', G' and M' can be the groups $R^1$, $R^2$, $R^3$, $R^4$, $R^5$, V, G and M as defined in formula I, or optionally in the compounds of the formulae II, Ill, IV, V, VI and I' the residues $R^{1'}$, $R^{2'}$, $R^{3'}$, $R^{4'}$, $R^{5'}$, V', G' and M' are subsequently converted into the residues $R^1$, $R^2$, $R^3$, $R^4$, $R^5$, V, G and M to give the desired compound of the formula I. Thus, the residues $R^1$, $R^{2'}$, $R^{3'}$, $R^{4'}$, $R^{5'}$, V', G' and M' contained in the compounds of the formulae II, III, IV, V, VI and I' can have the denotations of the residues in the compounds of the formula I, or in addition they can also be present in the form of groups that can subsequently be transformed into the final groups of the formula I and, for example, functional groups can be present in the form of precursor groups or of derivatives or in protected form. In the course f the preparation of the compounds of the formula I it can generally be advantageous or necessary to introduce functional groups which reduce or prevent undesired reactions or side reactions in the respective synthesis steps, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991; or P. Kocienski, Protecting Groups, Thieme, 1994). Examples of precursor groups are cyano groups and nitro groups. The cyano group can, in a later step, be transformed into carboxylic acid derivatives or by reduction into aminomethyl groups. Nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000). For example, a phenolic hydroxy group can be attached to a trityl-polystyrene resin, which serves as a protecting group, and the molecule is cleaved from this resin by treatment with trifluoroacetic acid (TFA) or other acids at a later stage of the synthesis.

The residue —V'-G'-M' in the compounds of the formulae V, VI and I', which can be identical or different, can be, for example, hydroxy or $(C_1-C_4)$-alkoxy, i.e., the groups —C(O)—V'-G'-M' present in the compounds of the formulae V, VI and I' can be, for example, the free carboxylic acids or esters thereof like alkyl esters. The groups can also be any other activated derivative of a carboxylic acid which allows amide or ester formation with a compound of the formula H—V'-G'-M'. The activated derivative can be, for example, an acid chloride, an activated ester like a substituted phenyl ester or thioester, an azolide like an imidazolide, an azide or a mixed anhydride, for example a mixed anhydride with a carbonic acid ester or with a sulfonic acid. These derivatives can all be prepared from the carboxylic acid by standard procedures and can be reacted with an amine or alcohol of the formula H—V'-G'-M' under standard conditions. A carboxylic acid group —COOH representing —C(O)—V'-G'-M' in a compound of the formulae V and VI can be obtained, for example by standard hydrolysis procedures, from an ester group introduced into the pyrazole system during a pyrazole synthesis.

Compounds of the formula I in which a group —C(O)—V'-G'-M' is an amide group can be prepared from amines and compounds is a carboxylic acid group or an ester or thioester thereof by common amidation reactions. Especially for the preparation of amides the compounds containing a carboxylic acid group can be condensed under standard conditions with compounds of the formula H—V'-G'-M' which are amines by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CU) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC), bis-(2-oxo-3-oxazolidinyl)-phosphoryl chloride (BOP-Cl), O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU), bromo-tris-pyrrolidino-phosphonium hexafluorophosphate (Pybrop) and many others.

The activation of the carboxylic acid function may also favorably be carried out, for example, by conversion of the carboxylic acid group into the pentafluorophenyl ester using dicyclohexylcarbodiimide and pentafluorophenol or by using reagents like pentafluorophenyl trifluoroacetate, tert-butyl pentafluorophenyl carbonate, bis(pentafluorophenyl)carbonate, -pentafluorophenyl 4-methylbenzenesulfonate, pentafluorophenyl-tetramethyluronium hexafluorophosphate, octafluoroacetophenone. The activation of the carboxylic function by conversion to other phenyl esters like for example 4-nitro-phenyl esters or 2-nitro-phenyl esters can be also effective. The activation and the subsequent reaction with a group of the formula H—V'-G'-M' are usually carried out in the presence of an inert solvent or diluent, for example dichloromethane, chloroform, tetrahydrofuran (THF), diethyl ether, n-heptane, n-hexane, n-pentane, cyclohexane, diisopropyl ether, methyl tert-butyl ether, acetonitrile, N,N-dimethylformamide (DMF), N,N-dimethylacetamide (DMA), N-methylpyrrolidin-2-one (NMP), dimethyl sulfoxide, dioxane, toluene, benzene, ethyl acetate or a mixture of these solvents, if appropriate with addition of a base such as, for example, potassium tert-butoxide or tributylamine or triethylamine or diisopropylethylamine or N-ethylmorpholine.

The residues $R^{1'}$, $R^{2'}$, $R^{3'}$, $R^{4'}$, $R^{5'}$ present in a pyrazole of the formulae II, III, IV, V, VI and I', or a residue in which functional groups within the residue are present in protected form or in the form of a precursor group, can for example be introduced into the pyrazole system by conventional literature procedures for the alkylation, arylation, amination, etherification or thioetherification of pyrazoles well-known to those skilled in the art. The appropriately substituted pyrazole useful for these reactions carries a leaving group like for example halogen, triflate, nonaflate, tosylate, azide, or a diazonium salt. Preferably the reaction is carried out in the presence of a base like $K_2CO_3$, $Cs_2CO_3$, NaH or KOtBu. The desired transformation can also be accomplished with halogens, hydroxy groups (via the triflate or nonaflate) or primary amines (via the diazonium salt) or after interconversion to the corresponding stannane, or boronic acid—present in the pyrazole structure—can be converted into a variety of other functional groups like for example —CN, —$CF_3$, —$C_2F_5$, ethers, acids, amides, amines, alkyl or aryl groups mediated by means of transition metals, such as palladium or nickel catalysts or copper salts and reagents for example referred to below (F. Diederich, P. Stang, Metal-catalyzed Cross-coupling Reactions, Wiley-VCH, 1998; M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; T. Sakamoto, K. Ohsawa, J. Chem. Soc. Perkin Trans I, 1999, 2323; D. Nichols, S. Frescas, D. Marona-Lewicka, X. Huang, B. Roth, G. Gudelsky, J. Nash, J. Med. Chem., 1994, 37, 4347; P. Lam, C. Clark, S. Saubern, J. Adams, M. Winters, D. Chan, A. Combs, Tetrahedron Lett., 1998, 39, 2941; D. Chan, K. Monaco, R. Wang, M. Winters, Tetrahedron Lett. 1998, 39, 2933; V. Farina, V. Krishnamurthy, W. Scott, The Stille Reaction, Wiley, 1994; F. Qing et al. J. Chem. Soc. Perkin Trans. 11997, 3053; S. Buchwald et al. J. Am. Chem. Soc. 2001, 123, 7727; S. Kang et al. Synlett 2002, 3, 427; S. Buchwald et al. Organic Lett. 2002, 4, 581; T. Fuchikami et al. Tetrahedron Lett. 1991, 32, 91; Q. Chen et al. Tetrahedron Lett. 1991, 32, 7689; M. R. Netherton, G. C. Fu, Topics in Organometallic Chemistry 2005, 14, 85-108; A. F. Littke, G. F. Fu, Angew.

Chem. Int. Ed. 2002, 41, 4176-4211; A. R. Muci, S. L. Buchwald, Topics in Current Chemistry 2002, 219, 131-209.

The compounds of the formula I are effective LPAR5 antagonists which antagonize the effect of endogenous LPA on its LPAR5 receptor. In particular are the compounds of the formula I effective platelet, mast cell and microglial cell LPA receptor LPAR5 antagonists. The compounds of the invention antagonize the platelet aggregating effect of the activation of the platelet LPA receptor LPAR5, the LPA-mediated activation of human mast cells and the LPA-mediated activation of microglia cells. In addition, the compounds of the formula I of the invention also have further advantageous properties, for instance stability in plasma and liver and selectivity versus other receptors whose agonism or antagonism is not intended. This good selectivity, for example, makes it possible to reduce potential side effects existing with regard to molecules having inadequate selectivity.

A subject of the present invention also are the compounds of the formula I and/or the pharmaceutically acceptable salts thereof and/or prodrugs thereof for use as a medicament or as a pharmaceutical, and pharmaceutical compositions which comprise an effective amount of at least one compound of the formula I and/or a pharmaceutical acceptable salt thereof and/or a prodrug thereof and a pharmaceutically acceptable carrier, i.e. one or more pharmaceutically acceptable carrier substances or excipients and/or auxiliary substances or additives, and can be employed in human, veterinary or phytoprotective use.

The activity of the compounds of the formula I can be determined, for example, in the assays described below or in other in vitro or ex vivo assays known to those skilled in the art. The ability of the compounds to inhibit LPA-induced aggregation of platelets may be measured by methods similar to those described in the literature (for example, Holub and Waston in Platelets: A Practical Approach, pp 236-239, Oxford University Press 1996) and by the methods described below. The results of these assays clearly demonstrate that the compounds of the invention are functional antagonists of the platelet LPA receptor LPAR5 and are therefore useful for inhibiting platelet aggregation and thrombus formation. The ability of the compounds to inhibit LPA-induced activation of mast cells or microglial cells may also be measured by using the FLIPR system.

As LPA receptor LPAR5 antagonists, the compounds of the formula I and/or their pharmaceutically acceptable salts and/or their prodrugs are generally suitable for the treatment, including therapy and prophylaxis, of conditions in which the activity of LPAR5 receptor plays a role or has an undesired extent, or which can favorably be influenced by inhibiting LPAR5 receptors or decreasing the activity, or for the prevention, alleviation or cure of which an inhibition of LPA receptor LPAR5 or a decrease in the activity is desired by the physician.

Thus, a subject of the invention also are the compounds of the formula I and/or the pharmaceutically acceptable salts thereof and/or the prodrugs thereof for the use in the treatment, including therapy and prophylaxis, of a disease or disease state responsive to the inhibition of the LPA receptor LPAR5 and/or the reduction or inhibition of platelet aggregation or thrombus formation and/or the reduction or inhibition of activation of mast cells and/or the reduction or inhibition of activation of microglial cells.

A subject of the invention also is the use of a compound of the formula I and/or the pharmaceutically acceptable salts thereof and/or the prodrugs thereof for the manufacture of a medicament for the treatment, including therapy and prophylaxis, of a disease or disease state responsive to the inhibition of the LPA receptor LPAR5 and/or the reduction or inhibition of platelet aggregation or thrombus formation and/or the reduction or inhibition of activation of mast cells and/or the reduction or inhibition of activation of microglial cells.

As inhibition of the LPA receptor LPAR5 influences platelet activation and platelet aggregation, the compounds of the formula I and/or their pharmaceutically acceptable salts and/or their prodrugs are generally suitable for reducing blood thrombus formation, or for the treatment, including therapy and prophylaxis, of conditions and diseases in which the activity of the platelet aggregation plays a role or has an undesired extent, or which can favorably be influenced by reducing thrombus formation, or for the prevention, alleviation or cure of which a decreased activity of the platelet aggregation system is desired by the physician. A specific subject of the present invention thus is the reduction or inhibition of unwanted thrombus formation, in particular in an individual, by administering an effective amount of a compound of the formula I and/or a pharmaceutically acceptable salt and/or a prodrug thereof, as well as pharmaceutical compositions therefore.

As inhibition of the LPA receptor LPAR5 influences mast cell activation the compounds of the formula I and/or their pharmaceutically acceptable salts and/or their prodrugs are generally suitable for reducing mast cell activation, or for the treatment, including therapy and prophylaxis, of conditions and diseases in which the activity of mast cells plays a role or has an undesired extent, or which can favorably be influenced by reducing mast cell activation, or for the prevention, alleviation or cure of which a decreased activity of the mast cell system is desired by the physician. A specific subject of the present invention thus is the reduction or inhibition of unwanted activation of mast cells, in particular in an individual, by administering an effective amount of a compound of the formula I and/or a pharmaceutically acceptable salt and/or a prodrug thereof, as well as pharmaceutical compositions therefore.

As inhibition of the LPA receptor LPAR5 influences microglial cell activation the compounds of the formula I and/or their pharmaceutically acceptable salts and/or their prodrugs are generally suitable for reducing microglial cell activation, or for the treatment, including therapy and prophylaxis, of conditions in which the activity of microglial cells plays a role or has an undesired extent, or which can favorably be influenced by reducing microglial cell activation, or for the prevention, alleviation or cure of which a decreased activity of the microglial cell system is desired by the physician. A specific subject of the present invention thus are the reduction or inhibition of unwanted activation of microglial cell, in particular in an individual, by administering an effective amount of a compound of the formula I and/or a pharmaceutically acceptable salt and/or a prodrug thereof, as well as pharmaceutical compositions therefore.

The present invention also relates to the compounds of the formula I and/or their pharmaceutically acceptable salts and/or their prodrugs for the use in the treatment, including therapy and prophylaxis, of thromboembolic diseases, such as deep vein thrombosis, venous and arterial thromboembolism, thrombophlebitis, coronary and cerebral arterial thrombosis, cerebral embolism, renal embolism, pulmonary embolism, disseminated intravascular coagulation, cardiovascular disorders, such as transient ischemic attacks, strokes, acute myocardial infarction, unstable angina, chronic stable angina, peripheral vascular disease, preeclampsia/eclampsia, and thrombotic cytopenic purpura and development and progression of inflammatory disorders, such as hyperalgesia, asthma, multiple sclerosis, inflammatory pain, angiogenesis, atherothrombosis or allergic responses, or restenoses.

The present invention also relates to the use of the compounds of the formula I and/or their pharmaceutically acceptable salts and/or their prodrugs for the manufacture of pharmaceutical compositions or medicaments for inhibition of the LPA receptor LPAR5 or for influencing platelet activation, platelet aggregation and platelet degranulation and promote platelet disaggregation, inflammatory response and/or for the treatment, including therapy and prophylaxis of the diseases mentioned above or below, for example for the production of medicaments for the treatment, including therapy and prophylaxis, of cardiovascular disorders, thromboembolic diseases or restenosis, for the treatment of deep vein thrombosis, venous and arterial thromboembolism, thrombophlebitis, coronary and cerebral arterial thrombosis, cerebral embolism, renal embolism, pulmonary embolism, disseminated intravascular coagulation, transient ischemic attacks, strokes, acute myocardial infarction, unstable angina, chronic stable angina, peripheral vascular disease, preeclampsia/eclampsia, and thrombotic cytopenic purpura and development and progression of inflammatory disorders, such as hyperalgesia, asthma, multiple sclerosis, angiogenesis, allergic responses and others.

The invention also relates to the compounds of the formula I and/or their pharmaceutically acceptable salts and/or their prodrugs for the use in the treatment, including therapy and prophylaxis, of the diseases mentioned above or below, for example for use in the treatment of cardiovascular disorders, thromboembolic diseases, atherothrombosis or restenoses, and to methods of treatment aiming at such purposes including methods for said therapies and prophylaxis.

Due to the central role of the platelet LPA receptor LPAR5 in LPA-mediated activation of platelets, the invention also relates to compounds of the formula I and/or the pharmaceutically acceptable salts thereof for the use in the treatment, including therapy and prophylaxis, of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, a risk of pulmonary thromboembolism, or disseminated systemic intravascular coagulatopathy occurring in vascular systems during septic shock, certain viral infections or cancer. The invention also relates to the use of a compound of the formula I and/or the pharmaceutically acceptable salts thereof for the manufacture of a medicament for the treatment, including therapy and prophylaxis of said disease states.

Due to the central role of the LPA receptor LPAR5 in LPA-mediated activation of mast cells and/or microglia cells, the invention also relates to compounds of the formula I and/or the pharmaceutically acceptable salts thereof for the use in the treatment, including therapy and prophylaxis, of disease states such as inflammatory pain, asthma, angiogenesis, demyelating diseases of (a) the central nervous system such as, multiple sclerosis, transverse myelitis, optic neuritis, Devic's disease and (b) the peripheral nervous system such as Guillain-Barre syndrome or chronic inflammatory demyelinating polyneuropathy, as well as to the use of a compound of the formula I and/or the pharmaceutically acceptable salts thereof for the manufacture of a medicament for the treatment, including therapy and prophylaxis of said disease states.

The compounds of the formula I and their pharmaceutically acceptable salts and their prodrugs can be administered to animals, preferably to mammals, and in particular to humans as pharmaceuticals for therapy or prophylaxis. They can be administered alone, or in mixtures with one another or in the form of pharmaceutical compositions, which permit enteral or parenteral administration.

The pharmaceutical compositions according to the invention can be administered orally, for example in the form of pills, tablets, lacquered tablets, coated tablets, granules, hard and soft gelatine capsules, solutions, syrups, emulsions, suspensions or aerosol mixtures. Administration can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical compositions according to the invention are prepared in a manner known per se and familiar to one skilled in the art, pharmaceutically acceptable inert inorganic and/or organic carrier substances and/or auxiliary substances being used in addition to one or more compounds of the formula I and/or their pharmaceutically acceptable salts and/or their prodrugs. For the production of pills, tablets, coated tablets and hard gelatine capsules it is possible to use, for example, lactose, cornstarch or derivatives thereof, talc, stearic acid or its salts, etc. Carrier substances for soft gelatine capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical compositions normally contain about 0.5% to about 90% by weight of the compounds of the formula I and/or their pharmaceutically acceptable salts and/or their prodrugs. The amount of the active ingredient of the formula I and/or its pharmaceutically acceptable salts and/or its prodrugs in the pharmaceutical compositions normally is from about 0.5 mg to about 1000 mg, preferably from about 1 mg to about 500 mg.

In addition to the active ingredients of the formula I and/or their pharmaceutically acceptable salts and/or prodrugs and to carrier substances or excipients, the pharmaceutical compositions can contain auxiliary substances or additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their pharmaceutically acceptable salts and/or their prodrugs. In case a pharmaceutical composition contains two or more compounds of the formula I, the selection of the individual compounds can aim at a specific overall pharmacological profile of the pharmaceutical composition. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or a pharmaceutically acceptable salt and/or its prodrug, the pharmaceutical compositions can also contain one or more other pharmaceutically, therapeutically and/or prophylactically active ingredients.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

The compounds of the present invention are also useful as standard or reference compounds, for example as a quality standard or control, in tests or assays involving the inhibition of the LPA receptor LPAR5. Such compounds may be provided in a commercial kit, for example, for use in pharmaceutical research involving the LPA receptor LPAR5. For example, a compound of the present invention can be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention can be used to test their effectiveness.

A compound of the formula I can also advantageously be used as an antiaggregant outside an individual. For example, an effective amount of a compound of the invention can be contacted with a freshly drawn blood sample to prevent aggregation of the blood sample. Further, a compound of the formula I or its salts can be used for diagnostic purposes, for example in vitro diagnoses, and as an auxiliary in biochemical investigations. For example, a compound of the formula I can be used in an assay to identify the presence of the LPA receptor LPAR5 or to isolate the LPA receptor LPAR5 containing tissue in a substantially purified form. A compound of the invention can be labeled with, for example, a radioisotope, and the labeled compound bound to the LPA receptor LPAR5 is then detected using a routine method useful for detecting the particular label. Thus, a compound of the formula I or a salt thereof can be used as a probe to detect the location or amount of LPAR5 activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in detail in the examples given below which are intended to be merely illustrative of the present invention and not limiting it in either scope or spirit. Those with skill in the art will readily understand that known variations of the conditions and processes described in the examples can be used to synthesize the compounds of the present invention.

Furthermore, the following subject-matters (1) to (12) are disclosed herein, which comprise additional compounds beside the compounds as covered by the claim set. The additional compounds can be prepared by the same methods as disclosed herein for the preparation of the inventive compounds.

(1) A compound of the formula I,

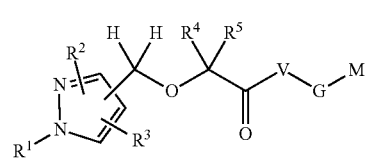

wherein
$R^1$ is selected from the series consisting of hydrogen, ($C_1$-$C_6$)-alkyl, ($C_3$-$C_7$)-cycloalkyl, ($C_3$-$C_7$)-cycloalkyl-($C_1$-$C_4$)-alkyl-, Ar and Ar—($C_1$-$C_4$)-alkyl-;

$R^2$ and $R^3$ are independently of each other selected from the series consisting of hydrogen, halogen, ($C_1$-$C_4$)-alkyl, ($C_3$-$C_7$)-cycloalkyl, ($C_3$-$C_7$)-cycloalkyl-($C_1$-$C_4$)-alkyl-, Ar, Ar—($C_1$-$C_4$)-alkyl-, ($C_1$-$C_4$)-alkyl-O—, ($C_3$-$C_7$)-cycloalkyl-O—, ($C_3$-$C_7$)-cycloalkyl-($C_1$-$C_4$)-alkyl-O—, Ar—O— and Ar—($C_1$-$C_4$)-alkyl-O—, or the groups $R^2$ and $R^3$, in case they are bonded to adjacent ring carbon atoms, together with the carbon atoms carrying them form a benzene ring which is unsubstituted or substituted by one or more identical or different substituents selected from the series consisting of halogen, ($C_1$-$C_4$)-alkyl, cyano and ($C_1$-$C_4$)-alkyl-O—;

$R^4$ and $R^5$ are independently of each other selected from the series consisting of hydrogen, fluorine and ($C_1$-$C_6$)-alkyl, or the groups $R^4$ and $R^5$ together with the carbon atom carrying them form a ($C_3$-$C_7$)-cycloalkane ring which is unsubstituted or substituted by one or more identical or different substituents selected from the series consisting of fluorine and ($C_1$-$C_4$)-alkyl;

$R^{11}$, $R^{12}$, $R^{13}$ and $R^{14}$ are independently of each other selected from the series consisting of hydrogen and ($C_1$-$C_4$)-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, ($C_1$-$C_4$)-alkyl, ($C_3$-$C_7$)-cycloalkyl, ($C_3$-$C_7$)-cycloalkyl-($C_1$-$C_4$)-alkyl-, cyano and ($C_1$-$C_4$)-alkyl-O—;

V is selected from the series consisting of $R^{11}$—O— and $R^{12}$—N($R^{13}$)—, and in this case G and M are not present, or V is selected from the series consisting of —N($R^{14}$)—, —N($R^{14}$)—($C_1$-$C_4$)-alkyl-, —O— and —O—($C_1$-$C_4$)-alkyl-, and in this case G is selected from the series consisting of a direct bond and phenylene which is unsubstituted or substituted by one or more identical or different substituents selected from the series consisting of halogen, $(C_1$-$C_4)$-alkyl, cyano and $(C_1$-$C_4)$-alkyl-O—, provided that G is not a direct bond if V is —N($R^{14}$)— or —O—, and M is selected from the series consisting of $R^{11}$—O—C(O)— and $R^{12}$—N($R^{13}$)—C(O)—;

wherein all alkyl groups are unsubstituted or substituted by one or more fluorine substituents, and all cycloalkyl groups are unsubstituted or substituted by one or more identical or different substituents selected from the series consisting of fluorine and $(C_1$-$C_4)$-alkyl;

in any of its stereoisomeric forms or a mixture of stereoisomeric forms in any ratio, or a pharmaceutically acceptable salt thereof.

(2) A compound of the formula I according to subject-matter (1), wherein $R^1$ is selected from the series consisting of hydrogen, $(C_1$-$C_6)$-alkyl, $(C_3$-$C_7)$-cycloalkyl, Ar and Ar—$(C_1$-$C_4)$-alkyl-;

$R^2$ and $R^3$ are independently of each other selected from the series consisting of hydrogen, $(C_1$-$C_4)$-alkyl, $(C_3$-$C_7)$-cycloalkyl, $(C_3$-$C_7)$-cycloalkyl-$(C_1$-$C_4)$-alkyl-, Ar, Ar—$(C_1$-$C_4)$-alkyl-, $(C_1$-$C_4)$-alkyl-O—, $(C_3$-$C_7)$-cycloalkyl-O—, $(C_3$-$C_7)$-cycloalkyl-$(C_1$-$C_4)$-alkyl-O—, Ar—O— and Ar—$(C_1$-$C_4)$-alkyl-O—, or the groups $R^2$ and $R^3$, in case they are bonded to adjacent ring carbon atoms, together with the carbon atoms carrying them form a benzene ring which is unsubstituted or substituted by one or more identical or different substituents selected from the series consisting of halogen, $(C_1$-$C_4)$-alkyl, cyano and $(C_1$-$C_4)$-alkyl-O—;

$R^4$ and $R^5$ are independently of each other selected from the series consisting of hydrogen and $(C_1$-$C_6)$-alkyl, or the groups $R^4$ and $R^5$ together with the carbon atom carrying them form a $(C_3$-$C_7)$-cycloalkane ring which is unsubstituted or substituted by one or more identical or different substituents selected from the series consisting of fluorine and $(C_1$-$C_4)$-alkyl;

$R^{11}$, $R^{12}$, $R^{13}$ and $R^{14}$ are independently of each other selected from the series consisting of hydrogen and $(C_1$-$C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1$-$C_4)$-alkyl, $(C_3$-$C_7)$-cycloalkyl, $(C_3$-$C_7)$-cycloalkyl-$(C_1$-$C_4)$-alkyl-, cyano and $(C_1$-$C_4)$-alkyl-O—;

V is $R^{11}$—O—, and in this case G and M are not present, or

V is selected from the series consisting of —N($R^{14}$)—, —N($R^{14}$)—$(C_1$-$C_4)$-alkyl- and —O—$(C_1$-$C_4)$-alkyl-, and in this case G is selected from the series consisting of a direct bond and phenylene which is unsubstituted or substituted by one or more identical or different substituents selected from the series consisting of halogen, $(C_1$-$C_4)$-alkyl, cyano and $(C_1$-$C_4)$-alkyl-O—, provided that G is not a direct bond if V is —N($R^{14}$)—, and M is selected from the series consisting of $R^{11}$—O—C(O)— and $R^{12}$—N($R^{13}$)—C(O)—;

wherein all alkyl groups are unsubstituted or substituted by one or more fluorine substituents, and all cycloalkyl groups are unsubstituted or substituted by one or more identical or different substituents selected from the series consisting of fluorine and $(C_1$-$C_4)$-alkyl;

in any of its stereoisomeric forms or a mixture of stereoisomeric forms in any ratio, or a pharmaceutically acceptable salt thereof.

(3) A compound of the formula I according to one or more of subject-matters (1) and (2) wherein $R^1$ is selected from the series consisting of $(C_1$-$C_6)$-alkyl, $(C_3$-$C_7)$-cycloalkyl, Ar and Ar—$(C_1$-$C_4)$-alkyl-;

$R^2$ and $R^3$ are independently of each other selected from the series consisting of hydrogen, $(C_1$-$C_4)$-alkyl, Ar, Ar—$(C_1$-$C_4)$-alkyl-, $(C_1$-$C_4)$-alkyl-O—, $(C_3$-$C_7)$-cycloalkyl-O—, Ar—O— and Ar—$(C_1$-$C_4)$-alkyl-O—, or the groups $R^2$ and $R^3$, in case they are bonded to adjacent ring carbon atoms, together with the carbon atoms carrying them form a benzene ring which is unsubstituted or substituted by one or more identical or different substituents selected from the series consisting of halogen, $(C_1$-$C_4)$-alkyl, cyano and $(C_1$-$C_4)$-alkyl-O—;

$R^4$ and $R^5$ are independently of each other selected from the series consisting of hydrogen and $(C_1$-$C_6)$-alkyl, or the groups $R^4$ and $R^5$ together with the carbon atom carrying them form a $(C_3$-$C_7)$-cycloalkane ring which is unsubstituted or substituted by one or more identical or different substituents selected from the series consisting of fluorine and $(C_1$-$C_4)$-alkyl;

$R^{11}$, $R^{12}$, $R^{13}$ and $R^{14}$ are independently of each other selected from the series consisting of hydrogen and $(C_1$-$C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1$-$C_4)$-alkyl, $(C_3$-$C_7)$-cycloalkyl and $(C_1$-$C_4)$-alkyl-O—;

V is $R^{11}$—O—, and in this case G and M are not present, or

V is selected from the series consisting of —N($R^{14}$)— and —N($R^{14}$)—$(C_1$-$C_4)$-alkyl-, and in this case G is selected from the series consisting of a direct bond and phenylene which is unsubstituted or substituted by one or more identical or different substituents selected from the series consisting of halogen, $(C_1$-$C_4)$-alkyl and $(C_1$-$C_4)$-alkyl-O—, provided that G is not a direct bond if V is —N($R^{14}$)—, and M is selected from the series consisting of $R^{11}$—O—C(O)— and $R^{12}$—N($R^{13}$)—C(O)—;

wherein all alkyl groups are unsubstituted or substituted by one or more fluorine substituents, and all cycloalkyl groups are unsubstituted or substituted by one or more identical or different substituents selected from the series consisting of fluorine and $(C_1$-$C_4)$-alkyl;

in any of its stereoisomeric forms or a mixture of stereoisomeric forms in any ratio, or a pharmaceutically acceptable salt thereof.

(4) A compound of the formula I according to one or more of subject-matters 1 to 3, wherein $R^1$ is selected from the series consisting of $(C_1$-$C_4)$-alkyl, Ar and Ar—$(C_1$-$C_4)$-alkyl-;

$R^2$ and $R^3$ are independently of each other selected from the series consisting of hydrogen, $(C_1$-$C_4)$-alkyl, Ar, Ar—$(C_1$-$C_4)$-alkyl-, and Ar—O—, or the groups $R^2$ and $R^3$, in case they are bonded to adjacent ring carbon atoms, together with the carbon atoms carrying them form a benzene ring which is unsubstituted or substituted by one or more identical or different substituents selected from the series consisting of halogen, $(C_1$-$C_4)$-alkyl and $(C_1$-$C_4)$-alkyl-O—;

R⁴ and R⁵ are independently of each other selected from the series consisting of hydrogen and $(C_1-C_6)$-alkyl, or the groups R⁴ and R⁵ together with the carbon atom carrying them form a $(C_3-C_7)$-cycloalkane ring which is unsubstituted or substituted by one or more identical or different substituents selected from the series consisting of fluorine and $(C_1-C_4)$-alkyl;

R¹¹ and R¹⁴ are independently of each other selected from the series consisting of hydrogen and $(C_1-C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1-C_4)$-alkyl, $(C_3-C_7)$-cycloalkyl and $(C_1-C_4)$-alkyl-O—;

V is R¹¹—O—, and in this case G and M are not present, or

V is selected from the series consisting of —N(R¹⁴)— and —N(R¹⁴)—$(C_1-C_4)$-alkyl-, and in this case G is selected from the series consisting of a direct bond and phenylene which is unsubstituted or substituted by one or more identical or different substituents selected from the series consisting of halogen, $(C_1-C_4)$-alkyl and $(C_1-C_4)$-alkyl-O—, provided that G is not a direct bond if V is —N(R¹⁴), and M is R¹¹—O—C(O)—;

wherein all alkyl groups are unsubstituted or substituted by one or more fluorine substituents, and all cycloalkyl groups are unsubstituted or substituted by one or more identical or different substituents selected from the series consisting of fluorine and $(C_1-C_4)$-alkyl;

in any of its stereoisomeric forms or a mixture of stereoisomeric forms in any ratio, or a pharmaceutically acceptable salt thereof.

(5) A compound of the formula I according to one or more of subject-matters (1) to (4), wherein R¹ is selected from the series consisting of $(C_1-C_4)$-alkyl, Ar and Ar—$(C_1-C_4)$-alkyl-;

R² and R³ are independently of each other selected from the series consisting of hydrogen, $(C_1-C_4)$-alkyl, Ar— and Ar—O—, or the groups R² and R³, in case they are bonded to adjacent ring carbon atoms, together with the carbon atoms carrying them form a benzene ring which is unsubstituted or substituted by one or more identical or different substituents selected from the series consisting of halogen and $(C_1-C_4)$-alkyl-;

R⁴ and R⁵ are independently of each other selected from the series consisting of hydrogen and $(C_1-C_6)$-alkyl, or the groups R⁴ and R⁵ together with the carbon atom carrying them form a $(C_3-C_7)$-cycloalkane ring which is unsubstituted or substituted by one or more fluorine substituents;

R¹¹ and R¹⁴ are independently of each other selected from the series consisting of hydrogen and $(C_1-C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1-C_4)$-alkyl, $(C_3-C_7)$-cycloalkyl and $(C_1-C_4)$-alkyl-O—;

V is R¹¹—O—, and in this case G and M are not present, or

V is selected from the series consisting of —N(R¹⁴)— and —N(R¹⁴)—$(C_1-C_4)$-alkyl-, and in this case G is selected from the series consisting of a direct bond and phenylene which is unsubstituted or substituted by one or more identical or different substituents selected from the series consisting of halogen, $(C_1-C_4)$-alkyl and $(C_1-C_4)$-alkyl-O—, provided that G is not a direct bond if V is —N(R¹⁴), and M is R¹¹—O—C(O)—;

wherein all alkyl groups are unsubstituted or substituted by one or more fluorine substituents;

in any of its stereoisomeric forms or a mixture of stereoisomeric forms in any ratio, or a pharmaceutically acceptable salt thereof.

(6) A compound of the formula I according to one or more of subject-matters (1) to (5), which is selected from the series consisting of 2-[5-(4-Chloro-phenyl)-1-(2,4-dichloro-phenyl)-4-methyl-1H-pyrazol-3-ylmethoxy]-2-methyl-propionic acid,

[5-(4-Chloro-phenyl)-1-(2,4-dichloro-phenyl)-4-methyl-1H-pyrazol-3-ylmethoxy]-acetic acid, 1-[5-(4-Chloro-phenyl)-1-(2,4-dichloro-phenyl)-4-methyl-1H-pyrazol-3-ylmethoxy]-cyclopentanecarboxylic acid, 2-[1-(2,4-Dichloro-phenyl)-4-methyl-5-(4-trifluoromethyl-phenyl)-1H-pyrazol-3-ylmethoxy]-2-methyl-propionic acid, 2-[1-(2-Chloro-phenyl)-4-methyl-5-(4-trifluoromethyl-phenyl)-1H-pyrazol-3-ylmethoxy]-2-methyl-propionic acid, 2-[1-(4-Chloro-phenyl)-4-methyl-5-(4-trifluoromethyl-phenyl)-1H-pyrazol-3-ylmethoxy]-2-methyl-propionic acid, 2-[5-(4-Chloro-phenyl)-1-(2,4-dichloro-phenyl)-4-methyl-1H-pyrazol-3-ylmethoxy]-butyric acid, 2-[5-(4-Chloro-phenyl)-1-(2,4-dichloro-phenyl)-4-methyl-1H-pyrazol-3-ylmethoxy]-propionic acid, 4-({2-[5-(4-Chloro-phenyl)-1-(2,4-dichloro-phenyl)-4-methyl-1H-pyrazol-3-ylmethoxy]-2-methyl-propionylamino}-methyl)-benzoic acid, 4-({2-[1-(2,4-Dichloro-phenyl)-4-methyl-5-(4-trifluoromethyl-phenyl)-1H-pyrazol-3-ylmethoxy]-2-methyl-propionylamino}-methyl)-benzoic acid, 4-({2-[5-(4-Chloro-phenyl)-1-(2,4-dichloro-phenyl)-4-methyl-1H-pyrazol-3-ylmethoxy]-acetylamino}-methyl)-benzoic acid, 4-({2-[5-(4-Chloro-phenyl)-1-(2,4-dichloro-phenyl)-4-methyl-1H-pyrazol-3-ylmethoxy]-butyrylamino}-methyl)-benzoic acid, 4-({2-[1-(2-Chloro-phenyl)-4-methyl-5-(4-trifluoromethyl-phenyl)-1H-pyrazol-3-ylmethoxy]-2-methyl-propionylamino}-methyl)-benzoic acid, 4-({2-[1-(4-Chloro-phenyl)-4-methyl-5-(4-trifluoromethyl-phenyl)-1H-pyrazol-3-ylmethoxy]-2-methyl-propionylamino}-methyl)-benzoic acid, 4-({2-[5-(4-Chloro-phenyl)-1-(2,4-dichloro-phenyl)-4-methyl-1H-pyrazol-3-ylmethoxy]-propionylamino}-methyl)-benzoic acid, 4-{2-[1-(2,4-Dichloro-phenyl)-4-methyl-5-(4-trifluoromethyl-phenyl)-1H-pyrazol-3-ylmethoxy]-propionylamino}-benzoic acid, 4-{2-[5-(4-Chloro-phenyl)-1-(2,4-dichloro-phenyl)-4-methyl-1H-pyrazol-3-ylmethoxy]-3-methyl-butyrylamino}-benzoic acid, 4-{2-[1-(4-Chloro-phenyl)-4-methyl-5-(4-trifluoromethyl-phenyl)-1H-pyrazol-3-ylmethoxy]-propionylamino}-benzoic acid, 4-[2-(3-Naphthalen-2-yl-1-phenyl-1H-pyrazol-4-ylmethoxy)-propionylamino]-benzoic acid, 4-{2-[1-(2-Chloro-phenyl)-4-methyl-5-(4-trifluoromethyl-phenyl)-1H-pyrazol-3-ylmethoxy]-propionylamino}-benzoic acid,
4-[2-(3,5-Dimethyl-1-phenyl-1H-pyrazol-4-ylmethoxy)-propionylamino]-benzoic acid,
4-[2-(1,3-Diphenyl-1H-pyrazol-4-ylmethoxy)-propionylamino]-benzoic acid,
4-{2-[1-Benzyl-3-(3-methoxy-phenyl)-1H-pyrazol-4-ylmethoxy]-propionylamino}-benzoic acid,
4-{2-[5-(4-Fluoro-phenoxy)-1-methyl-3-phenyl-1H-pyrazol-4-ylmethoxy]-propionylamino}-benzoic acid,
4-[2-(2-Methyl-2H-indazol-3-ylmethoxy)-propionylamino]-benzoic acid,
4-{2-[3-(4-Cyclohexyl-phenyl)-1-phenyl-1H-pyrazol-4-ylmethoxy]-propionylamino}-benzoic acid,
4-[2-(1-Phenyl-3-thiophen-2-yl-1H-pyrazol-4-ylmethoxy)-propionylamino]-benzoic acid, and
4-[2-(1,5-Diphenyl-1H-pyrazol-3-ylmethoxy)-propionylamino]-benzoic acid,
in any of its stereoisomeric forms or a mixture of stereoisomeric forms in any ratio, or a pharmaceutically acceptable salt thereof.
(7) A compound of the formula I or a pharmaceutically acceptable salt thereof according to one or more of subject-matters (1) to (6) for use as medicament.
(8) A compound of the formula I or a pharmaceutically acceptable salt thereof according to one or more of subject-matters (1) to (6) for use in the treatment of a disease responsive to the inhibition of the LPA receptor LPAR5 or the reduction or inhibition of platelet aggregation or thrombus formation or the reduction or inhibition of activation of mast cells or the reduction or inhibition of activation of microglial cells.
(9) A compound of the formula I or a pharmaceutically acceptable salt thereof according to one or more of subject-matters (1) to (6) for use in the treatment of thromboembolic diseases, deep vein thrombosis, venous or arterial thromboembolism, thrombophlebitis, coronary or cerebral arterial thrombosis, cerebral embolism, renal embolism, pulmonary embolism, disseminated intravascular coagulation, cardiovascular disorders, transient ischemic attacks, strokes, acute myocardial infarction, unstable angina, chronic stable angina, peripheral vascular disease, preeclampsia/eclampsia, thrombotic cytopenic purpura, inflammatory disorders, hyperalgesia, asthma, multiple sclerosis, inflammatory pain, angiogenesis, atherothrombosis, allergic responses, or restenoses.
(10) A compound of the formula I or a pharmaceutically acceptable salt thereof according to one or more of subject-matters (1) to (6) for use in the treatment of abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication, bypass grafting of the coronary or peripheral arteries, vessel luminal narrowing, restenosis post coronary venous angioplasty, maintenance of vascular access patency in long-term hemodialysis patients, pathologic thrombus formation occurring in the veins of the lower extremities following abdominal, knee or hip surgery, a risk of pulmonary thromboembolism, or disseminated systemic intravascular coagulatopathy occurring in vascular systems during septic shock, viral infections or cancer.
(11) A compound of the formula I or a pharmaceutically acceptable salt thereof according to one or more of subject-matters (1) to (6) for use in the treatment of inflammatory pain, asthma, angiogenesis, demyelating diseases of the central nervous system or the peripheral nervous system, multiple sclerosis, transverse myelitis, optic neuritis, Devic's disease, Guillain-Barre syndrome or chronic inflammatory demyelinating polyneuropathy.
(12) A pharmaceutical composition comprising a compound of the formula I or a pharmaceutically acceptable salt thereof according to one or more of subject-matters (1) to (6), and a pharmaceutically acceptable carrier.

EXAMPLES

When in the final step of the synthesis of a compound an acid such as trifluoroacetic acid or acetic acid was used, for example when trifluoroacetic acid was employed to an acid-labile protecting group, for example a tBu group, or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt, formic acid salt or trifluoroacetic acid salt or hydrochloric acid salt. Likewise starting materials or intermediates bearing a basic center like for example a basic nitrogen were either obtained and used as free base or in salt form like, for example, a trifluoroacetic acid salt, a hydrobromic acid salt, a sulfuric acid salt, or a hydrochloric acid salt. Room temperature means a temperature of about 20° C. to 25° C.

Abbreviations
Acetonitrile MeCN
tert-Butyl tBu
N,N-Dimethylformamide DMF
N-Ethylmorpholine NEM
Tetrahydrofuran THF
Trifluoroacetic acid TFA Example 1

2-[5-(4-Chloro-phenyl)-1-(2,4-dichloro-phenyl)-4-methyl-1H-pyrazol-3-ylmethoxy]-2-methyl-propionic acid

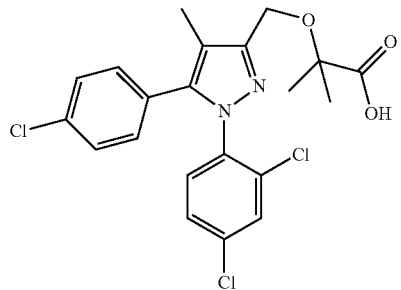 [SMILES: Cc1c(COC(C)(C)C(=O)O)nn(-c2ccc(Cl)cc2Cl)c1-c1ccc(Cl)cc1]

(i) [5-(4-Chloro-phenyl)-1-(2,4-dichloro-phenyl)-4-methyl-1H-pyrazol-3-yl]-methanol To a solution of 5 g of 5-(4-Chloro-phenyl)-1-(2,4-dichloro-phenyl)-4-methyl-1H-pyrazole-3-carboxylic acid in 130 ml of THF, were added dropwise 40 ml of a 1M solution of borane in THF at room temperature. Then the reaction mixture was heated to reflux for 10 h. The reaction mixture was cooled to room temperature and 20 ml of methanol were carefully added. The solvents were removed under reduced pressure and the residue was dissolved in ethyl acetate. The organic layer was washed with 1 M hydrochloric acid, saturated sodium chloride solution and saturated sodium hydrogen carbonate solution. The combined organic layers were dried over MgSO$_4$, filtered and concentrated under reduced pressure. The product was obtained as a white solid and used without further purification.

Yield: 4.6 g.

(ii) 2-[5-(4-Chloro-phenyl)-1-(2,4-dichloro-phenyl)-4-methyl-1H-pyrazol-3-ylmethoxy]-2-methyl-propionic acid ethyl ester To a solution of 1.6 g of [5-(4-Chloro-phenyl)-1-(2,4-dichloro-phenyl)-4-methyl-1H-pyrazol-3-yl]-methanol in 15 ml of DMF were added 870 mg of sodium hydride (60% in mineral oil) at room temperature. After 15 min 1.6 g of tetrabutylammonium iodide and 3.4 g of 2-Bromo-2-methyl-propionic acid ethyl ester were added and the reaction mixture was stirred for 16 h at room temperature. After dilution with saturated aqueous sodium hydrogen carbonate solution the reaction mixture was filtered through a chem Elut® cartridge by eluting with ethyl acetate The solvents were removed under reduced pressure and the crude product was purified by chromatography on silica gel eluting with a gradient of n-heptane/ethyl acetate. The fractions containing the product were combined and the solvent evaporated under reduced pressure. Yield: 1.3 g.

(iii) 2-[5-(4-Chloro-phenyl)-1-(2,4-dichloro-phenyl)-4-methyl-1H-pyrazol-3-ylmethoxy]-2-methyl-propionic acid To a solution of 735 mg of 2-[5-(4-Chloro-phenyl)-1-(2,4-dichloro-phenyl)-4-methyl-1H-pyrazol-3-ylmethoxy]-2-methyl-propionic acid ethyl ester in 10 ml THF was added a solution of 51 mg of LiOH in 1 ml water at room temperature. After 16 h the mixture was brought to pH 2 by addition of 1 M hydrochloric acid. The reaction mixture was concentrated under reduced pressure and the aqueous layer was extracted with dichloromethane. The combined organic phases were dried over MgSO$_4$ and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. Yield: 677 mg.

MS (ES-): m/e=451, chloro pattern.

Example 2

[5-(4-Chloro-phenyl)-1-(2,4-dichloro-phenyl)-4-methyl-1H-pyrazol-3-ylmethoxy]-acetic acid

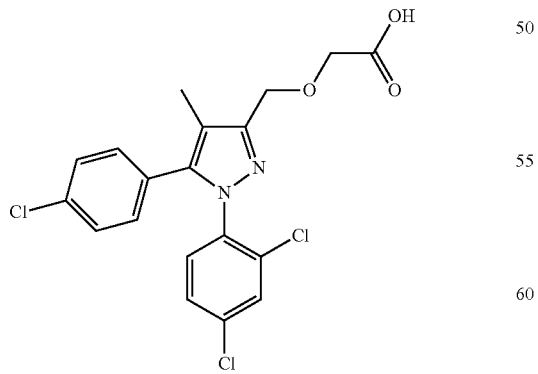

The title compound was prepared analogously as described in example 1.

MS (ES-): m/e=423, chloro pattern.

Example 3

1-[5-(4-Chloro-phenyl)-1-(2,4-dichloro-phenyl)-4-methyl-1H-pyrazol-3-ylmethoxy]-cyclopentanecarboxylic acid

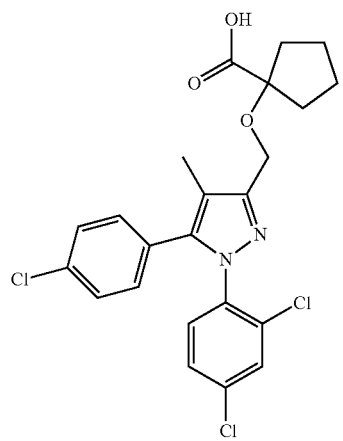 [SMILES: Cc1c(COC2(C(=O)O)CCCC2)nn(-c2ccc(Cl)cc2Cl)c1-c1ccc(Cl)cc1]

The title compound was prepared analogously as described in example 1.

MS (ES-): m/e=477, chloro pattern.

Example 4

2-[1-(2,4-Dichloro-phenyl)-4-methyl-5-(4-trifluoromethyl-phenyl)-1H-pyrazol-3-ylmethoxy]-2-methyl-propionic acid

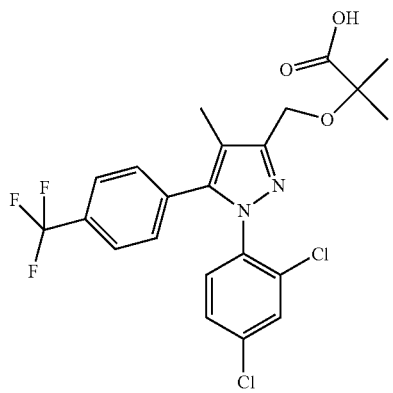 [SMILES: Cc1c(COC(C)(C)C(=O)O)nn(-c2ccc(Cl)cc2Cl)c1-c1ccc(C(F)(F)F)cc1]

(i) Lithium 3-ethoxycarbonyl-2-methyl-3-oxo-1-(4-trifluoromethyl-phenyl)-propan-1-olate To a solution of 118 ml of lithium bis(trimethylsilyl)amide (Lithium Hexamethyldisilazide; 0.9 M in methylcyclohexane) was added dropwise over 15 min, 20 g of 1-(4-Trifluoromethyl-phenyl)-propan-1-one in 51 ml methylcyclohexane at while maintaining the reaction mixture at 15-25° C. After stirring for 2 h, 15 ml of diethyl oxalate were added dropwise over 30 min and the reaction mixture was stirred for 16 h. Then, the precipitated product was collected by filtration and washed with n-heptane. The isolated crude product was used in the next reaction step after drying in vacuo. Yield: 19 g.

(ii) 1-(2,4-Dichloro-phenyl)-4-methyl-5-(4-trifluoromethyl-phenyl)-1H-pyrazole-3-carboxylic acid A solution of 10 g of Lithium 3-ethoxycarbonyl-2-methyl-3-oxo-1-(4-trifluoromethyl-phenyl)-propan-1-olate, 6.9 g of (2,4-Dichloro-phenyl)-hydrazine hydrochloride and 74 ml of sulfuric acid (50%) in 184 ml of ethanol was heated to reflux for 7 h. After cooling to room temperature the organic solvents were removed under reduced pressure and the residue was diluted with 100 ml of water and extracted with ethyl acetate. The combined organic layers were dried over $MgSO_4$ and the solvent was removed under reduced pressure. The residue was dissolved in 100 ml THF and a solution of 1.4 g of LiOH in 20 ml water was added at room temperature. The reaction mixture was heated to 60° C. for 7 h. Then, after cooling to room temperature the mixture was acidified to pH 1 by addition of half-concentrated hydrochloric acid. The precipitating product was collected by filtration and washed with water. The residue was codistilled twice with dichloromethane and twice with toluene. The isolated crude product was used in the next reaction step. Yield: 13 g.

(iii) [1-(2,4-Dichloro-phenyl)-4-methyl-5-(4-trifluoromethyl-phenyl)-1H-pyrazol-3-yl]-methanol To a solution of 4.5 g of 1-(2,4-Dichloro-phenyl)-4-methyl-5-(4-trifluoromethyl-phenyl)-1H-pyrazole-3-carboxylic acid in 30 ml of THF, were added dropwise 43 ml of a 1M solution of borane in THF at room temperature. Then the reaction mixture was heated to reflux for 10 h. The reaction mixture was cooled to room temperature and 20 ml of methanol were carefully added. The solvents were removed under reduced pressure and the residue was dissolved in ethyl acetate. The organic layer was washed with 1 M hydrochloric acid, saturated sodium chloride solution and saturated sodium hydrogen carbonate solution. The organic layers were combined and dried over $MgSO_4$, filtered and concentrated under reduced pressure. The product was obtained as a white solid and was used without further purification.
Yield: 4.3 g.

(iv) 2-[1-(2,4-Dichloro-phenyl)-4-methyl-5-(4-trifluoromethyl-phenyl)-1H-pyrazol-3-ylmethoxy]-2-methyl-propionic acid ethyl ester To a solution of 2 g of [1-(2,4-Dichloro-phenyl)-4-methyl-5-(4-trifluoromethyl-phenyl)-1H-pyrazol-3-yl]-methanol in 15 ml of DMF were added 997 mg of sodium hydride (60% in mineral oil) at room temperature. After 15 min 1.8 g of tetrabutylammonium iodide and 2.9 g of 2-Bromo-2-methyl-propionic acid ethyl ester were added and the reaction mixture was stirred for 16 h at room temperature. After dilution with saturated aqueous sodium hydrogen carbonate solution the reaction mixture was filtered through a chem Elut® cartridge by eluting with ethyl acetate. The solvents were removed under reduced pressure and the crude product was purified by chromatography on silica gel eluting with a gradient of n-heptane/ethyl acetate. The fractions containing the product were combined and the solvent evaporated under reduced pressure. Yield: 1.3 g.

(v) 2-[1-(2,4-Dichloro-phenyl)-4-methyl-5-(4-trifluoromethyl-phenyl)-1H-pyrazol-3-ylmethoxy]-2-methyl-propionic acid To a solution of 1 g of 2-[1-(2,4-Dichloro-phenyl)-4-methyl-5-(4-trifluoromethyl-phenyl)-1H-pyrazol-3-yl-methoxy]-2-methyl-propionic acid ethyl ester in 6 ml THF was added a solution of 232 mg of LiOH in 1 ml water at room temperature. After 16 h the mixture was brought to pH 2 by addition of 1 M hydrochloric acid. The reaction mixture was concentrated under reduced pressure and the aqueous layer was extracted with dichloromethane. The combined organic phases were dried over $MgSO_4$ and the solvents were removed under reduced pressure. The residue was purified by preparative HPLC (C18 reverse phase column, elution with a water/MeCN gradient with 0.1% TFA). The fractions containing the product were evaporated and lyophilized to yield a yellow solid. Yield: 634 mg.

MS (ES-): m/e=485, chloro pattern.

Example 5

2-[1-(2-Chloro-phenyl)-4-methyl-5-(4-trifluoromethyl-phenyl)-1H-pyrazol-3-ylmethoxy]-2-methyl-propionic acid

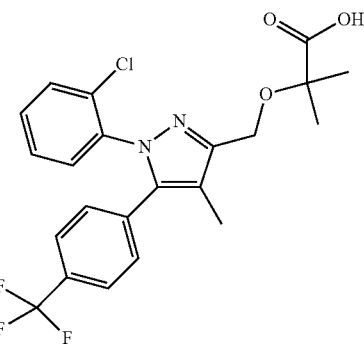

The title compound was prepared analogously as described in example 5.

MS (ES-): m/e=451, chloro pattern.

Example 6

2-[1-(4-Chloro-phenyl)-4-methyl-5-(4-trifluoromethyl-phenyl)-1H-pyrazol-3-ylmethoxy]-2-methyl-propionic acid

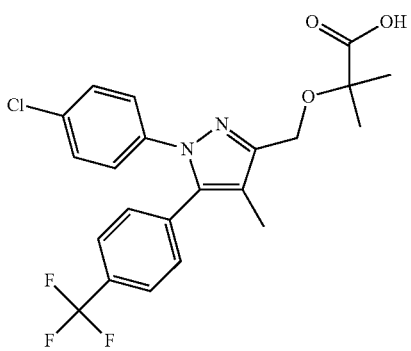 [SMILES: Cc1c(COC(C)(C)C(=O)O)nn(-c2ccc(Cl)cc2)c1-c1ccc(C(F)(F)F)cc1]

The title compound was prepared analogously as described in example 5.

MS (ES-): m/e=451, chloro pattern.

Example 7

2-[5-(4-Chloro-phenyl)-1-(2,4-dichloro-phenyl)-4-methyl-1H-pyrazol-3-ylmethoxy]-butyric acid

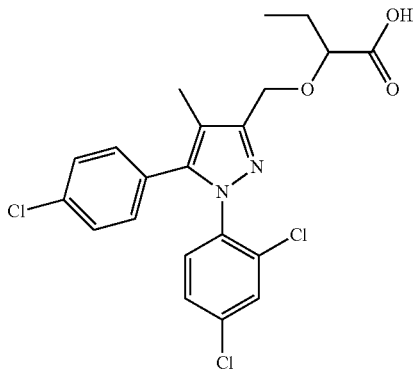 [SMILES: CCC(OCc1nn(-c2ccc(Cl)cc2Cl)c(-c2ccc(Cl)cc2)c1C)C(=O)O]

The title compound was prepared analogously as described in example 5.

MS (ES-): m/e=452, chloro pattern.

Example 8

2-[5-(4-Chloro-phenyl)-1-(2,4-dichloro-phenyl)-4-methyl-1H-pyrazol-3-ylmethoxy]-propionic acid

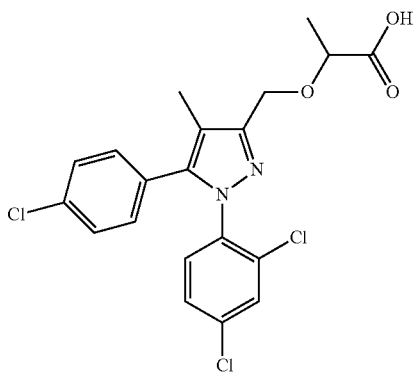 [SMILES: Cc1c(COC(C)C(=O)O)nn(-c2ccc(Cl)cc2Cl)c1-c1ccc(Cl)cc1]

The title compound was prepared analogously as described in example 5.

MS (ES-): m/e=439, chloro pattern.

Example 9

4-({2-[5-(4-Chloro-phenyl)-1-(2,4-dichloro-phenyl)-4-methyl-1H-pyrazol-3-ylmethoxy]-2-methyl-propionylamino}-methyl)-benzoic acid

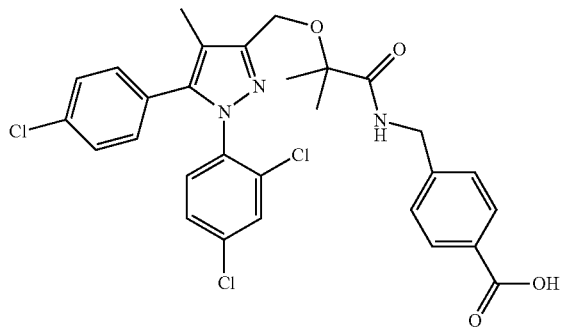 [SMILES: Cc1c(COC(C)(C)C(=O)NCc2ccc(C(=O)O)cc2)nn(-c2ccc(Cl)cc2Cl)c1-c1ccc(Cl)cc1]

(i) [5-(4-Chloro-phenyl)-1-(2,4-dichloro-phenyl)-4-methyl-1H-pyrazol-3-yl]-methanol To a solution of 5 g of 5-(4-Chloro-phenyl)-1-(2,4-dichloro-phenyl)-4-methyl-1H-pyrazole-3-carboxylic acid in 130 ml of THF, were added dropwise 40 ml of a 1M solution of borane in THF at room temperature. Then, the reaction mixture was heated to reflux for 10 h. The reaction mixture was cooled to room temperature and 20 ml of methanol were carefully added. The solvents were removed under reduced pressure and the residue was dissolved in ethyl acetate. The organic layer was washed with 1 M hydrochloric acid saturated sodium chloride solution and saturated sodium hydrogen carbonate solution. The combined organic layers were dried over MgSO$_4$, filtered and concentrated under reduced pressure. The product was obtained as a white solid and was used without further purification. Yield: 4.6 g.

(ii) 2-[5-(4-Chloro-phenyl)-1-(2,4-dichloro-phenyl)-4-methyl-1H-pyrazol-3-ylmethoxy]-2-methyl-propionic acid ethyl ester To a solution of 1.6 g of [5-(4-Chloro-phenyl)-1-(2,4-dichloro-phenyl)-4-methyl-1H-pyrazol-3-yl]-methanol in 15 ml of DMF were added 870 mg of sodium hydride (60% in mineral oil) at room temperature. After 15 min, 1.6 g of tetrabutylammonium iodide and 3.4 g of 2-Bromo-2-methyl-propionic acid ethyl ester were added and the reaction mixture was stirred for 16 h at room temperature. After dilution with saturated aqueous sodium hydrogen carbonate solution the reaction mixture was filtered through a chem Elut® cartridge by eluting with ethyl acetate. The solvents were removed under reduced pressure and the crude product was purified by chromatography on silica gel eluting with a gradient of n-heptane/ethyl acetate. The fractions containing the product were combined and the solvent evaporated under reduced pressure. Yield: 1.3 g.

(iii) 2-[5-(4-Chloro-phenyl)-1-(2,4-dichloro-phenyl)-4-methyl-1H-pyrazol-3-ylmethoxy]-2-methyl-propionic acid To a solution of 1.3 g of 2-[5-(4-Chloro-phenyl)-1-(2,4-dichloro-phenyl)-4-methyl-1H-pyrazol-3-ylmethoxy]-2-methyl-propionic acid ethyl ester in 10 ml THF was added a solution of 130 mg of LiOH in 3 ml water at room temperature. After 5 h the mixture was brought to pH 2 by addition of 1 M hydrochloric acid. The reaction mixture was concentrated under reduced pressure and the aqueous layer was extracted with dichloromethane. The combined organic phases were dried over MgSO$_4$ and the solvents were removed under reduced pressure. The isolated crude product was used in the next reaction step. Yield: 1.5 g.

(iv) 4-({2-[5-(4-Chloro-phenyl)-1-(2,4-dichloro-phenyl)-4-methyl-1H-pyrazol-3-ylmethoxy]-2-methyl-propionylamino}-methyl)-benzoic acid To a solution of 710 mg of 2-[5-(4-Chloro-phenyl)-1-(2,4-dichloro-phenyl)-4-methyl-1H-pyrazol-3-ylmethoxy]-2-methyl-propionic acid in 5 ml of DMF, 360 mg of N-(3-dimethylaminopropyl)-N'-ethylcarbodiimide hydrochloride (EDC), 345 mg of pentafluorophenol and 392 mg of NEM were added and the reaction mixture was stirred for 3 h at room temperature. Then, 353 mg of 4-Aminomethyl-benzoic acid and 540 mg of NEM in 5 ml of DMF were added. After 16 h the reaction mixture was diluted with water and filtered through a chem Elut® cartridge by eluting with ethyl acetate. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. Yield: 288 mg.

MS (ES-): m/e=586, chloro pattern.

Example 10

4-({2-[1-(2,4-Dichloro-phenyl)-4-methyl-5-(4-trifluoromethyl-phenyl)-1H-pyrazol-3-ylmethoxy]-2-methyl-propionylamino}-methyl)-benzoic acid

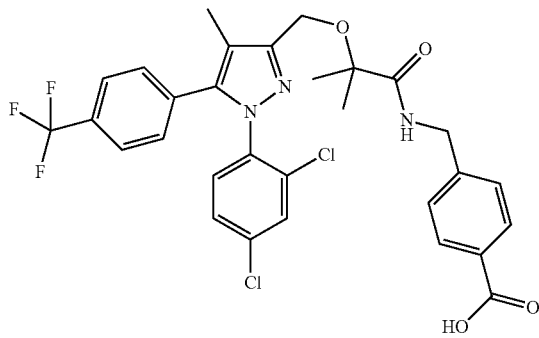 [SMILES: Cc1c(COC(C)(C)C(=O)NCc2ccc(C(=O)O)cc2)nn(-c2ccc(Cl)cc2Cl)c1-c1ccc(C(F)(F)F)cc1]

(i) Lithium 3-ethoxycarbonyl-2-methyl-3-oxo-1-(4-trifluoromethyl-phenyl)-propan-1-olate To a solution of 118 ml of lithium bis(trimethylsilyl)amide (Lithium Hexamethyldisilazide; 0.9 M in methylcyclohexane) was added dropwise over 15 min 20 g of 1-(4-Trifluoromethyl-phenyl)-propan-1-one in 51 ml methylcyclohexane at while maintaining the reaction mixture at 15-25° C. After stirring for 2 h, 15 ml of diethyl oxalate were added dropwise over 30 min and the reaction mixture was stirred for 16 h. Then, the precipitated product was collected by filtration and washed with n-heptane. The isolated crude product was used in the next reaction step after drying in vacuo. Yield: 19 g.

(ii) 1-(2,4-Dichloro-phenyl)-4-methyl-5-(4-trifluoromethyl-phenyl)-1H-pyrazole-3-carboxylic acid A solution of 10 g of Lithium 3-ethoxycarbonyl-2-methyl-3-oxo-1-(4-trifluoromethyl-phenyl)-propan-1-olate, 6.9 g of (2,4-Dichloro-phenyl)-hydrazine hydrochloride and 74 ml of sulfuric acid (50%) in 184 ml of ethanol was heated to reflux for 7 h. After cooling to room temperature the organic solvents were removed under reduced pressure and the residue was diluted with 100 ml of water and extracted with ethyl acetate. The combined organic layers were dried over MgSO$_4$ and the solvent was removed under reduced pressure. The residue was dissolved in 100 ml THF and a solution of 1.4 g of LiOH in 20 ml water was added at room temperature. The reaction mixture was heated to 60° C. for 7 h. Then, after cooling to room temperature the mixture was acidified to pH 1 by addition of half-concentrated hydrochloric acid.

The precipitating product was collected by filtration and washed with water. The residue was codistilled twice with dichloromethane and twice with toluene. The isolated crude product was used in the next reaction step. Yield: 13 g.

(iii) [1-(2,4-Dichloro-phenyl)-4-methyl-5-(4-trifluoromethyl-phenyl)-1H-pyrazol-3-yl]-methanol To a solution of 4.5 g of 1-(2,4-Dichloro-phenyl)-4-methyl-5-(4-trifluoromethyl-phenyl)-1H-pyrazole-3-carboxylic acid in 30 ml of THF, were added dropwise 43 ml of a 1M solution of borane in THF at room temperature. Then the reaction mixture was heated to reflux for 10 h. The reaction mixture was cooled to room temperature and 20 ml of methanol were carefully added. The solvents were removed under reduced pressure and the residue was dissolved in ethyl acetate. The organic layer was washed with 1 M hydrochloric acid, saturated sodium chloride solution and saturated sodium hydrogen carbonate solution. The combined organic layers were dried over MgSO$_4$, filtered and concentrated under reduced pressure. The product was obtained as a white solid and used without further purification. Yield: 4.3 g.

(iv) 2-[1-(2,4-Dichloro-phenyl)-4-methyl-5-(4-trifluoromethyl-phenyl)-1H-pyrazol-3-ylmethoxy]-2-methyl-propionic acid ethyl ester To a solution of 2 g of [1-(2,4-Dichloro-phenyl)-4-methyl-5-(4-trifluoromethyl-phenyl)-1H-pyrazol-3-yl]-methanol in 12 ml of DMF were added 997 mg of sodium hydride (60% in mineral oil) at room temperature. After 15 min, 1.8 g of tetrabutylammonium iodide and 2.9 g of 2-Bromo-2-methyl-propionic acid ethyl ester were added and the reaction mixture was stirred for 16 h at room temperature. After dilution with saturated aqueous sodium hydrogen carbonate solution the reaction mixture was filtered through a chem Elut® cartridge by eluting with ethyl acetate. The solvents were removed under reduced pressure and the crude product was purified by chromatography on silica gel eluting with a gradient of n-heptane/ethyl acetate. The fractions containing the product were combined and the solvent evaporated under reduced pressure. Yield: 735 mg.

(v) 2-[1-(2,4-Dichloro-phenyl)-4-methyl-5-(4-trifluoromethyl-phenyl)-1H-pyrazol-3-ylmethoxy]-2-methyl-propionic acid To a solution of 735 mg of 2-[1-(2,4-Dichloro-phenyl)-4-methyl-5-(4-trifluoromethyl-phenyl)-1H-pyrazol-3-ylmethoxy]-2-methyl-propionic acid ethyl ester in 5 ml THF was added a solution of 51 mg of LiOH in 1 ml water at room temperature. After 5 h the mixture was brought to pH 2 by addition of 1 M hydrochloric acid. The reaction mixture was concentrated under reduced pressure and the aqueous layer was extracted with dichloromethane. The combined organic phases were dried over MgSO$_4$ and the solvents were removed under reduced pressure. The isolated crude product was used in the next reaction step. Yield: 677 mg.

(vi) 4-({2-[1-(2,4-Dichloro-phenyl)-4-methyl-5-(4-trifluoromethyl-phenyl)-1H-pyrazol-3-ylmethoxy]-2-methyl-propionylamino}-methyl)-benzoic acid To a solution of 600 mg of 2-[1-(2,4-Dichloro-phenyl)-4-methyl-5-(4-trifluoromethyl-phenyl)-1H-pyrazol-3-ylmethoxy]-2-methyl-propionic acid in 9 ml of DMF, 283 mg of N-(3-dimethylaminopropyl)-N'-ethylcarbodiimide hydrochloride (EDC), 271 mg of pentafluorophenol and 300 mg of NEM was added and the reaction mixture was stirred for 3 h at room temperature. Then, 278 mg of 4-Aminomethyl-benzoic acid and 424 mg of NEM in 10 ml of DMF were added. After 16 h the reaction mixture was diluted with water and filtered through a chem Elut® cartridge by eluting with ethyl acetate. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. Yield: 204 mg.

MS (ES-): m/e=618, chloro pattern.

Example 11

4-({2-[5-(4-Chloro-phenyl)-1-(2,4-dichloro-phenyl)-4-methyl-1H-pyrazol-3-ylmethoxy]-acetylamino}-methyl)-benzoic acid

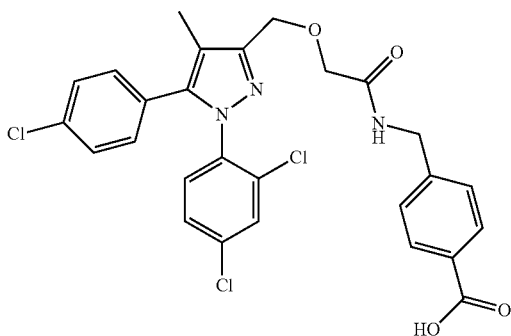 [SMILES: Cc1c(COCC(=O)NCc2ccc(C(=O)O)cc2)nn(-c2ccc(Cl)cc2Cl)c1-c1ccc(Cl)cc1]

The title compound was prepared analogously as described in example 11.
MS (ES-): m/e=556, chloro pattern.

Example 12

4-({2-[5-(4-Chloro-phenyl)-1-(2,4-dichloro-phenyl)-4-methyl-1H-pyrazol-3-ylmethoxy]-butyrylamino}-methyl)-benzoic acid

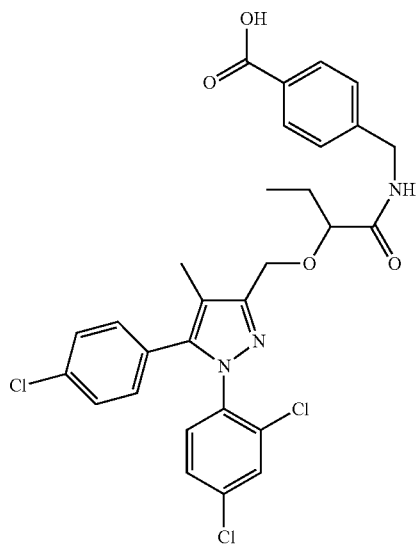 [SMILES: CCC(OCc1nn(-c2ccc(Cl)cc2Cl)c(-c2ccc(Cl)cc2)c1C)C(=O)NCc1ccc(C(=O)O)cc1]

The title compound was prepared analogously as described in example 11.
MS (ES-): m/e=586, chloro pattern.

Example 13

4-({2-[1-(2-Chloro-phenyl)-4-methyl-5-(4-trifluoromethyl-phenyl)-1H-pyrazol-3-ylmethoxy]-2-methyl-propionylamino}-methyl)-benzoic acid

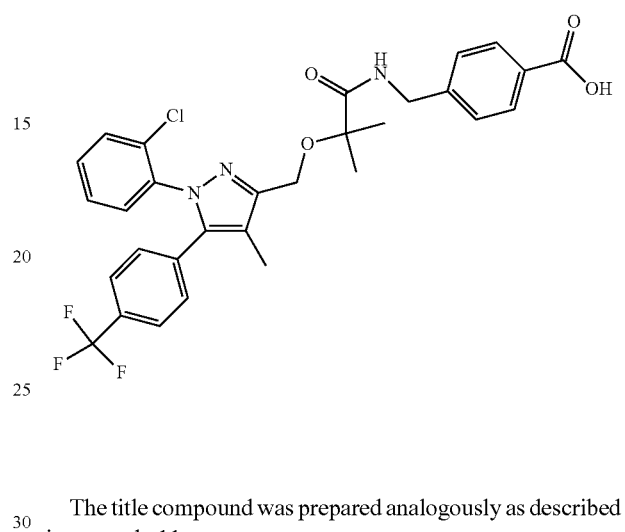

The title compound was prepared analogously as described in example 11.
MS (ES-): m/e=584, chloro pattern.

Example 14

4-({2-[1-(4-Chloro-phenyl)-4-methyl-5-(4-trifluoromethyl-phenyl)-1H-pyrazol-3-ylmethoxy]-2-methyl-propionylamino}-methyl)-benzoic acid

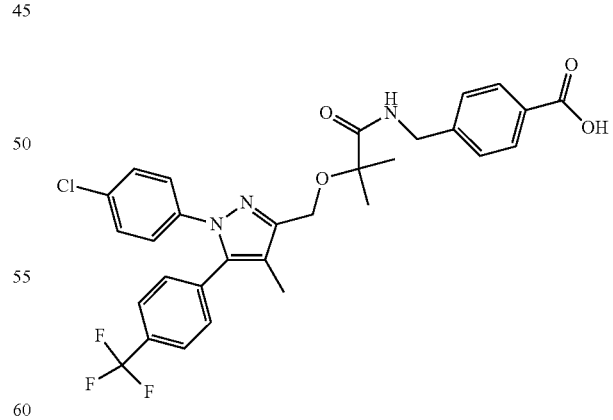

The title compound was prepared analogously as described in example 11.
MS (ES-): m/e=584, chloro pattern.

Example 15

4-({2-[5-(4-Chloro-phenyl)-1-(2,4-dichloro-phenyl)-4-methyl-1H-pyrazol-3-ylmethoxy]-propionylamino}-methyl)-benzoic acid

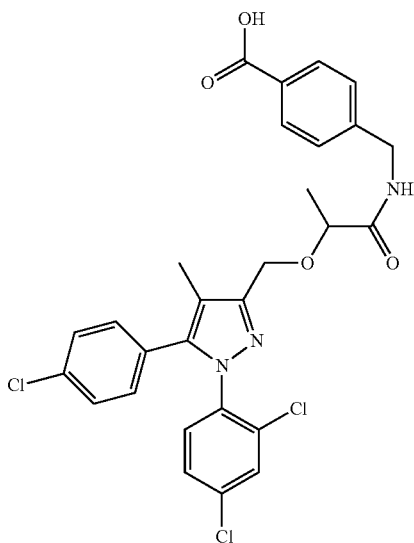 [SMILES: Cc1c(COC(C)C(=O)NCc2ccc(C(=O)O)cc2)nn(-c2ccc(Cl)cc2Cl)c1-c1ccc(Cl)cc1]

The title compound was prepared analogously as described in example 11.

MS (ES-): m/e=570, chloro pattern.

Example 16

4-{2-[1-(2,4-Dichloro-phenyl)-4-methyl-5-(4-trifluoromethyl-phenyl)-1H-pyrazol-3-ylmethoxy]-propionylamino}-benzoic acid

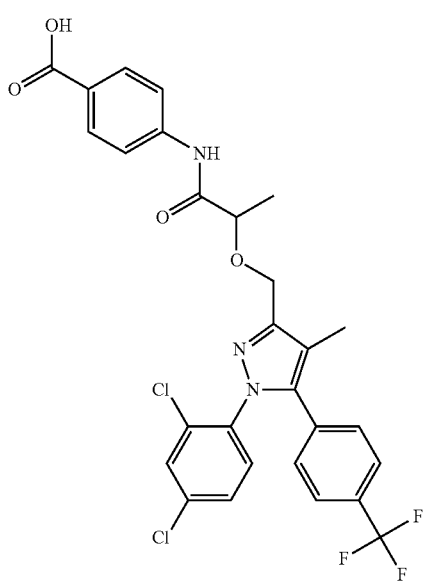 [SMILES: Cc1c(COC(C)C(=O)Nc2ccc(C(=O)O)cc2)nn(-c2ccc(Cl)cc2Cl)c1-c1ccc(C(F)(F)F)cc1]

(i) 4-(2-Bromo-propionylamino)-benzoic acid methyl ester

To a solution of 1.1 g of 4-Amino-benzoic acid methyl ester in 17 ml of toluene were added 2.2 ml of pyridine and 1.5 g of 2-Bromo-propionyl bromide at room temperature. After 16 h the reaction mixture was diluted with water and filtered through a chem Elut® cartridge by eluting with ethyl acetate. The solvents were removed under reduced pressure and the crude product was purified by chromatography on silica gel eluting with a gradient of n-heptane/ethyl acetate. The fractions containing the product were combined and the solvent evaporated under reduced pressure. Yield: 2 g.

(ii) 4-{2-[1-(2,4-Dichloro-phenyl)-4-methyl-5-(4-trifluoromethyl-phenyl)-1H-pyrazol-3-ylmethoxy]-propionylamino}-benzoic acid To a solution of 100 mg of [1-(2,4-Dichloro-phenyl)-4-methyl-5-(4-trifluoromethyl-phenyl)-1H-pyrazol-3-yl]-methanol in 3 ml of DMF were added 54 mg of sodium hydride (60% in mineral oil) at room temperature. After 15 min, 100 mg of tetrabutylammonium iodide and 117 mg of 4-(2-Bromo-propionylamino)-benzoic acid methyl ester were added and the reaction mixture was heated to 80° C. for 8 h. After cooling to room temperature and dilution with 1 M aqueous hydrochloric acid the reaction mixture was filtered through a chem Elut® cartridge by eluting with ethyl acetate. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. Yield: 24 mg.

MS (ES-): m/e=590, chloro pattern.

Example 17

4-{2-[5-(4-Chloro-phenyl)-1-(2,4-dichloro-phenyl)-4-methyl-1H-pyrazol-3-ylmethoxy]-3-methyl-butyrylamino}-benzoic acid

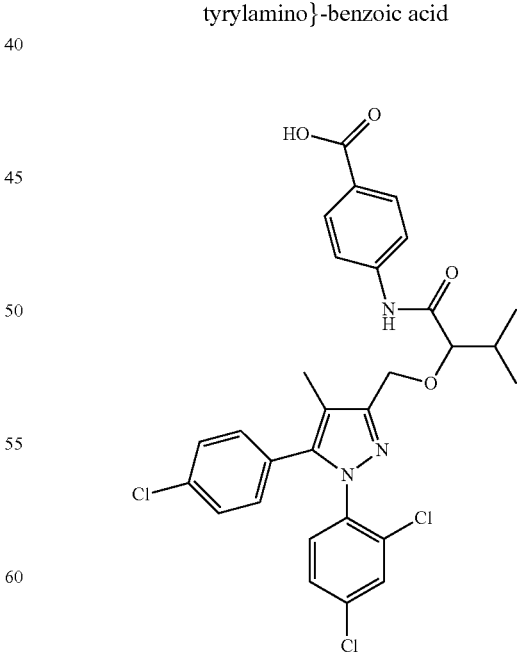

The title compound was prepared analogously as described in example 16.

MS (ES-): m/e=584, chloro pattern.

Example 18

4-{2-[1-(4-Chloro-phenyl)-4-methyl-5-(4-trifluoromethyl-phenyl)-1H-pyrazol-3-ylmethoxy]-propionylamino}-benzoic acid

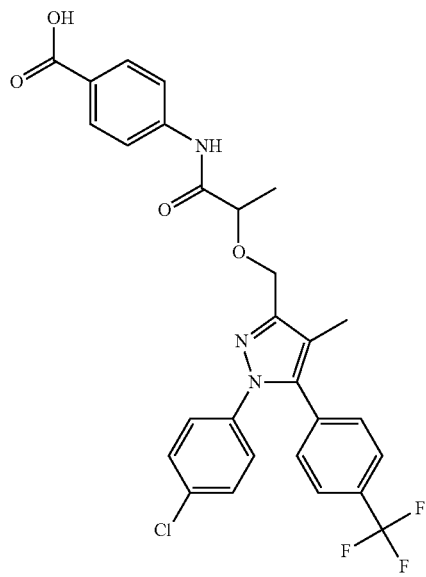 [SMILES: Cc1c(COC(C)C(=O)Nc2ccc(C(=O)O)cc2)nn(-c2ccc(Cl)cc2)c1-c1ccc(C(F)(F)F)cc1]

The title compound was prepared analogously as described in example 16.

MS (ES-): m/e=556, chloro pattern.

Example 19

4-[2-(3-Naphthalen-2-yl-1-phenyl-1H-pyrazol-4-ylmethoxy)-propionylamino]-benzoic acid

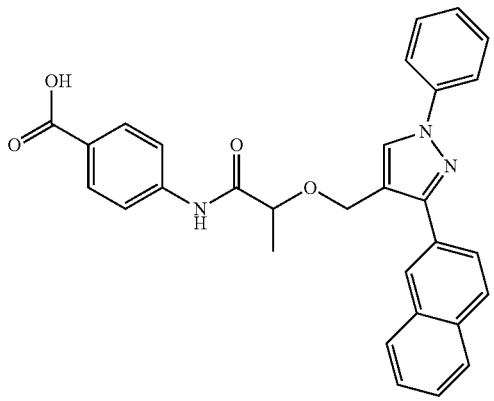 [SMILES: CC(OCc1cn(-c2ccccc2)nc1-c1ccc2ccccc2c1)C(=O)Nc1ccc(C(=O)O)cc1]

The title compound was prepared analogously as described in example 16.

MS (ES-): m/e=590.

Example 20

4-{2-[1-(2-Chloro-phenyl)-4-methyl-5-(4-trifluoromethyl-phenyl)-1H-pyrazol-3-ylmethoxy]-propionylamino}-benzoic acid

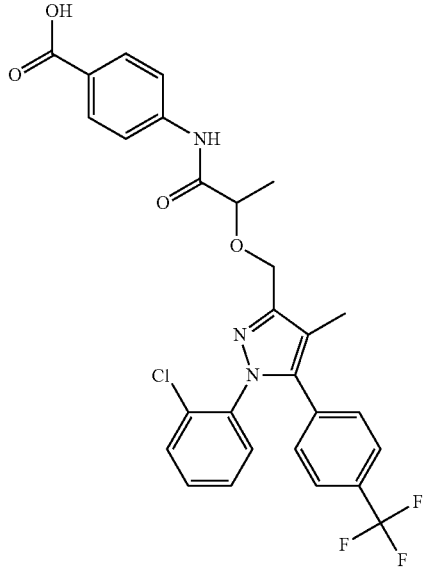 [SMILES: Cc1c(COC(C)C(=O)Nc2ccc(C(=O)O)cc2)nn(-c2ccccc2Cl)c1-c1ccc(C(F)(F)F)cc1]

The title compound was prepared analogously as described in example 16.

MS (ES-): m/e=556, chloro pattern.

Example 21

4-[2-(3,5-Dimethyl-1-phenyl-1H-pyrazol-4-ylmethoxy)-propionylamino]-benzoic acid

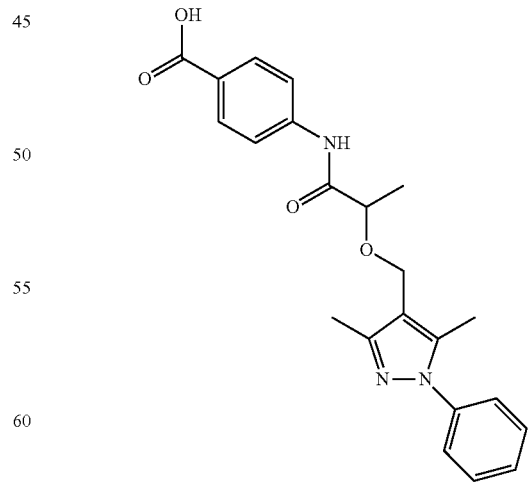

The title compound was prepared analogously as described in example 16.

MS (ES-): m/e=392.

Example 22

4-[2-(1,3-Diphenyl-1H-pyrazol-4-ylmethoxy)-propionylamino]-benzoic acid

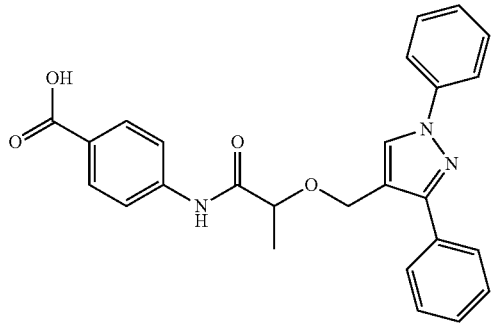 [SMILES: CC(OCc1cn(-c2ccccc2)nc1-c1ccccc1)C(=O)Nc1ccc(C(=O)O)cc1]

The title compound was prepared analogously as described in example 16.
MS (ES-): m/e=440.

Example 23

4-{2-[1-Benzyl-3-(3-methoxy-phenyl)-1H-pyrazol-4-ylmethoxy]-propionylamino}-benzoic acid

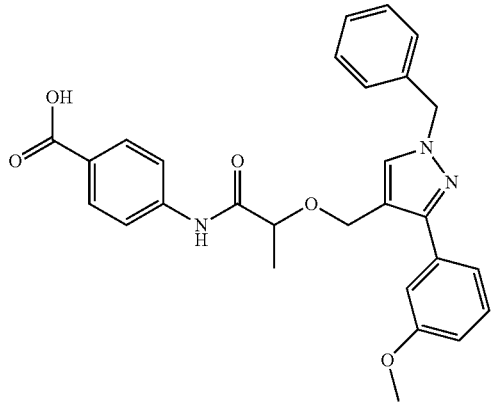 [SMILES: COc1cccc(-c2nn(Cc3ccccc3)cc2COC(C)C(=O)Nc2ccc(C(=O)O)cc2)c1]

The title compound was prepared analogously as described in example 16.
MS (ES-): m/e=484.

Example 24

4-{2-[5-(4-Fluoro-phenoxy)-1-methyl-3-phenyl-1H-pyrazol-4-ylmethoxy]-propionylamino}-benzoic acid

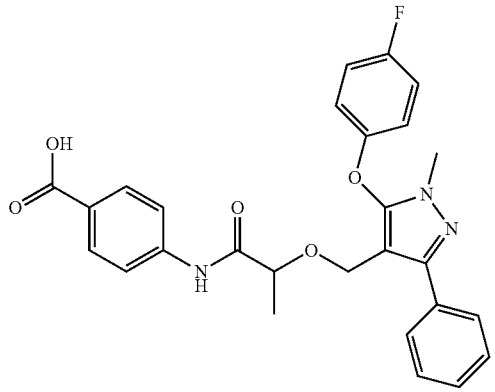 [SMILES: CC(OCc1c(-c2ccccc2)nn(C)c1Oc1ccc(F)cc1)C(=O)Nc1ccc(C(=O)O)cc1]

The title compound was prepared analogously as described in example 16.
MS (ES-): m/e=488.

Example 25

4-[2-(2-Methyl-2H-indazol-3-ylmethoxy)-propionylamino]-benzoic acid

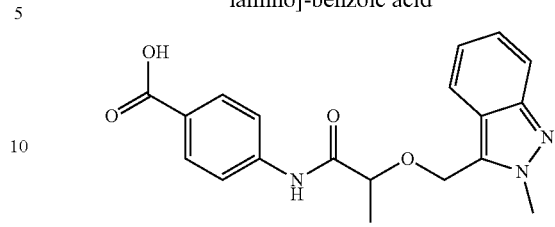

The title compound was prepared analogously as described in example 16.
MS (ES-): m/e=352.

Example 26

4-{2-[3-(4-Cyclohexyl-phenyl)-1-phenyl-1H-pyrazol-4-ylmethoxy]-propionylamino}-benzoic acid

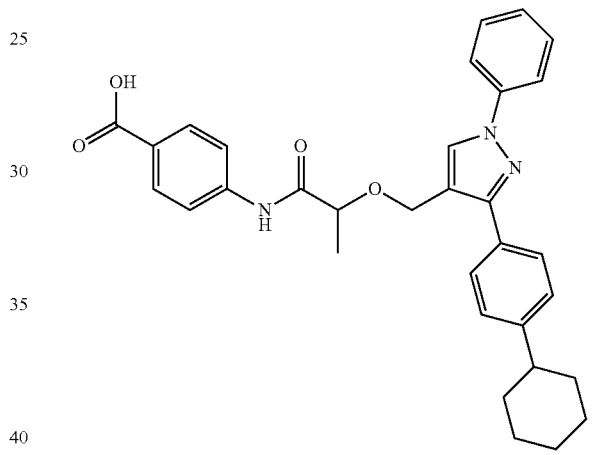

The title compound was prepared analogously as described in example 16.
MS (ES-): m/e=522.

Example 27

4-[2-(1-Phenyl-3-thiophen-2-yl-1H-pyrazol-4-ylmethoxy)-propionylamino]-benzoic acid

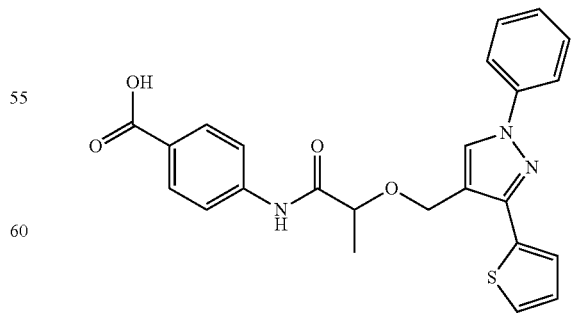

The title compound was prepared analogously as described in example 16.
MS (ES-): m/e=446.

Example 28

4-[2-(1,5-Diphenyl-1H-pyrazol-3-ylmethoxy)-propionylamino]-benzoic acid

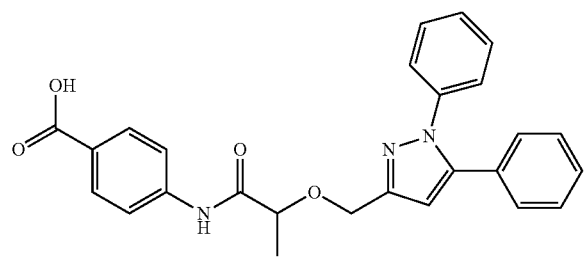 [SMILES: CC(OCc1cc(-c2ccccc2)n(-c2ccccc2)n1)C(=O)Nc1ccc(C(=O)O)cc1]

The title compound was prepared analogously as described in example 16.

MS (ES-): m/e=440.

Pharmacological Testing

The ability of the compounds of the formula I to inhibit or bind the LPA receptor LPAR5 can be assessed by determining the effect on cellular function. This ability of such compounds was evaluated in a platelet aggregation assay such as the Born method using single cuvettes and for mast cells and microglia cells with the Fluorometric Imaging Plate Reader (FLIPR) assay by Molecular Devices Inc.

A) Aggregation Assay for Washed Human Blood Platelets (Thrombocytes)

Whole blood was collected from healthy volunteers using 3×20 ml syringes containing each 1/10 volume of buffered citrate. The anticoagulated whole blood was transferred into 50 ml polypropylene conical tubes (30 ml per tube). The tubes were centrifuged for 10 minutes at 150×g at room temperature without using the centrifuge brake. This procedure results in a lower phase of cellular components and a supernatant (upper phase) of platelet rich plasma (PRP). The PRP phase was collected from each tube and pooled for each donor. To avoid carry over of cellular components following first centrifugation, approximately 5 ml of PRP was left in the tube. The platelet concentration was determined using a ABX Micros 60 counter. The PRP phase was transferred to a new 50 ml tube. After 10 minutes standing at room temperature, 1 µl PGI$_2$ (1 mM in Tris-HCl/pH 8.8) and 180 µl ACD/A were added per ml PRP. The PRP was then transferred to new 10 ml tube and centrifuged for 10 minutes at 500×g. After centrifugation a cellular pellet is visible at the bottom of the tube. The supernatant was carefully discarded and the cellular pellet, consisting of human blood platelets was then dissolved in 10 ml buffer T (buffer T composition: 145 mM NaCl, 5 mM KCl, 0.1 mM MgCl2×6 H$_2$O, 15 mM HEPES, 5.5 mM glucose, pH 7.4). Platelet concentration in this solution was determined and buffer T was added to obtain a final concentration of 3.5×10$^5$ platelets per ml.

After 10 minutes at room temperature, 1 µl PGI$_2$ per ml platelet solution was added and distributed into new 10 ml tubes. After a centrifugation step, 10 minutes at 500×g, supernatant was discarded and the platelets were resuspended in buffer T to a final concentration of 3.5×10$^5$ platelets per ml buffer T. Before use, platelet-containing buffer equilibrated for 30 minutes at room temperature. The human platelet aggregation assay was performed in single use cuvettes using the Platelet Aggregation Profiler® (PAP-4 or -8E, BIO/DATA Corporation). For a single experiment, 320 µl of platelet solution were transferred into an assay cuvette, 20 µl of calcium citrate solution (10 mM in H$_2$O) and 20 µl of fibrinogen solution (20 mg/ml H$_2$O) were added. The aggregation assay was performed in the assay cuvette at 37° C. and with 1.200 rpm stirring. To determine the EC$_{50}$, eight assay cuvettes were loaded as described above with different concentrations of LPA. Aggregation was measured over 6 minutes at 37° C. with 1200 rpm (revolutions per minute) stirring. Results of the assay are expressed as % activation, and are calculated using maximum aggregation (T$_{max}$) or area under curve (AUC) of the absorbance over 6 minutes. The inhibitory effect (IC$_{50}$) of the test compounds was determined as the reduction of the maximal aggregation. Test compound was added prior starting the experiment with an incubation time of the test compound of 5 minutes at 37° C. with 1200 rpm stirring. The IC$_{50}$ data of the above described platelet aggregation assay using human washed platelets for exemplary compounds of the present invention are shown in Table 1.

TABLE 1

| Example | IC$_{50}$ (µM) |
|---|---|
| 7 | 4.7 |
| 8 | 4.1 |
| 9 | 2.9 |
| 12 | 4.3 |
| 15 | 6.5 |
| 17 | 15.9 |

B) Use of the Fluorometric Imaging Plate Reader (FLIPR) Assay for the Determination of Intracellular Ca$^{2+}$ Release in Human Mast Cell Line HMC-1 and the Murine Microglia cell line BV-2

The ability of the compounds of the formula I to inhibit or bind the LPA receptor LPAR5 can be assessed by determining the intracellular Ca$^{2+}$ release in human or animal cells. For the analysis of activating potential of LPA and the inhibitory effects of compounds of the formula I two cell lines were used with high LPAR5 expression, the human mast cell line HMC-1 and the murine microglia cell line BV-2 (FIGS. 1 and 2). For the FLIPR assay using human mast cells in a 96-well-format, HMC-1 suspension cells from flask culture were harvested, resuspended and counted. 14×10$^6$ HMC-1 cells were transferred into a new 50 ml tube, centrifuged for 3 minutes at 540×g. The resulting cell pellet at the bottom of the tube was resuspended with 15 ml loading buffer (loading buffer contained HBSS buffer (pH 7.4), 0.1% BSA (bovine serum albumin), 2 µM FLUO-4 dye; HBSS buffer (pH 7.4) contained 1×HBSS, 20 mM HEPES, 0.01% Pluronic F-127, 2.5 mM Probenicid).

Cells in loading buffer were incubated for 45-60 minutes at 37° C. After incubation cells were centrifuged for 3 minutes at 540×g and resuspended with 21 ml of HBSS buffer (pH 7.4). Each well of a poly-D-lysine coated 96-well-plate was filled with 150 µl cell solution, an equivalent of 100 000 cells/well. The 96-well-plate was centifuged for 2 minutes at 100×g (without brake) prior a recovery time of 30 minutes at 37° C. After this procedure cells were stimulated with LPA (in HBSS pH 7.4 and 0.1% BSA) to determine the EC$_{50}$ of LPA in HMC-1 cells. For the determination of the inhibitory effect of compounds of the formula I, test compounds were added to the cells in the 96-well-plate 10 minutes prior the addition of LPA. Results of the assay are expressed as % activation, and are calculated using maximum peak of activation (A$_{max}$). The IC$_{50}$ data of the above described FLIPR assay using human mast cell line HMC-1 for exemplary compounds of the present invention are shown in Table 2. Adherent BV-2 cells were seeded onto poly-D-lysine coated 96-well-plates (100000 cells/well) the day before performing the FLIPR assay. The density of the cells in the 96-well-plate at the day of the FLIPR assay should be 90%. After aspiration of the culture media, BV-2 cells were incubated for 30 minutes at 37° C. with loading buffer and recovered in 150 μl HBSS buffer for 30 minutes at 37° C. After this procedure cells were stimulated with LPA (in HBSS pH 7.4 and 0.1% BSA) to determine the $EC_{50}$ of LPA in BV-2 cells. For the determination of the inhibitory effect of compounds of the formula I, test compounds were added to the cells in the 96-well-plate 10 minutes prior the addition of LPA. The $IC_{50}$ data of the above described FLIPR assay using the murine microglia cell line BV-2 for exemplary compounds of the present invention are shown in Table 3.

TABLE 2

| Example | $IC_{50}$ (μM) |
|---|---|
| 1 | 8.3 |
| 3 | 8.8 |
| 4 | 6.6 |
| 7 | 11.4 |
| 8 | 6.3 |
| 9 | 1.3 |
| 10 | 0.03 |
| 11 | 8.6 |
| 12 | 6.3 |
| 13 | 1.3 |
| 14 | 3.4 |
| 15 | 8.8 |
| 16 | 4.1 |
| 17 | 4.2 |
| 18 | 3.8 |
| 20 | 5.2 |
| 22 | 16 |

TABLE 3

| Example | $IC_{50}$ (μM) |
|---|---|
| 9 | 1.8 |
| 10 | 0.2 |

The invention claimed is:
1. A compound of the formula I,

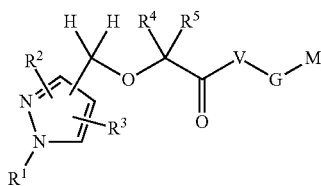

in any of its stereoisomeric forms or a mixture of stereoisomeric forms in any ratio, or a pharmaceutically acceptable salt thereof,
wherein
$R^1$ is selected from the series consisting of hydrogen, $(C_1$-$C_6)$-alkyl, $(C_3$-$C_7)$-cycloalkyl, $(C_3$-$C_7)$-cycloalkyl-$(C_1$-$C_4)$-alkyl-, Ar and Ar—$(C_1$-$C_4)$-alkyl-;
$R^2$ and $R^3$ are independently of each other selected from the series consisting of hydrogen, halogen, $(C_1$-$C_4)$-alkyl, $(C_3$-$C_7)$-cycloalkyl, $(C_3$-$C_7)$-cycloalkyl-$(C_1$-$C_4)$-alkyl-, Ar, Ar—$(C_1$-$C_4)$-alkyl-, $(C_1$-$C_4)$-alkyl-O—, $(C_3$-$C_7)$-cycloalkyl-O—, $(C_3$-$C_7)$-cycloalkyl-$(C_1$-$C_4)$-alkyl-O—, Ar—O— and Ar—$(C_1$-$C_4)$-alkyl-O—;

$R^4$ and $R^5$ are independently of each other selected from the series consisting of hydrogen, fluorine and $(C_1$-$C_6)$-alkyl;
or the groups $R^4$ and $R^5$ together with the carbon atom carrying them form a $(C_3$-$C_7)$-cycloalkane ring which is unsubstituted or substituted by one or more identical or different substituents selected from the series consisting of fluorine and $(C_1$-$C_4)$-alkyl;
$R^{11}$, $R^{12}$, $R^{13}$ and $R^{14}$ are independently of each other selected from the series consisting of hydrogen and $(C_1$-$C_4)$-alkyl;
Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1$-$C_4)$-alkyl, $(C_3$-$C_7)$-cycloalkyl, $(C_3$-$C_7)$-cycloalkyl-$(C_1$-$C_4)$-alkyl-, cyano and $(C_1$-$C_4)$-alkyl-O—;
V is selected from the series consisting of $R^{12}$—N($R^{13}$)—, and in this case G and M are not present, or
V is selected from the series consisting of —N($R^{14}$)—, —N($R^{14}$)—$(C_1$-$C_4)$-alkyl-, —O— and —O—$(C_1$-$C_4)$-alkyl-, and in this case G is selected from the series consisting of a direct bond and phenylene which is unsubstituted or substituted by one or more identical or different substituents selected from the series consisting of halogen, $(C_1$-$C_4)$-alkyl, cyano and $(C_1$-$C_4)$-alkyl-O—, provided that G is not a direct bond if V is —N($R^{14}$)— or —O—, and
M is selected from the series consisting of $R^{11}$—O—C(O)— and $R^{12}$—N($R^{13}$)—C(O)—;
wherein all alkyl groups are unsubstituted or substituted by one or more fluorine substituents, and all cycloalkyl groups are unsubstituted or substituted by one or more identical or different substituents selected from the series consisting of fluorine and $(C_1$-$C_4)$-alkyl;
provided that that the compound is not:
4-({2-[5-(4-Chloro-phenyl)-1-(2,4-dichloro-phenyl)-4-methyl- 1H-pyrazol-3-ylmethoxyl]-2-methyl-propionylamino}-methyl)-benzoic acid;
4-({2-[5-(4-Chloro-phenyl)-1-(2,4-dichloro-phenyl)-4-methyl-1H-pyrazol-3-ylmethoxyl]-acetylamino}-methyl)-benzoic acid;
4-({2-[5-(4-Chloro-phenyl)-1-(2,4-dichloro-phenyl)-4-methyl-1H-pyrazol-3-ylmethoxy]-butyrylamino}-methyl)-benzoic acid;
4-({2-[5-(4-Chloro-phenyl)-1-(2,4-dichloro-phenyl)-4-methyl-1H-pyrazol-3-ylmethoxy]-propionylamino}-methyl)-benzoic acid; and
provided that when $R^1$ is 2,4-dichlorophenyl, $R^2$ and $R^4$ are methyl, $R^3$ is 4-methylphenyl, 4-trifluoromethoxyphenyl or 2,4-dichlorophenyl, V is —NH—$CH_2$—, G is phenyl and M is —COOH, $R^5$ is not methyl; and
provided that when $R^1$ is 2,4-dichlorophenyl, $R^2$ and $R^4$ are methyl, $R^3$ is 4-trifluoromethylphenyl or 4-trifluoromethoxyphenyl, V is —$NH_2$, $R^5$ is not methyl; and
provided that when $R^1$ is 4-trifluoromethoxyphenyl, $R^2$ and $R^4$ are methyl, $R^3$ is 2,4-dichlorophenyl, V is —$NH_2$—$CH_2$—, G is phenyl and M is —COOH, $R^5$ is not methyl.
2. A compound of the formula I according to claim 1, wherein
$R^1$ is selected from the series consisting of hydrogen, $(C_1$-$C_6)$-alkyl, $(C_3$-$C_7)$-cycloalkyl, Ar and Ar—$(C_1$-$C_4)$-alkyl-;

$R^2$ and $R^3$ are independently of each other selected from the series consisting of hydrogen, $(C_1-C_4)$-alkyl, $(C_3-C_7)$-cycloalkyl, $(C_3-C_7)$-cycloalkyl-$(C_1-C_4)$-alkyl-, Ar, Ar—$(C_1-C_4)$-alkyl-, $(C_1-C_4)$-alkyl-O—, $(C_3-C_7)$-cycloalkyl-O—, $(C_3-C_7)$-cycloalkyl-$(C_1-C_4)$-alkyl-O—, Ar—O— and Ar—$(C_1-C_4)$-alkyl-O—;

$R^4$ and $R^5$ are independently of each other selected from the series consisting of hydrogen and $(C_1-C_6)$-alkyl;

or the groups $R^4$ and $R^5$ together with the carbon atom carrying them form a $(C_3-C_7)$-cycloalkane ring which is unsubstituted or substituted by one or more identical or different substituents selected from the series consisting of fluorine and $(C_1-C_4)$-alkyl;

$R^{11}$, $R^{12}$, $R^{13}$ and $R^{14}$ are independently of each other selected from the series consisting of hydrogen and $(C_1-C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1-C_4)$-alkyl, $(C_3-C_7)$-cycloalkyl, $(C_3-C_7)$-cycloalkyl-$(C_1-C_4)$-alkyl-, cyano and $(C_1-C_4)$-alkyl-O—;

V is selected from the series consisting of —N($R^{14}$)—, —N($R^{14}$)—$(C_1-C_4)$-alkyl- and —O—$(C_1-C_4)$-alkyl;

G is selected from the series consisting of a direct bond and phenylene which is unsubstituted or substituted by one or more identical or different substituents selected from the series consisting of halogen, $(C_1-C_4)$-alkyl, cyano and $(C_1-C_4)$-alkyl-O—, provided that G is not a direct bond if V is —N($R^{14}$)—; and M is selected from the series consisting of $R^{11}$—O—C(O)— and $R^{12}$—N($R^{13}$)—C(O)—;

wherein all alkyl groups are unsubstituted or substituted by one or more fluorine substituents, and all cycloalkyl groups are unsubstituted or substituted by one or more identical or different substituents selected from the series consisting of fluorine and $(C_1-C_4)$-alkyl;

in any of its stereoisomeric forms or a mixture of stereoisomeric forms in any ratio, or a pharmaceutically acceptable salt thereof.

3. A compound of the formula I according to claim 1, wherein $R^1$ is selected from the series consisting of $(C_1-C_6)$-alkyl, $(C_3-C_7)$-cycloalkyl, Ar and Ar—$(C_1-C_4)$-alkyl-;

$R^2$ and $R^3$ are independently of each other selected from the series consisting of hydrogen, $(C_1-C_4)$-alkyl, Ar, Ar—$(C_1-C_4)$-alkyl-, $(C_1-C_4)$-alkyl-O—, $(C_3-C_7)$-cycloalkyl-O—, Ar—O— and Ar—$(C_1-C_4)$-alkyl-O—;

$R^4$ and $R^5$ are independently of each other selected from the series consisting of hydrogen and $(C_1-C_6)$-alkyl;

or the groups $R^4$ and $R^5$ together with the carbon atom carrying them form a $(C_3-C_7)$-cycloalkane ring which is unsubstituted or substituted by one or more identical or different substituents selected from the series consisting of fluorine and $(C_1-C_4)$-alkyl;

$R^{11}$, $R^{12}$, $R^{13}$ and $R^{14}$ are independently of each other selected from the series consisting of hydrogen and $(C_1-C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1-C_4)$-alkyl, $(C_3-C_7)$-cycloalkyl and $(C_1-C_4)$-alkyl-O—;

V is selected from the series consisting of —N($R^{14}$)— and —N($R^{14}$)—$(C_1-C_4)$-alkyl-;

G is selected from the series consisting of a direct bond and phenylene which is unsubstituted or substituted by one or more identical or different substituents selected from the series consisting of halogen, $(C_1-C_4)$-alkyl and $(C_1-C_4)$-alkyl-O—, provided that G is not a direct bond if V is —N($R^{14}$)—; and M is selected from the series consisting of $R^{11}$—O—C(O)— and $R^{12}$—N($R^{13}$)—C(O)—;

wherein all alkyl groups are unsubstituted or substituted by one or more fluorine substituents, and all cycloalkyl groups are unsubstituted or substituted by one or more identical or different substituents selected from the series consisting of fluorine and $(C_1-C_4)$-alkyl;

in any of its stereoisomeric forms or a mixture of stereoisomeric forms in any ratio, or a pharmaceutically acceptable salt thereof.

4. A compound of the formula I according to claim 1, wherein $R^1$ is selected from the series consisting of $(C_1-C_4)$-alkyl, Ar and Ar—$(C_1-C_4)$-alkyl-;

$R^2$ and $R^3$ are independently of each other selected from the series consisting of hydrogen, $(C_1-C_4)$-alkyl, Ar, Ar—$(C_1-C_4)$-alkyl-, and Ar—O—;

$R^4$ and $R^5$ are independently of each other selected from the series consisting of hydrogen and $(C_1-C_6)$-alkyl;

or the groups $R^4$ and $R^5$ together with the carbon atom carrying them form a $(C_3-C_7)$-cycloalkane ring which is unsubstituted or substituted by one or more identical or different substituents selected from the series consisting of fluorine and $(C_1-C_4)$-alkyl;

$R^{11}$ and $R^{14}$ are independently of each other selected from the series consisting of hydrogen and $(C_1-C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1-C_4)$-alkyl, $(C_3-C_7)$-cycloalkyl and $(C_1-C_4)$-alkyl-O—;

V is selected from the series consisting of —N($R^{14}$)— and —N($R^{14}$)—$(C_1-C_4)$-alkyl-; and G is selected from the series consisting of a direct bond and phenylene which is unsubstituted or substituted by one or more identical or different substituents selected from the series consisting of halogen, $(C_1-C_4)$-alkyl and $(C_1-C_4)$-alkyl-O—, provided that G is not a direct bond if V is —N($R^{14}$), and M is $R^{11}$—O—C(O)—;

wherein all alkyl groups are unsubstituted or substituted by one or more fluorine substituents, and all cycloalkyl groups are unsubstituted or substituted by one or more identical or different substituents selected from the series consisting of fluorine and $(C_1-C_4)$-alkyl;

in any of its stereoisomeric forms or a mixture of stereoisomeric forms in any ratio, or a pharmaceutically acceptable salt thereof.

5. A compound of the formula I according to claim 1, wherein $R^1$ is selected from the series consisting of $(C_1-C_4)$-alkyl, Ar and Ar—$(C_1-C_4)$-alkyl-;

$R^2$ and $R^3$ are independently of each other selected from the series consisting of hydrogen, $(C_1-C_4)$-alkyl, Ar— and Ar—O—;

$R^4$ and $R^5$ are independently of each other selected from the series consisting of hydrogen and $(C_1-C_6)$-alkyl;

or the groups $R^4$ and $R^5$ together with the carbon atom carrying them form a $(C_3-C_7)$-cycloalkane ring which is unsubstituted or substituted by one or more fluorine substituents;

$R^{11}$ and $R^{14}$ are independently of each other selected from the series consisting of hydrogen and $(C_1-C_4)$-alkyl;

Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1-C_4)$-alkyl, $(C_3-C_7)$-cycloalkyl and $(C_1-C_4)$-alkyl-O—;

V is selected from the series consisting of —N($R^{14}$)— and —N($R^{14}$)—$(C_1-C_4)$-alkyl-; and G is selected from the series consisting of a direct bond and phenylene which is unsubstituted or substituted by one or more identical or different substituents selected from the series consisting of halogen, $(C_1-C_4)$-alkyl and $(C_1-C_4)$-alkyl-O—, provided that G is not a direct bond if V is —N($R^{14}$), and M is $R^{11}$—O—C(O)—;

wherein all alkyl groups are unsubstituted or substituted by one or more fluorine substituents;

in any of its stereoisomeric forms or a mixture of stereoisomeric forms in any ratio, or a pharmaceutically acceptable salt thereof.

6. A compound of the formula I according to claim 1, selected from the series consisting of:

4-({2-[1-(2,4-Dichloro-phenyl)-4-methyl-5-(4-trifluoromethyl-phenyl)-1H-pyrazol-3-ylmethoxy]-2-methyl-propionylamino}-methyl)-benzoic acid, 4-({2-[1-(2-Chloro-phenyl)-4-methyl-5-(4-trifluoromethyl-phenyl)-1H-pyrazol-3-ylmethoxy]-2-methyl-propionylamino}-methyl)-benzoic acid, 4-({2-[1-(4-Chloro-phenyl)-4-methyl-5-(4-trifluoromethyl-phenyl)-1H-pyrazol-3-ylmethoxy]-2-methyl-propionylamino}-methyl)-benzoic acid, 4-{2-[1-(2,4-Dichloro-phenyl)-4-methyl-5-(4-trifluoromethyl-phenyl)-1H-pyrazol-3-ylmethoxy]-propionylamino}-benzoic acid, 4-{2-[5-(4-Chloro-phenyl)-1-(2,4-dichloro-phenyl)-4-methyl-1H-pyrazol-3-ylmethoxy]-3-methyl-butyrylaminol}-benzoic acid, 4-{2-[1-(4-Chloro-phenyl)-4-methyl-5-(4-trifluoromethyl-phenyl)-1H-pyrazol-3-ylmethoxy]-propionylamino}-benzoic acid, 4-[2-(3-Naphthalen-2-yl-1-phenyl-1H-pyrazol-4-ylmethoxy)-propionylamino]-benzoic acid, 4-{2-[1-(2-Chloro-phenyl)-4-methyl-5-(4-trifluoromethyl-phenyl)-1H-pyrazol-3-ylmethoxy]-propionylamino}-benzoic acid, 4-[2-(3,5-Dimethyl-1-phenyl-1H-pyrazol-4-ylmethoxy)-propionylamino]-benzoic acid, 4-[2-(1,3-Diphenyl-1H-pyrazol-4-ylmethoxy)-propionylamino]-benzoic acid, 4-{2-[1-Benzyl-3-(3-methoxy-phenyl)-1 H-pyrazol-4-ylmethoxy]-propionylamino}-benzoic acid, 4-{2-[5-(4-Fluoro-phenoxy)-1-methyl-3-phenyl-1H-pyrazol-4-ylmethoxy]-propionylamino}-benzoic acid, 4-{2-[3-(4-Cyclohexyl-phenyl)-1-phenyl-1H-pyrazol-4-ylmethoxy]-propionylamino}-benzoic acid, 4-[2-(1-Phenyl-3-thiophen-2-yl-1H-pyrazol-4-ylmethoxy)-propionylamino]-benzoic acid, and 4-[2-(1,5-Diphenyl-1H-pyrazol-3-ylmethoxy)-propionylamino]-benzoic acid, in any of its stereoisomeric forms or a mixture of stereoisomeric forms in any ratio, or a pharmaceutically acceptable salt thereof.

7. A compound of the formula I according to claim 1, wherein $R^1$ is selected from the series consisting of $(C_1-C_4)$-alkyl, Ar and Ar—$(C_1-C_4)$-alkyl-, wherein the Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1-C_4)$-alkyl, $(C_3-C_7)$-cycloalkyl and $(C_1-C_4)$-alkyl-O—;

$R^2$ and $R^3$ are independently of each other selected from the series consisting of hydrogen, $(C_1-C_4)$-alkyl, Ar— and Ar—O—, wherein the Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more $(C_1-C_4)$-alkyl, wherein the alkyl group is substituted by one or more fluorine substituents;

$R^4$ and $R^5$ are independently of each other selected from the series consisting of hydrogen and $(C_1-C_6)$-alkyl; and V is selected from the series consisting of —N($R^{14}$)- and —N($R^{14}$)-$(C_1-C_4)$-alkyl-; in any of its stereoisomeric forms or a mixture of stereoisomeric forms in any ratio, or a pharmaceutically acceptable salt thereof.

8. A compound of the formula I according to claim 7, wherein $R^1$ is selected from the series consisting of Ar and Ar—$(C_1-C_4)$-alkyl-, wherein the Ar is selected from the series consisting of phenyl or naphthyl, each of which is unsubstituted or substituted by one or more identical or different substituents selected from the series consisting of halogen, $(C_1-C_4)$-alkyl, $(C_3-C_7)$-cycloalkyl and $(C_1-C_4)$-alkyl-O—;

$R^2$ and $R^3$ are independently of each other selected from the series consisting of hydrogen, $(C_1-C_4)$-alkyl and Ar—, wherein the Ar is selected from the series consisting of phenyl and naphthyl, each of which is unsubstituted or substituted by one or more $(C_1-C_4)$-alkyl, wherein the alkyl group is substituted by one or more fluorine substituents; in any of its stereoisomeric forms or a mixture of stereoisomeric forms in any ratio, or a pharmaceutically acceptable salt thereof.

9. A compound of the formula I according to claim 8, wherein $R^1$ is phenyl, unsubstituted or substituted by one or more identical or different substituents selected from the series consisting of halogen, $(C_1-C_4)$-alkyl, $(C_3-C_7)$-cycloalkyl and $(C_1-C_4)$-alkyl-O—;

$R^2$ and $R^3$ are independently of each other selected from the series consisting of hydrogen, $(C_1-C_4)$-alkyl and phenyl, unsubstituted or substituted by one or more $(C_1-C_4)$-alkyl, wherein the alkyl group is substituted by one or more fluorine substituents;

in any of its stereoisomeric forms or a mixture of stereoisomeric forms in any ratio, or a pharmaceutically acceptable salt thereof.

10. A compound of the formula I according to claim 9, wherein $R^1$ is phenyl substituted by one or more halogen;
$R^2$ is hydrogen or $(C_1-C_4)$-alkyl; and
$R^3$ is phenyl substituted by one or more $CF_3$;

in any of its stereoisomeric forms or a mixture of stereoisomeric forms in any ratio, or a pharmaceutically acceptable salt thereof.

11. A compound of the formula I according to claim 10, wherein $R^4$ is $(C_1-C_6)$-alkyl; and
$R^5$ is hydrogen.

12. A compound of the formula I according to claim 10, wherein $R^4$ and $R^5$ are each $(C_1-C_6)$-alkyl.

13. A method for the inhibition of the LPA receptor LPAR5 or the reduction or inhibition of platelet aggregation or thrombus formation or the reduction or inhibition of activation of mast cells or the reduction or inhibition of activation of microglial cells in a mammal in need thereof, the method comprising administering the mammal an compound of formula I,

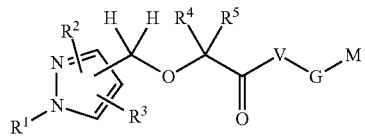

I wherein
$R^1$ is selected from the series consisting of hydrogen, $(C_1-C_6)$-alkyl, $(C_3-C_2)$-cycloalkyl, (C3-C7)-cycloalkyl-$(C_1-C_4)$-alkyl-, Ar and Ar—$(C_1-C_4)$-alkyl-;
$R^2$ and $R^3$ are independently of each other selected from the series consisting of hydrogen, halogen, $(C_1-C_4)$-alkyl, $(C_3-C_7)$-cycloalkyl, $(C_3-C_7)$-cycloalkyl-$(C_1-C_4)$-alkyl-, Ar, Ar—$(C_1-C_4)$-alkyl-, $(C_1-C_4)$-alkyl-O—, $(C_3-C_7)$-cycloalkyl-O—, $(C_3-C_7)$-cycloalkyl-$(C_1-C_4)$-alkyl-O—, Ar—O— and Ar—$(C_1-C_4)$-alkyl-O—;
$R^4$ and $R^5$ are independently of each other selected from the series consisting of hydrogen, fluorine and $(C_1-C_6)$-alkyl;
or the groups $R^4$ and $R^5$ together with the carbon atom carrying them form a $(C_3-C_7)$-cycloalkane ring which is unsubstituted or substituted by one or more identical or different substituents selected from the series consisting of fluorine and $(C_1-C_4)$-alkyl;
$R^{11}$, $R^{12}$, $R^{13}$ and $R^{14}$ are independently of each other selected from the series consisting of hydrogen and $(C_1-C_4)$-alkyl;
Ar is selected from the series consisting of phenyl, naphthyl and an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1-C_4)$-alkyl, $(C_3-C_7)$-cycloalkyl, $(C_3-C_7)$-cycloalkyl-$(C_1-C_4)$-alkyl-, cyano and $(C_1-C_4)$-alkyl-O—;

V is selected from the series consisting of $R^{12}$—N($R^{13}$)—, and in this case G and M are not present, or
V is selected from the series consisting of —N($R^{14}$)—, —N($R^{14}$)—$(C_1-C_4)$-alkyl-, —O— and —O—$(C_1-C_4)$-alkyl-, in this case G is selected from the series consisting of a direct bond and phenylene which is unsubstituted or substituted by one or more identical or different substituents selected from the series consisting of halogen, $(C_1-C_4)$-alkyl, cyano and $(C_1-C_4)$-alkyl-O—, provided that G is not a direct bond if V is —N($R^{14}$)—or —O—and
M is selected from the series consisting of $R^{11}$—O—C(O)—and $R^{12}$—N($R^{13}$)—C(O)—;
wherein all alkyl groups are unsubstituted or substituted by one or more fluorine substituents, and all cycloalkyl groups are unsubstituted or substituted by one or more identical or different substituents selected from the series consisting of fluorine and $(C_1-C_4)$-alkyl;
in any of its stereoisomeric forms or a mixture of stereoisomeric forms in any ratio, or a pharmaceutically acceptable salt thereof.

14. A method according to claim 13 wherein the method is for the treatment of thromboembolic diseases, deep vein thrombosis, venous or arterial thromboembolism, thrombophlebitis, coronary or cerebral arterial thrombosis, cerebral embolism, renal embolism, pulmonary embolism, disseminated intravascular coagulation, cardiovascular disorders, transient ischemic attacks, strokes, acute myocardial infarction, unstable angina, chronic stable angina, peripheral vascular disease, preeclampsia/eclampsia, thrombotic cytopenic purpura, inflammatory disorders, hyperalgesia, asthma, multiple sclerosis, inflammatory pain, angiogenesis, atherothrombosis, allergic responses, or restenosis.

15. A method according to claim 13 wherein the method is for the treatment of abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication, bypass grafting of the coronary or peripheral arteries, vessel luminal narrowing, restenosis post coronary venous angioplasty, maintenance of vascular access patency in long-term hemodialysis patients, pathologic thrombus formation occurring in the veins of the lower extremities following abdominal, knee or hip surgery, a risk of pulmonary thromboembolism, or disseminated systemic intravascular coagulatopathy occurring in vascular systems during septic shock, viral infections or cancer.

16. A method according to claim 13 wherein the method is for the treatment of inflammatory pain, asthma, angiogenesis, demyelating diseases of the central nervous system or the peripheral nervous system, multiple sclerosis, transverse myelitis, optic neuritis, Devic's disease, Guillain-Barre syndrome or chronic inflammatory demyelinating polyneuropathy.

17. A pharmaceutical composition comprising a compound of the formula I or a pharmaceutically acceptable salt thereof according to claim 1, and a pharmaceutically acceptable carrier.

18. A method for the inhibition of the LPA receptor LPAR5 or the reduction or inhibition of platelet aggregation or thrombus formation or the reduction or inhibition of activation of mast cells or the reduction or inhibition of activation of microglial cells in a mammal in need thereof, the method comprising administering the mammal an compound according to claim tin any of its stereoisomeric forms or a mixture of stereoisomeric forms in any ratio, or a pharmaceutically acceptable salt thereof.

19. A method according to claim 18, wherein the method is for the treatment of thromboembolic diseases, deep vein thrombosis, venous or arterial thromboembolism, thrombophlebitis, coronary or cerebral arterial thrombosis, cerebral embolism, renal embolism, pulmonary embolism, disseminated intravascular coagulation, cardiovascular disorders, transient ischemic attacks, strokes, acute myocardial infarction, unstable angina, chronic stable angina, peripheral vascular disease, preeclampsia/eclampsia, thrombotic cytopenic purpura, inflammatory disorders, hyperalgesia, asthma, multiple sclerosis, inflammatory pain, angiogenesis, atherothrombosis, allergic responses, restenosis, abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication, bypass grafting of the coronary or peripheral arteries, vessel luminal narrowing, restenosis post coronary venous angioplasty, maintenance of vascular access patency in long-term hemodialysis patients, pathologic thrombus formation occurring in the veins of the lower extremities following abdominal, knee or hip surgery, a risk of pulmonary thromboembolism, or disseminated systemic intravascular coagulatopathy occurring in vascular systems during septic shock, viral infections, cancer, inflammatory pain, asthma, angiogenesis, demyelating diseases of the central nervous system or the peripheral nervous system, multiple sclerosis, transverse myelitis, optic neuritis, Devic's disease, Guillain-Barre syndrome or chronic inflammatory demyelinating polyneuropathy.

\* \* \* \* \*